(12) United States Patent
Haaga et al.

(10) Patent No.: US 10,172,815 B2
(45) Date of Patent: Jan. 8, 2019

(54) TARGETED TREATMENT OF ANEROBIC CANCER

(71) Applicant: UNIVERSITY HOSPITALS CLEVELAND MEDICAL CENTER, Cleveland, OH (US)

(72) Inventors: John R Haaga, Chagrin Falls, OH (US); Rebecca Haaga, Chagrin Falls, OH (US)

(73) Assignee: UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 136 days.

(21) Appl. No.: 15/035,397

(22) PCT Filed: Nov. 7, 2014

(86) PCT No.: PCT/US2014/064589
§ 371 (c)(1),
(2) Date: May 9, 2016

(87) PCT Pub. No.: WO2015/070038
PCT Pub. Date: May 14, 2015

(65) Prior Publication Data
US 2016/0279084 A1  Sep. 29, 2016

Related U.S. Application Data

(60) Provisional application No. 61/902,456, filed on Nov. 11, 2013.

(51) Int. Cl.
| | | |
|---|---|---|
| *A61K 31/192* | (2006.01) | |
| *A61K 39/395* | (2006.01) | |
| *A61B 18/04* | (2006.01) | |
| *A61L 24/02* | (2006.01) | |
| *A61K 45/06* | (2006.01) | |
| *A61K 9/127* | (2006.01) | |
| *A61L 24/00* | (2006.01) | |
| *A61K 31/05* | (2006.01) | |
| *A61K 31/12* | (2006.01) | |
| *A61K 31/196* | (2006.01) | |
| *A61K 31/216* | (2006.01) | |
| *A61K 31/433* | (2006.01) | |
| *A61B 18/00* | (2006.01) | |
| *A61K 39/00* | (2006.01) | |

(52) U.S. Cl.
CPC ............ *A61K 31/192* (2013.01); *A61B 18/04* (2013.01); *A61K 9/127* (2013.01); *A61K 31/05* (2013.01); *A61K 31/12* (2013.01); *A61K 31/196* (2013.01); *A61K 31/216* (2013.01); *A61K 31/433* (2013.01); *A61K 39/3955* (2013.01); *A61K 45/06* (2013.01); *A61L 24/0015* (2013.01); *A61L 24/02* (2013.01); *A61B 2018/00577* (2013.01); *A61K 2039/505* (2013.01); *A61L 2300/436* (2013.01); *A61L 2300/606* (2013.01); *A61L 2430/36* (2013.01)

(58) Field of Classification Search
None
See application file for complete search history.

(56) References Cited

U.S. PATENT DOCUMENTS

| | | | |
|---|---|---|---|
| 4,761,288 A | 8/1988 | Mezei | 424/450 |
| 4,828,836 A | 5/1989 | Elger et al. | 424/419 |
| 5,646,185 A * | 7/1997 | Giaccia | A61K 31/00 514/548 |
| 5,944,021 A | 8/1999 | Rodriguez | 128/898 |
| 6,190,591 B1 | 2/2001 | Van Lengerich | 264/141 |
| 7,964,123 B2 | 6/2011 | Lanphere et al. | 264/11 |
| 2006/0035971 A1 | 2/2006 | Arai et al. | 514/570 |
| 2008/0160062 A1* | 7/2008 | Richard | A61L 31/04 424/423 |

FOREIGN PATENT DOCUMENTS

| | | |
|---|---|---|
| WO | WO/2009/032716 | 3/2009 |
| WO | WO2009/126705 | * 10/2009 |
| WO | WO/2013/130354 | 9/2013 |

OTHER PUBLICATIONS

Draoui et al (Bioorganic & Medicinal Chemistry, 2013, vol. 21, pp. 7107-7177, e-published Sep. 13, 2013) (Year: 2013).*
Kennedy et al (International Journal of Radiation Oncology, 2004, vol. 60, pp. 1552-1563) (Year: 2004).*
The abstract of Orsi et al (Cardiovascular and Interventional Radiology, 2009, vol. 32, suppl. 2, pp. 140-142, abstract No. 103.1) (Year: 2009).*
Koning et al (Pharmaceutical Research, 2010, vol. 27, pp. 1750-1754) (Year: 2010).*
Eid et al (Biochemical Pharmacology, 2010, vol. 79, pp. 444-454) (Year: 2010).*
Algharabil, J. et al. (2012) "Inhibition of Na(+)-K(+)-2C1(-) cotransporter isoform 1 accelerates temozolomide-mediated apoptosis in glioblastoma cancer cells," *Cellular Physiology and Biochemistry* 30(1), 33-48.
Allen, T. M. et al. (2013) "Liposomal drug delivery systems: From concept to clinical applications," *Advanced Drug Delivery Reviews* 65(1), 36-48.

(Continued)

*Primary Examiner* — Karen A. Canella
(74) *Attorney, Agent, or Firm* — Medlen & Carroll, LLP

(57) ABSTRACT

The present invention relates to a pharmaceutical cocktail and methods of cancer treatment. In particular, one such cocktail comprises a combination of effective amounts of a lactate transporter inhibitor, a carbonic anhydrase inhibitor, a sodium potassium chloride cofactor (NKCC) transporter inhibitor, a member of the hydroxycinnamate class of drugs or a derivative thereof, and/or an angiogenesis inhibitor, including a vascular endothelial growth factor (VEGF) inhibitor such as bevacizumab in combination with blood vessel occlusion. As most cancers in an untreated state uses both aerobic and anaerobic/glycolytic pathways treatments contemplated herein can affect both metabolic pathways.

21 Claims, 45 Drawing Sheets

(56) References Cited

OTHER PUBLICATIONS

Barrett, T. et al. (2007) "MRI of tumor angiogenesis," *Journal of Magnetic Resonance Imaging* 26(2), 235-249.
Barrett, T. et al. (2006) "Macromolecular MRI contrast agents for imaging tumor angiogenesis," *European Journal of Radiology* 60(3), 353-366.
Baumann, F. et al. (2009) "Lactate promotes glioma migration by TGF-β2-dependent regulation of matrix metalloproteinase-2," *Neuro-oncology* 11(4), 368-380.
Brasch, R. et al. (1997) "Assessing tumor angiogenesis using macromolecular MR imaging contrast media," *Journal of Magnetic Resonance Imaging* 7(1), 68-74.
Breslau, J. et al. (1995) "Preoperative Embolization of Spinal Tumors," *Journal of Vascular and Interventional Radiology* 6(6), 871-875.
Brown, M. et al. (2008) "NF-κB in carcinoma therapy and prevention," *Expert Opinion on Therapeutic Targets* 12(9), 1109-1122.
Cao, Y. et al. (1998) "Vascular endothelial growth factor C induces angiogenesis in vivo," *Proceedings of the National Academy of Sciences* 95(24), 14389-14394.
Carli, D. F. M. et al. (2010) "Complications of Particle Embolization of Meningiomas: Frequency, Risk Factors, and Outcome," *American Journal of Neuroradiology* 31(1), 152-154.
Chang, L. K. et al. (2004) "Dose-dependent response of FGF-2 for lymphangiogenesis," *Proceedings of the National Academy of Sciences* 101(32), 11658-11663.
Chaudary, N. et al. (2007) "Hypoxia and Metastasis," *Clinical Cancer Research* 13(7), 1947-1949.
Chen, H. X. et al. (2001) "Clinical trials referral resource: Current clinical trials of the anti-VEGF monoclonal antibody bevacizumab," *Oncology (Williston Park)* 15(8), 1017, 1020, 1023-1016.
Cobleigh, M. A. et al. (2003) "A phase I/II dose-escalation trial of bevacizumab in previously treated metastatic breast cancer," *Seminars in Oncology* 30, 117-124.
Coleman, C. N. et al. (2002) "Tumor Hypoxia: Chicken, Egg, or a Piece of the Farm?," *Journal of Clinical Oncology* 20(3), 610-615.
Colen, C. B. et al. (2011) "Metabolic Targeting of Lactate Efflux by Malignant Glioma Inhibits Invasiveness and Induces Necrosis: An in Vivo Study," *Neoplasia* 13(7), 620-632.
Cruz, H. et al. (2000) "Effects of ammonia and lactate on growth, metabolism, and productivity of BHK cells," *Enzyme and Microbial Technology* 27(1-2), 43-52.
D'Arcangelo, D. et al. (2000) "Acidosis Inhibits Endothelial Cell Apoptosis and Function and Induces Basic Fibroblast Growth Factor and Vascular Endothelial Growth Factor Expression," *Circulation Research* 86(3), 312-318.
Dewhirst, M. W. et al. (1999) "Quantification of longitudinal tissue pO2 gradients in window chamber tumours: impact on tumour hypoxia," *British Journal of Cancer* 79(11-12), 1717-1722.
Dvorak, H. et al. (1988) "Identification and characterization of the blood vessels of solid tumors that are leaky to circulating macromolecules," *American Journal of Pathology* 133, 95-109.
Dvorak, H. F. (2003) "How Tumors Make Bad Blood Vessels and Stroma," *American Journal of Pathology* 162(6), 1747-1757.
Eichten, A. et al. (2007) "Distinctive Features of Angiogenesis and Lymphangiogenesis Determine Their Functionality during De novo Tumor Development," *Cancer Research* 67(11), 5211-5220.
Feng, Y. et al. (2008) "Characterization of tumor angiogenesis with dynamic contrast-enhanced MRI and biodegradable macromolecular contrast agents in mice," *Magnetic Resonance in Medicine* 60(6), 1347-1352.
Figg, W. D. et al. (2002) "Inhibition of Angiogenesis: Treatment Options for Patients with Metastatic Prostate Cancer," *Investigational New Drugs* 20(2), 183-194.
Finstein, J. L. et al. (2006) "Postembolization paralysis in a man with a thoracolumbar giant cell tumor," *Clinical Orthopaedics & Related Research* 453, 335-340.
Fischer, K. et al. (2007) "Inhibitory effect of tumor cell-derived lactic acid on human T cells," *Blood* 109(9), 3812-3819.
Folkman, J. (2000) "Incipient Angiogenesis," *Journal of the National Cancer Institute* 92(2), 94-95.
Fukumura, D. et al. (2001) "Hypoxia and Acidosis Independently Up-Regulate Vascular Endothelial Growth Factor Transcription in Brain Tumors in Vivo," *Cancer Research* 61(16), 6020-6024.
Gatenby, R. et al. (2006) "Acid-mediated tumor invasion: a multidisciplinary study," *Cancer Research* 66(10), 5216-5223.
Giavazzi, R. et al. (2001) "Modulation of Tumor Angiogenesis by Conditional Expression of Fibroblast Growth Factor-2 Affects Early but not Established Tumors," *Cancer Research* 61(1), 309-317.
Gillies, R. J. et al. (2007) "Adaptive landscapes and emergent phenotypes: why do cancers have high glycolysis?," *Journal of Bioenergetics and Biomembranes* 39(3), 251-257.
Gimbrone, M. A. et al. (1972) "Tumor Dormancy in Vivo by Prevention of Neovascularization," *Journal of Experimental Medicine* 136(2), 261-276.
Goerges, A. L. et al. (2004) "pH Regulates Vascular Endothelial Growth Factor Binding to Fibronectin: A Mechanism for Control of Extracellular Matrix Storage and Release," *Journal of Biological Chemistry* 279(3), 2307-2315.
Gordon, M. S. et al. (2001) "Phase I Safety and Pharmacokinetic Study of Recombinant Human Anti-Vascular Endothelial Growth Factor in Patients With Advanced Cancer," *Journal of Clinical Oncology* 19(3), 843-850.
Gullino, P. M. et al. (1964) "The Interstitial Fluid of Solid Tumors," *Cancer Research* 24(5), 780-797.
Haaga, J. R. et al. (2013) "Acidic lactate sequentially induced lymphogenesis, phlebogenesis, and arteriogenesis (ALPHA) hypothesis: Lactate-triggered glycolytic vasculogenesis that occurs in normoxia or hypoxia and complements the traditional concept of hypoxia-based vasculogenesis," *Surgery*(0), (e-published Jul. 13, 2013).
Haas, B. R. et al. (2010) "Inhibition of the Sodium-Potassium-Chloride Cotransporter Isoform-1 reduces glioma invasion," *Cancer Res* 70(13), 5597-5606.
Henderson, E. et al. (2000) "Simultaneous MRI measurement of blood flow, blood volume, and capillary permeability in mammary tumors using two different contrast agents," *Journal of Magnetic Resonance Imaging* 12(6), 991-1003.
Hunt, T. et al. (2007) "Aerobically derived lactate stimulates revascularization and tissue repair via redox mechanisms," *Antioxidants & Redox Signaling* 9(8), 1115-1124.
Hurwitz, H. (2003) Bevacizumab (Avastin, a monoclonal antibody to vascular endothelial growth factor) prolongs survival in first-line colorectal cancer (CRC): results of a phase III trial of bevacizumab in combination with bolus IFL (irinotecan, 5-fluorouracil, leucovorin), in *Presented at the 39th Annual American Society of Clinical Oncology Meeting*, Chicago, IL.
Indraccolo, S. et al. (2006) "Interruption of tumor dormancy by a transient angiogenic burst within the tumor microenvironment," *Proceedings of the National Academy of Sciences of the United States of America* 103(11), 4216-4221.
Iwamoto, L. M. et al. (2004) "Na-K-2Cl cotransporter inhibition impairs human lung cellular proliferation," *American Journal of Physiology—Lung Cellular and Molecular Physiology* 287(3), L510-514.
Karin, M. (2009) "NF-κB as a Critical Link Between Inflammation and Cancer," *Cold Spring Harbor Perspectives in Biology* 1(5).
Keunen, O. et al. (2011) "Anti-VEGF treatment reduces blood supply and increases tumor cell invasion in glioblastoma," *Proceedings of the National Academy of Sciences* 108(9), 3749-3754.
Kim, J.-w. et al. (2006) "Cancer's Molecular Sweet Tooth and the Warburg Effect," *Cancer Research* 66(18), 8927-8930.
Klenke, F. et al. (2007) "Tyrosine kinase inhibitor SU6668 represses chondrosarcoma growth via antiangiogenesis in vivo," *BMC Cancer* 7(1), 49.
Koh, T. S. et al. (2011) "Fundamentals of tracer kinetics for dynamic contrast-enhanced MRI," *Journal of Magnetic Resonance Imaging* 34(6), 1262-1276.
Kohn, S. et al. (1992) "Pathways of macromolecular tracer transport across venules and small veins. Structural basis for the hyperpermeability of tumor blood vessels," *Laboratory Investigation* 67(5), 596-607.

(56) References Cited

OTHER PUBLICATIONS

Kondoh, H. et al. (2005) "Glycolytic Enzymes Can Modulate Cellular Life Span," *Cancer Research* 65(1), 177-185.
Kumar, V. B. S. et al. (2007) "Endothelial cell response to lactate: Implication of PAR modification of VEGF," *Journal of Cellular Physiology* 211(2), 477-485.
Kwon, J. H. et al. (2010) "Preoperative transcatheter arterial embolization of hypervascular metastatic tumors of long bones," *Acta Radiologica* 51(4), 396-401.
Lao, M.-S. et al. (1997) "Effects of Ammonium and Lactate on Growth and Metabolism of a Recombinant Chinese Hamster Ovary Cell Culture," *Biotechnology Progress* 13(5), 688-691.
Leite, T. C. et al. (2011) "Lactate downregulates the glycolytic enzymes hexokinase and phosphofructokinase in diverse tissues from mice," *FEBS Letters* 585(1), 92-98.
Li, C.-Y. et al. (2000) "Initial Stages of Tumor Cell-Induced Angiogenesis: Evaluation Via Skin Window Chambers in Rodent Models," *Journal of the National Cancer Institute* 92(2), 143-147.
Llovet, J. M. et al. (2002) "Arterial embolisation or chemoembolisation versus symptomatic treatment in patients with unresectable hepatocellular carcinoma: a randomised controlled trial," *Lancet* 359(9319), 1734-1739.
Lu, H. et al. (2005) "Reversible Inactivation of HIF-1 Prolyl Hydroxylases Allows Cell Metabolism to Control Basal HIF-1," *Journal of Biological Chemistry* 280(51), 41928-41939.
Lu, H. et al. (2002) "Hypoxia-inducible Factor 1 Activation by Aerobic Glycolysis Implicates the Warburg Effect in Carcinogenesis," *Journal of Biological Chemistry* 277(26), 23111-23115.
Madhu, M. et al. (2009) "Biodegradable Injectable Implant Systems for Sustained Delivery Using Poly (Lactide-Co-Glycolide) Copolymers," *International Journal of Pharmacy and Pharmaceutical Sciences* 1(1), 103-107.
Mankoff, D. A. et al. (2002) "Blood Flow and Metabolism in Locally Advanced Breast Cancer: Relationship to Response to Therapy," *Journal of Nuclear Medicine* 43(4), 500-509.
Martinez-Outschoorn, U. E. et al. (2011) "Ketones and lactate increase cancer cell "stemness," driving recurrence, metastasis and poor clinical outcome in breast cancer: Achieving personalized medicine via Metabolo-Genomics," *Cell Cycle* 10(8), 1271-1286.
Marx, E. et al. (1988) "Lactate-induced inhibition of tumor cell proliferation," *International Journal of Radiation Oncology Biology Physics* 14(5), 947-955.
Maxwell, C. et al. (2008) "Cell-surface and mitotic-spindle RHAMM: moonlighting or dual oncogenic functions?," *Journal of Cell Science* 121(Pt 7), 925-932.
McFate, T. et al. (2008) "Pyruvate Dehydrogenase Complex Activity Controls Metabolic and Malignant Phenotype in Cancer Cells," *Journal of Biological Chemistry* 283(33), 22700-22708.
Milovanova, T. N. et al. (2008) "Lactate Stimulates Vasculogenic Stem Cells via the Thioredoxin System and Engages an Autocrine Activation Loop Involving Hypoxia-Inducible Factor 1," *Molecular and Cellular Biology* 28(20), 6248-6261.
Nagy, J. A. et al. (2006) "Permeability properties of tumor surrogate blood vessels induced by VEGF-A," *Laboratory Investigation* 86(8), 767-780.
Nagy, J. A. et al. (2002) "Vascular Permeability Factor/Vascular Endothelial Growth Factor Induces Lymphangiogenesis as well as Angiogenesis," *Journal of Experimental Medicine* 196(11), 1497-1506.
O'Connor, J. P. et al. (2007) "DCE-MRI biomarkers in the clinical evaluation of antiangiogenic and vascular disrupting agents," *British Journal of Cancer* 96(2), 189-195.
O'Connor, J. P. et al. (2012) "Dynamic contrast-enhanced MRI in clinical trials of antivascular therapies," *Nature Reviews Clinical Oncology* 9(3), 167-177.
Ozturk, S. S. et al. (1992) "Effects of ammonia and lactate on hybridoma growth, metabolism, and antibody production," *Biotechnology and Bioengineering* 39(4), 418-431.

Padhani, A. R. et al. (2001) "Dynamic contrast-enhanced MRI studies in oncology with an emphasis on quantification, validation and human studies," *Clinical Radiology* 56(8), 607-620.
Padhani, A. R. et al. (2005) "Antivascular cancer treatments: functional assessments by dynamic contrast-enhanced magnetic resonance imaging," *Abdominal Imaging* 30(3), 324-341.
Patan, S. et al. (2001) "Vascular Morphogenesis and Remodeling in a Human Tumor Xenograft: Blood Vessel Formation and Growth After Ovariectomy and Tumor Implantation," *Circulation Research* 89(8), 732-739.
Pettersson, A. et al. (2000) "Heterogeneity of the Angiogenic Response Induced in Different Normal Adult Tissues by Vascular Permeability Factor/Vascular Endothelial Growth Factor," *Laboratory Investigation* 80(1), 99-115.
Puma, F. et al. (2008) "Preoperative embolization in surgical management of giant thoracic sarcomas," *European Journal of Cardio-Thoracic Surgery* 33(1), 127-129.
Quennet, V. et al. (2006) "Tumor lactate content predicts for response to fractionated irradiation of human squamous cell carcinomas in nude mice," *Radiotherapy & Oncology* 81(2), 130-135.
Robert, J. et al. (2008) "Preoperative Embolization of Hypervascular Castleman's Disease of the Mediastinum," *Cardiovascular and Interventional Radiology* 31(1), 186-188.
Rutz, H. P. (1999) "A biophysical basis of enhanced interstitial fluid pressure in tumors," *Medical Hypotheses* 53(6), 526-529.
Salven, P. et al. (2003) "VEGFR-3 and CD133 identify a population of CD34+ lymphatic/vascular endothelial precursor cells," *Blood* 101(1), 168-172.
Samuvel, D. J. et al. (2009) "Lactate Boosts TLR4 Signaling and NF-κB Pathway-Mediated Gene Transcription in Macrophages via Monocarboxylate Transporters and MD-2 Up-Regulation," *Journal of Immunology* 182(4), 2476-2484.
Sattler, U. G. A. et al. (2010) "Glycolytic metabolism and tumour response to fractionated irradiation," *Radiotherapy & Oncology* 94(1), 102-109.
Schirmer, C. M. et al. (2006) "Preoperative Embolization of Hypervascular Spinal Metastases Using Percutaneous Direct Injection with n-Butyl Cyanoacrylate: Technical Case Report," *Neurosurgery* 59(2), E431-E432.
Semenza, G. L. (2008) "Tumor metabolism: cancer cells give and take lactate," *Journal of Clinical Investigation* 118(12), 3835-3837.
Shi, H. B. et al. (1999) "Preoperative Transarterial Embolization of Spinal Tumor: Embolization Techniques and Results," *American Journal of Neuroradiology* 20(10), 2009-2015.
Shi, Q. et al. (2001) "Regulation of vascular endothelial growth factor expression by acidosis in human cancer cells," *Oncogene* 20(28), 3751-3756.
Siemann, D. W. (2011) "The unique characteristics of tumor vasculature and preclinical evidence for its selective disruption by Tumor-Vascular Disrupting Agents," *Cancer Treatment Reviews* 37(1), 63-74.
Sirsi, S. et al. (2009) "Microbubble Compositions, Properties and Biomedical Applications," *Bubble Science, Engineering & Technology* 1(1-2), 3-17.
Sonveaux, P. et al. (2008) "Targeting lactate-fueled respiration selectively kills hypoxic tumor cells in mice," *Journal of Clinical Investigation* 118(12), 3930-3942.
Sourbron, S. (2010) "Technical aspects of MR perfusion," *European Journal of Radiology* 76(3), 304-313.
Sourbron, S. P. et al. (2012) "Tracer kinetic modelling in MRI: estimating perfusion and capillary permeability," *Physics in Medicine and Biology* 57(2), R1-33.
St Lawrence, K. S. et al. (1998) "An adiabatic approximation to the tissue homogeneity model for water exchange in the brain: I. Theoretical derivation," *Journal of Cerebral Blood Flow and Metabolism* 18(12), 1365-1377.
Sundaresan, N. et al. (1990) "Treatment of spinal metastases from kidney cancer by presurgical embolization and resection," *Journal of Neurosurgery* 73(4), 548-554.
Swietach, P. et al. (2007) "Regulation of tumor pH and the role of carbonic anhydrase 9," *Cancer and Metastasis Reviews* 26(2), 299-310.

(56) References Cited

OTHER PUBLICATIONS

Tofts, P. S. (1997) "Modeling tracer kinetics in dynamic Gd-DTPA MR imaging," *Journal of Magnetic Resonance Imaging* 7(1), 91-101.

Tofts, P. S. et al. (1995) "Quantitative analysis of dynamic Gd-DTPA enhancement in breast tumors using a permeability model," *Magnetic Resonance in Medicine* 33(4), 564-568.

Tseng, D. et al. (2011) "Targeting SDF-1/CXCR4 to inhibit tumour vasculature for treatment of glioblastomas," *British Journal of Cancer* 104(12), 1805-1809.

Tsutsui, J. M. et al. (2004) "The use of microbubbles to target drug delivery," *Cardiovascular Ultrasound* 2, 23.

Turkbey, B. et al. (2010) "The role of dynamic contrast-enhanced MRI in cancer diagnosis and treatment," *Diagnostic and Interventional Radiology* 16(3), 186-192.

Vander Heiden, M. G. et al. (2009) "Understanding the Warburg Effect: The Metabolic Requirements of Cell Proliferation," *Science* 324(5930), 1029-1033.

Végran, F. et al. (2011) "Lactate Influx through the Endothelial Cell Monocarboxylate Transporter MCT1 Supports an NF-κB/IL-8 Pathway that Drives Tumor Angiogenesis," *Cancer Research* 71(7), 2550-2560.

Warburg, O. (1966) The Prime Cause and Prevention of Cancer, in *Annual Meeting of Nobel Laureates* Jun. 30, 1966, Landau, Germany.

Wu, H. et al. (2009) "Dynamic Evolutionary Changes in Blood Flow Measured by MDCT in a Hepatic VX2 Tumor Implant over an Extended 28-day Growth Period: Time-Density Curve Analysis," *Academic Radiology* 16(12), 1483-1492.

Wu, X. et al. (2009) "Tumor characterization with dynamic contrast enhanced magnetic resonance imaging and biodegradable macromolecular contrast agents in mice," *Pharmaceutical Research* 26(9), 2202-2208.

Xu, L. et al. (2002) "Acidic Extracellular pH Induces Vascular Endothelial Growth Factor (VEGF) in Human Glioblastoma Cells via ERK1/2 MAPK Signaling Pathway," *Journal of Biological Chemistry* 277(13), 11368-11374.

Yoshiji, H. et al. (1997) "Vascular Endothelial Growth Factor Is Essential for Initial but not Continued in Vivo Growth of Human Breast Carcinoma Cells," *Cancer Research* 57(18), 3924-3928.

Zabel, D. D. et al. (1996) "Lactate stimulation of macrophage-derived angiogenic activity is associated with inhibition of Poly(ADP-ribose) synthesis," *Laboratory Investigation* 74(3), 644-649.

Zhao, S. et al. (2005) "Biologic Correlates of Intratumoral Heterogeneity in 18F-FDG Distribution with Regional Expression of Glucose Transporters and Hexokinase-II in Experimental Tumor," *Journal of Nuclear Medicine* 46(4), 675-682.

PCT International Search Report of International Application No. PCT/US2014/064589 dated Jan. 27, 2015.

* cited by examiner

TARGETED TREATMENT OF ANEROBIC CANCER

CROSS-REFERENCE TO RELATED APPLICATIONS

The present application claims the benefit of U.S. Provisional Patent Application No. 61/902,456, filed on. Nov. 11, 2013, which is incorporated herein by reference.

FIELD OF THE INVENTION

The present invention relates to a pharmaceutical cocktail and methods of cancer treatment. In particular, one such cocktail comprises a combination of effective amounts of lactate transporter inhibitor, a carbonic anhydrase inhibitor, a sodium potassium chloride cofactor (NKCC) transporter inhibitor, a member of the hydroxycinnamate class of drugs or a derivative thereof, and/or an angiogenesis inhibitor, including a vascular endothelial growth factor (VEGF) inhibitor such as bevacizumab in combination with blood vessel occlusion. As most cancers in an untreated state uses both aerobic and anaerobic/glycolytic pathways treatments contemplated herein can affect both metabolic pathways.

BACKGROUND OF THE INVENTION

While a number of anti-angiogenesis agents have been reported, including bevacizumab, it is not clear whether they possess the appropriate pharmacological effectiveness required to be therapeutically useful in the treatment of cancer in many situations. Therefore, there is a continued need for additional therapeutics to target such cancer and augment or revive the effectiveness of anti-angiogenesis agents to provide effective treatment of cancer.

Cancers and cancerous lesions are known for their ability to adapt to treatment in various ways including shifts in metabolism, i.e. aerobic to glycoysis, or mutations to avoid pharmaceutical treatments. What is needed in the art is a method of treatment, which can hinder the metabolic pathways or options for such adaptive cancers.

SUMMARY OF THE INVENTION

The present invention relates to a pharmaceutical cocktail and methods of cancer treatment. In particular, one such cocktail comprises a combination of effective amounts of a lactate transporter inhibitor, a carbonic anhydrase inhibitor, a sodium potassium chloride cofactor (NKCC) transporter inhibitor, a member of the hydroxycinnamate class of drugs or a derivative thereof, and/or an angiogenesis inhibitor, including a vascular endothelial growth factor (VEGF) inhibitor such as bevacizumab in combination with blood vessel occlusion. As most cancers in an untreated state uses both aerobic and anaerobic/glycolytic pathways treatments contemplated herein can affect both metabolic pathways.

Although it is not necessary to understand the mechanism of an invention, it is believed that treatments that target the anaerobic and aerobic metabolic pathways more completely deprives cancer of ATP energy production, thereby producing greater damage or killing of cancerous cells. Treatment of the aerobic pathway alone temporarily controls cancer but it induces mutation to a glycolytic form, which does not respond to anti-VEGF or other anti-vascular growth factor agents.

In other embodiments, the present invention relates to compositions and methods of treating cancer involving effective amounts of a member of the hydroxycinnamate class of drugs. Pharmaceutical compositions and methods of treating cancer (eliminating the tumor, shrinking the tumor, prolonging the life of the patient, increasing quality of life by decreasing the grade of adverse events seen with other cancer treatments, and/or preventing/reducing the likelihood of the tumor's metastases) are additional aspects of the present invention. In addition, the present invention may be used to favorably affect the therapeutic result of patients who have not responded to alternative, traditional anti-cancer therapy.

In one embodiment, the invention contemplates a method for treating cancer comprising: a) administering an effective amount of a lactate transporter inhibitor to a patient comprising a cancerous lesion, wherein the cancerous lesion comprises a plurality of blood vessels, and b) occluding at least one of said plurality of blood vessel. In one embodiment, said lactate transporter inhibitor is delivered via liposomes. In one embodiment, said lactate transporter inhibitor is delivered via a small particle delivery system. In one embodiment, said small particle delivery system is selected from the group comprising liposomes, poly (lactide-co-glycolide) (PLG), nanoparticles formed by poly (beta-amino ester)s (PBAEs), and drug containing microbubbles which rupture upon insonation by ultrasound. In one embodiment, the occluding reduces blood flow to said cancerous lesion. In one embodiment, the method further comprises administering to said patient an effective amount of an angiogenesis inhibitor. In one embodiment, said angiogenesis inhibitor is a humanized monoclonal antibody. In one embodiment, said treating comprises repeated administration of at least one of the lactate transporter inhibitor and angiogenesis inhibitor. In one embodiment, said antibody is bevacizumab. In one embodiment, said lactate transporter inhibitor is a hydoxycinnamate derivative. In one embodiment, said hydoxycinnamate derivative is selected from the group consisting of ferrulic acid, caffeic acid, chorogenic acid, resveratrol ferulate, and phloretin ferulate. In one embodiment, said cancer is a hypoxic cancer. In one embodiment, said occluding results in the shrinkage of said cancer. In one embodiment, said occluding further comprises an embolism. In one embodiment, said embolism is produced by the introduction of an embolic composition. In one embodiment, said embolic composition comprises a plurality of polymers embedded with lactate transporter inhibitors. In one embodiment, said embolic composition comprises liposomes that contain lactate transporter inhibitor(s). In one embodiment, said embolic composition comprises a small particle delivery system that contain lactate transporter inhibitor(s). In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound. In one embodiment, said embolic composition comprises a plurality of glass beads coated with at least one lactate transporter inhibitor. In one embodiment, said occluding further comprises thermal ablation.

In one embodiment, the invention contemplates a method of treating cancer comprising administering to a patient an effective amount of at least one lactate transporter inhibitor, at least one a carbonic anhydrase inhibitor, at least one NKCC inhibitor, and at least one angiogenesis inhibitor. In one embodiment, said angiogenesis inhibitor is a humanized monoclonal antibody. In one embodiment, said administering is repeated. In one embodiment, said antibody is bevacizumab. In one embodiment, said lactate transporter inhibitor, a carbonic anhydrase inhibitor, and an angiogenesis inhibitor are administered as a pharmaceutical cocktail. In one embodiment, said lactate transporter inhibitor is delivered via liposomes. In one embodiment, said lactate transporter inhibitor is delivered via a small particle delivery system. In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound. In one embodiment, said NKCC inhibitor is delivered via a small particle delivery system. In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound. In one embodiment, both said lactate transporter inhibitor and said NKCC inhibitor are both delivered via a small particle delivery system. In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound. In one embodiment, said at least one lactate transporter inhibitor, at least one a carbonic anhydrase inhibitor, and at least one angiogenesis inhibitor are administered in series. In one embodiment, said cancer is a hypoxic cancer. In one embodiment, said carbonic anhydrase inhibitor is a carbonic anhydrase 9 and carbonic anhydrase 12 inhibitor. In one embodiment, said administering results in the shrinkage of a cancerous lesion. In one embodiment, said administering reduces metastases of said cancerous lesion.

In one embodiment, the invention contemplates a pharmaceutical composition comprising an effective amount of a lactate transporter inhibitor, a loop diuretic NKCC inhibitor, and an angiogenesis inhibitor. In one embodiment, said angiogenesis inhibitor is bevacizumab. In one embodiment, said loop diuretic is bumetanide. In one embodiment, said lactate transporter inhibitor is a hydoxycinnamate derivative. In one embodiment, said angiogenesis inhibitor is packaged within liposomes. In one embodiment, said angiogenesis inhibitor is packaged within a small particle delivery system. In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound. In one embodiment, said lactate transporter inhibitor is packaged within liposomes. In one embodiment, said lactate transporter inhibitor is packaged within a small particle delivery system. In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound. In one embodiment, said NKCC inhibitor is delivered via liposomes. In one embodiment, said NKCC inhibitor is delivered via a small particle delivery system. In one embodiment, said small particle delivery system is selected from the group comprising liposomes, poly (lactide-co-glycolide) (PLG), nanoparticles formed by poly (beta-amino ester)s (PBAEs), and drug containing microbubbles which rupture upon insonation by ultrasound. In one embodiment, said angiogenesis inhibitor, said lactate transporter inhibitor, and said NKCC inhibitor are all delivered via a small particle delivery system. In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound. In one embodiment, said hydoxycinnamate derivative includes, but is not limited to, ferrulic acid, caffeic acid, chorogenic acid, resveratrol ferulate, and phloretin ferulate. In one embodiment, said composition is formulated for oral administration. In one embodiment, said composition is formulated for parenteral administration. In one embodiment, said composition is formulated for intravenous administration.

In one embodiment, the invention contemplates a method of treating cancer comprising administering to a patient a composition comprising an effective amount of a lactate transporter inhibitor, a carbonic anhydrase inhibitor, and an angiogenesis inhibitor. In one embodiment, said composition is delivered via liposomes. In one embodiment, said composition is delivered via a small particle delivery system. In one embodiment, said small particle delivery system is selected from the group comprising liposomes, poly (lactide-co-glycolide) (PLG), nanoparticles formed by poly (beta-amino ester)s (PBAEs), and drug containing microbubbles which rupture upon insonation by ultrasound. In one embodiment, said angiogenesis inhibitor is a humanized monoclonal antibody. In one embodiment, said composition comprising at least one lactate transporter inhibitor, a carbonic anhydrase inhibitor, and an angiogenesis inhibitor is administered as a pharmaceutical cocktail. In one embodiment, said treating comprises repeated administration of at least one of the lactate transporter inhibitor, a carbonic anhydrase inhibitor, and an angiogenesis inhibitor. In one embodiment, said antibody is bevacizumab. In one embodiment, said lactate transporter inhibitor, a carbonic anhydrase inhibitor, and an angiogenesis inhibitor are administered to said patient at the same time. In one embodiment, said cancer is hypoxic cancer. In one embodiment, said carbonic anhydrase inhibitor is a carbonic anhydrase 9 and carbonic anhydrase 12 inhibitor. In one embodiment, said carbonic anhydrase inhibitor is acetazolamide. In one embodiment, said administering results in the shrinkage of said cancerous lesion. In one embodiment, said patient has metastases and said administration reduces metastases of said cancerous lesion.

In one embodiment, the invention contemplates a method of treating cancer comprising administering to a patient a composition comprising an effective amount of a lactate transporter inhibitor, a NKCC inhibitor, and an angiogenesis inhibitor. In one embodiment, said composition is delivered via liposomes. In one embodiment, said composition is delivered via a small particle delivery system. In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound. In one embodiment, said angiogenesis inhibitor is a humanized monoclonal antibody. In one embodiment, said composition comprising at least one lactate transporter inhibitor, NKCC inhibitor, and an angiogenesis inhibitor is administered as a pharmaceutical cocktail. In one embodiment, said treating comprises repeated administration of at least one of the lactate transporter inhibitor, NKCC inhibitor, and an angiogenesis inhibitor. In one embodiment, said antibody is bevacizumab. In one embodiment, said lactate transporter inhibitor, a NKCC inhibitor, and an angiogenesis inhibitor are administered to said patient at the same time. In one embodiment, said cancer is hypoxic cancer. In one embodiment, said NKCC inhibitor is bumetanide. In one embodiment, said administering results in the shrinkage of said cancerous lesion. In one embodiment, said patient has metastases and said administration reduces metastases of said cancerous lesion.

In one embodiment, the invention contemplates a pharmaceutical composition comprising an effective amount of a lactate transporter inhibitor, a carbonic anhydrase inhibitor, and an angiogenesis inhibitor. In one embodiment, said angiogenesis inhibitor is bevacizumab. In one embodiment, said carbonic anhydrase inhibitor is acetazolamide. In one embodiment, said lactate transporter inhibitor, carbonic anhydrase inhibitor, and said angiogenesis inhibitor are in a mixture. In one embodiment, said composition is formulated for oral administration. In one embodiment, said composition is formulated for parenteral administration. In one embodiment, said composition is formulated for intravenous administration. In one embodiment, said composition is packaged within liposomes. In one embodiment, said composition is packaged within a small particle delivery system. In one embodiment, said small particle delivery system is selected from the group comprising liposomes, poly (lactide-co-glycolide) (PLG), nanoparticles formed by poly (beta-amino ester)s (PBAEs), and drug containing microbubbles which rupture upon insonation by ultrasound.

In one embodiment, the invention contemplates a pharmaceutical composition comprising an effective amount of a lactate transporter inhibitor, a NKCC inhibitor, and an angiogenesis inhibitor. In one embodiment, said angiogenesis inhibitor is bevacizumab. In one embodiment, said lactate transporter inhibitor, a NKCC inhibitor, and said angiogenesis inhibitor are in a mixture. In one embodiment, said composition is formulated for oral administration. In one embodiment, said composition is formulated for parenteral administration. In one embodiment, said composition is formulated for intravenous administration. In one embodiment, said composition is packaged within liposomes. In one embodiment, said composition is packaged within a small particle delivery system. In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound.

In one embodiment, the invention contemplates a pharmaceutical composition comprising an effective amount of a lactate transporter inhibitor, a carbonic anhydrase inhibitor, NKCC inhibitor, and an angiogenesis inhibitor. In one embodiment, said angiogenesis inhibitor is bevacizumab. In one embodiment, said lactate transporter inhibitor, carbonic anhydrase inhibitor, and said angiogenesis inhibitor are in a mixture. In one embodiment, said composition is formulated for oral administration. In one embodiment, said composition is formulated for parenteral administration. In one embodiment, said composition is formulated for intravenous administration. In one embodiment, said composition is packaged within liposomes. In one embodiment, said composition is packaged within a small particle delivery system. In one embodiment, said small particle delivery system is selected from the group comprising liposomes, poly (lactide-co-glycolide) (PLG), nanoparticles formed by poly (beta-amino ester)s (PBAEs), and drug containing microbubbles which rupture upon insonation by ultrasound.

In one embodiment, the invention contemplates a method for treating a patient with cancer, wherein said cancer is unresponsive to traditional therapy, said method comprising administering to said patient a composition comprising at least one lactate transporter inhibitor. In one embodiment, the lactate transporter inhibitor is a hydroxycinnamate derivative. In one embodiment, the administering results in a clinical remission of said cancer. In one embodiment, the administering results in an increased quality of life. In one embodiment, the administering prolongs the survival of the patient. In one embodiment, said administering results in the shrinkage of tumor size and/or diameter. In one embodiment, said administering induces cancer dormancy. In one embodiment, said administering results in a complete remission of said cancer. In one embodiment, said lactate transporter inhibitor is a hydoxycinnamate derivative. In one embodiment, said hydoxycinnamate derivative includes, but is not limited to, ferrulic acid, caffeic acid, chorogenic acid, resveratrol ferulate, and phloretin ferulate. In one embodiment, said composition is packaged within liposomes. In one embodiment, said composition is packaged within a small particle delivery system. In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound.

In one embodiment, the invention contemplates a method for treating a patient with cancer, wherein said cancer is unresponsive to traditional therapy, said method comprising administering to said patient a combination of a lactate transporter inhibitor a carbonic anhydrase inhibitor, and an angiogenesis inhibitor. In one embodiment, the lactate transporter inhibitor is a hydroxycinnamate derivative. In one embodiment, said combination is packaged within liposomes. In one embodiment, said combination is packaged within a small particle delivery system. In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound. In one embodiment, the administering results in a clinical remission of said cancer. In one embodiment, the administering results in an increased quality of life. In one embodiment, the administering prolongs the survival of the patient. In one embodiment, said administering results in the shrinkage of a tumor. In one embodiment, the administering induces cancer dormancy. In one embodiment, said administering results in a complete remission of said cancer. In one embodiment, said angiogenesis inhibitor is bevacizumab. In one embodiment, said carbonic anhydrase inhibitor is bumetanide. In one embodiment, said hydoxycinnamate derivative includes, but is not limited to, ferrulic acid, caffeic acid, chorogenic acid, resveratrol ferulate, and phloretin ferulate.

In one embodiment, the invention relates to the treatment of hypoxic cancer. In one embodiment, treatment of hypoxic cancer includes an intravenous injection of a carbonic anhydrase inhibitor. In one embodiment, said intravenous injection of carbonic anhydrase inhibitor comprises injection into the blood vessels directly adjacent to said cancer. In one embodiment, the carbonic anhydrase inhibitor is acetazolamide. In one embodiment, treatment comprises catheterization of the hepatic artery. In one embodiment, treatment comprises occluding arteries with the treatment of acetazolamide. In one embodiment, treatment comprises embolization. In one embodiment, treatment comprises inducing an embolism with a plurality of polymers embedded with carbonic anhydrase inhibitors. In one embodiment, said embolization comprises embolization with carbonic anhydrase inhibitors on glass beads or other inert material. In one embodiment, said carbonic anhydrase inhibitors include a carbonic anhydrase 9 or 12 inhibitor, such as acetazolamide. In one embodiment, said polymers are embedded with carbonic anhydrase inhibitors that slowly release acetazolamide. In one embodiment, said treatment bumetanide is given intravenously in combination with a plurality of polymers embedded with carbonic anhydrase inhibitors.

In one embodiment, the invention contemplates the treatment of cancer. In one embodiment, said cancer comprises well-defined tumors. In one embodiment, said treatment involves thermal ablation of arteries supplying blood to well defined tumors in combination with treatment with a hydoxycinnamate derivative. In one embodiment, said hydoxycinnamate derivative includes, but is not limited to, ferrulic acid, caffeic acid, chorogenic acid, resveratrol ferulate, and phloretin ferulate. In one embodiment, treatment comprises additional treatment with an angiogenesis inhibitor. In one embodiment, said angiogenesis inhibitor includes but is not limited to ZD6474, ZD 6126, AZD2171, SU6668 and SU5416, bevacizumab, mv833, anti-FLT-1 ribozyme, SU5416, PTK 787, ZD4190, ZD6474, CEP-7055, SU11248, and mixtures thereof.

In one embodiment, the invention contemplates a method for treating a patient with cancer, said method comprising administering to said patient a lactate transporter inhibitor and occlusion of blood vessels providing blood to said cancer effective to provide a clinical benefit remission, an increased quality of life or prolongation of survival of the patient. In one embodiment, said lactate transporter inhibitor is packaged within liposomes. In one embodiment, said lactate transporter inhibitor is packaged within a small particle delivery system. In one embodiment, said small particle delivery system is selected from the group comprising liposomes, poly (lactide-co-glycolide) (PLG), nanoparticles formed by poly(beta-amino ester)s (PBAEs), and drug containing microbubbles which rupture upon insonation by ultrasound. In one embodiment, said lactate transporter inhibitor is a hydoxycinnamate derivative. In one embodiment, said hydoxycinnamate derivative is selected from the group consisting of ferrulic acid, caffeic acid, chorogenic acid, resveratrol ferulate, and phloretin ferulate. In one embodiment, said cancer is hypoxic cancer. In one embodiment, said treatment results in the shrinkage of a tumor or prolonged stability of the cancer. In one embodiment, said method results in a complete remission of said cancer. In one embodiment, said occlusion of blood vessels providing blood to said cancer comprises embolization. In one embodiment, said embolization comprises embolization with polymers embedded with lactate transporter inhibitors. In one embodiment, said embolization comprises embolization with lactate transporter inhibitors on glass beads or other inert material. This embodiment provides treatment of aerobic cancer cells by occlusion of the arteries and treatment of the glycolytic cancer cells by direct action of the lactate transporter inhibitor and indirectly by inhibition of lactate transportation. In one embodiment, said occlusion of blood vessels providing blood to said cancer comprises thermal ablation. In one embodiment, said treatment of said cancer with thermal ablation is preceded with lactate transporter inhibitor treatment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "Prevention" or "preventing" as used herein includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "effective," as that term is used in the specification and/or claims, means adequate to accomplish a desired, or hoped for result.

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

As used herein, the term "patient" or "subject" refers to a living animal, generally a mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses. In certain embodiments, "patient" or "subject" is used to describe an animal, generally a mammal and preferably a human, to whom treatment, including prophylactic treatment, with the compositions according to the present invention is provided. For treatment of those infections, conditions or disease states, which are specific for a specific animal such as a human patient, the term patient refers to that specific animal.

As used herein, "embolization" refers to a non-surgical, minimally invasive procedure performed by an interventional radiologist and interventional neuroradiologists. It involves the selective occlusion of blood vessels by purposely introducing emboli. The purpose of embolization is to prevent blood flow to an area of the body, which effectively can shrink a tumor or block an aneurysm and/or deliver therapeutic drugs or/and agents. The procedure is carried out as an endovascular procedure by a consultant radiologist in an interventional suite. It is common for most patients to have the treatment carried out with little or no sedation, although this depends largely on the organ to be embolized. Patients who undergo cerebral embolization or portal vein embolization are usually given a general anesthetic. Access to the organ in question is acquired by means of a guidewire and catheter(s). Depending on the organ, this can be very difficult and time consuming. The position of the correct artery or vein supplying the pathology in question is located by digital subtraction angiography (DSA). These images are then used as a map for the radiologist to gain access to the correct vessel by selecting an appropriate catheter and or wire, depending on the 'shape' of the surrounding anatomy. Once in place, the treatment can begin. The artificial embolus used is usually, but not limited to, one of the following: Guglielmi detachable coil or hydrocoil, beads, particles, foam, and plug.

As used herein, "embolic compositions" refers to compositions that can be used to prevent or to treat certain conditions in the body. For example, in therapeutic vascular occlusions (sometimes called "embolizations"), particulate embolic compositions can be used to block, or occlude, vessels in the body. The embolic compositions can be used to block microvascular supplies of blood to tumors (thereby depriving the tumors of resources to grow), or to block hemorrhagic conditions in the body (thereby reducing or stopping bleeding). The compositions can be delivered to a target site using a catheter that has been introduced into the vessel.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, including soft tissue sarcomas, which may be treated by the combination of compounds according to the present invention.

The term "remission" or "clinical benefit remission" is used to describe a remission in a patient's cancer, which may be a complete remission, a partial remission or evidence of stability of the disease.

The term "coadministration" or "combination therapy" is used to describe a therapy in which at least two active compounds or compositions in effective amounts (in the present application, at least bumetanide is coadministered with the angiogenesis inhibitor, preferably bevacizumab also being coadministered or being administered before or after the administration of bumetanide) to treat cancer, and preferably both compounds are used to treat a disease state or condition as otherwise described herein at the same time. In some embodiments, the invention involves administration of an additional chemotherapy compound(s) or composition(s).

Although the term coadministration preferably includes the administration of at least two active compounds to the patient at the same time, it is not necessary that the compounds be administered to the patient at the same time, although effective amounts of the individual compounds will be present in the patient at the same time.

The term "traditional cancer therapy" as used herein includes, but is not limited to radiation, surgical removal of cancerous tissue, and treatment with chemotherapeutic drugs, which generally have significant toxicity and undesirable side effects.

The term "carbonic anhydrase(s)" (CAs) as used herein refer to a large family of zinc metalloenzymes that catalyze the reversible hydration of carbon dioxide. They participate in a variety of biological processes, including, but not limited to, respiration, calcification, acid-base balance, bone resorption, and the formation of aqueous humor, cerebrospinal fluid, saliva, and gastric acid. Carbonic anhydrase 9 (CA9) is an enzyme that in humans is encoded by the CA9 gene and carbonic anhydrase 12 (CA12) is an enzyme that in humans is encoded by the CA12 gene. CA9 and CA12 are most commonly present in many cancer types, i.e. colon, breast, brain, kidney, lung etc. but uncommonly present in normal tissues, making them suitable for therapeutic targeting.

The term "angiogenesis inhibitor", "vascular endothelial growth factor inhibitor" "VEGF inhibitor" or "anti-VEGF therapy" all used within context, refers to a compound, composition or therapy which inhibits or otherwise prevents the angiogenesis effects of vascular endothelial growth factor (VEGF, a factor which is involved in the angiogenesis of tissue, including growth in and vascularization of tumors), regardless of mechanism.

As used herein, bumetanide (also known under trade names Bumex or Burinex) is a loop diuretic, a NKCC inhibitor, and an aquaporin inhibitor. Bumetanide is a thiazide diuretic. The IUPAC name is 3-butylamino-4-phenoxy-5-sulfamoyl-benzoic acid. Bumetanide has the chemical structure:

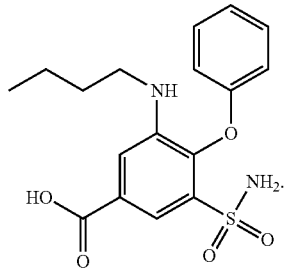 [SMILES: CCCCNc1cc(C(=O)O)cc(S(N)(=O)=O)c1Oc1ccccc1]

As used herein, a NKCC inhibitor refers to an inhibitor of a Na—K—Cl cotransporter (NKCC) protein that aids in the active transport of sodium, potassium, and chloride into and out of cells.

As used herein, acetazolamide (also known under trade name Diamox) is a carbonic anhydrase inhibitor and a diuretic. Acetazolamide has the chemical structure:

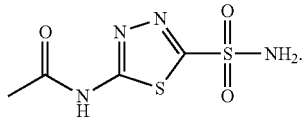

As used herein, "hydroxycinnamate class of drugs" refers to a class of polyphenols having a C6-C3 skeleton. These compounds are hydroxy derivatives of cinnamic acid. Particular examples include ferulic acid, and caffeic acid.

As used herein, "cinnamic acid" refers to a compound with the following structure:

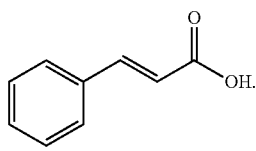 [SMILES: O=C(O)/C=C/c1ccccc1]

As used herein, "ferulic acid" refers to a compound with the following structure:

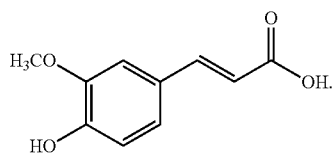 [SMILES: COc1cc(/C=C/C(=O)O)ccc1O]

As used herein, "caffeic acid" refers to a compound with the following structure:

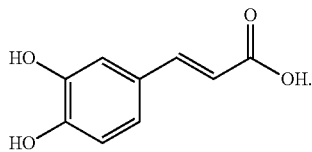 [SMILES: O=C(O)/C=C/c1ccc(O)c(O)c1]

As used herein, "phlorietin" refers to a compound with the following structure:

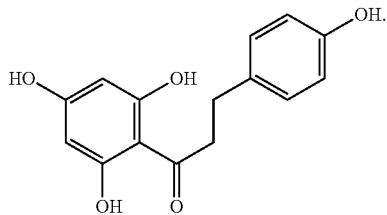 [SMILES: O=C(CCc1ccc(O)cc1)c1c(O)cc(O)cc1O]

As used herein, "substituted resveratrol" refers to a compound with the following structure:

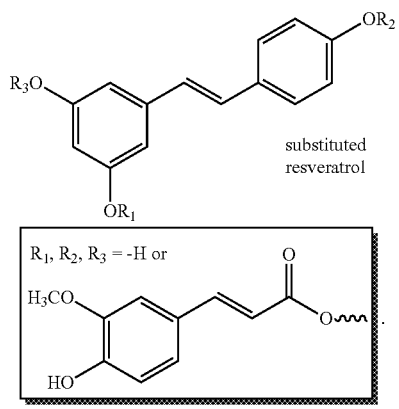

As used herein, thiazides are a class of drug that promotes water loss from the body ((diuretics)). They inhibit Na+/Cl— reabsorption from the distal convoluted tubules in the kidneys. Thiazides also cause loss of potassium and an increase in serum uric acid. The chemical structure of the original thiazide diuretics contained a thiazide ring system; the term is also used for drugs with a similar action that are not chemically thiazides, such as chorthalidone.

As used herein, aquaporins refer to proteins embedded in the cell membrane that regulate the flow of water. Aquaporins selectively conduct water molecules in and out of the cell, while preventing the passage of ions and other solutes. Also known as water channels, aquaporins are integral membrane pore proteins. Some of them, known as aquaglyceroporins, transport also other small uncharged solutes, such as glycerol, carbon dioxide, ammonia and urea across the membrane, depending on the size of the pore.

As used herein, thermal ablation is a method of removing aberrant tissue from within the body preferably via minimally invasive procedures. There are several types of thermal ablation used to destroy targeted tissue: cryoablation uses extremely cold temperatures to freeze diseased tissue, radiofrequency ablation uses heat generated by radiofrequency energy, microwave ablation uses heat generated by microwave energy, Laser ablation uses heat from a laser beam, and ultrasound ablation uses heat from focused ultrasound energy.

The term "occluding" as used herein refers to cause to become closed, such as blood vessels; to obstruct or occlude an artery. Embolization is one method of occluding blood vessels or lymphatic vessels.

The term "salts", as used herein, refers to any salt that complexes with identified compounds contained herein while retaining a desired function, e.g., biological activity. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Pharmaceutically acceptable salts also include base addition salts, which may be formed when acidic protons present are capable of reacting with inorganic or organic bases. Suitable pharmaceutically-acceptable base addition salts include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, and trimethylamine. All of these salts may be prepared by conventional means from the corresponding compound of the invention by reacting, for example, the appropriate acid or base with the compound of the invention. Unless otherwise specifically stated, the present invention contemplates pharmaceutically acceptable salts of the considered pro-drugs.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

In structures wherein stereochemistry is not explicitly indicated, it is assumed that all stereochemistry is considered and all isomers claimed.

Any undefined valency on an atom of a structure shown in this application implicitly represents a hydrogen atom bonded to the atom. Bonds to copper (Cu) metal may be coordinate bonds and are not necessarily considered covalent.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

The term "Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts, which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002) [1] herein incorporated by reference. Unless otherwise specifically stated, the present invention contemplates pharmaceutically acceptable salts of the considered pro-drugs.

As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

Enantiomers are compounds that individually have properties said to have "optical activity" and consist of molecules with at least one chiral center, almost always a carbon atom. If a particular compound is dextrorotary, its enantiomer will be levorotary, and vice-versa. In fact, the enantiomers will rotate polarized light the same number of degrees, but in opposite directions. "Dextrorotation" and "levorotation" (also spelled laevorotation) refer, respectively, to the properties of rotating plane polarized light clockwise (for dextrorotation) or counterclockwise (for levorotation). A compound with dextrorotation is called "dextrorotary," while a compound with levorotation is called "levorotary."

A standard measure of the degree to which a compound is dextrorotary or levorotary is the quantity called the "specific rotation" "α". Dextrorotary compounds have a positive specific rotation, while levorotary compounds have negative. Two enantiomers have equal and opposite specific rotations. A dextrorotary compound is prefixed "(+)-" or "d-". Likewise, a levorotary compound is often prefixed "(−)" or "l-". These "d-" and "l-" prefixes should not be confused with the "D-" and "L-" prefixes based on the actual configuration of each enantiomer, with the version synthesized from naturally occurring (+)-compound being considered the D-form. A mixture of enantiomers of the compounds is prefixed "(±)-". An equal mixture of enantiomers of the compounds is considered "optically inactive."

As used herein, "liposomes" means an artificially-prepared vesicle composed of a lipid bilayer. The liposome can be used as a vehicle for administration of nutrients and pharmaceutical drugs. Liposomes can be prepared by disrupting biological membranes (such as by sonication). Liposomes are often composed of phosphatidylcholine-enriched phospholipids and may also contain mixed lipid chains with surfactant properties such as egg phosphatidylethanolamine. A liposome design may employ surface ligands for attaching to unhealthy tissue. The major types of liposomes are the multilamellar vesicle (MLV), the small unilamellar vesicle (SUV), the large unilamellar vesicle (LUV), and the cochleate vesicle [2]. A number of liposomes (lipidic nanoparticles) are on the market, and many more are in the pipeline [3]. The liposomes may additionally contain one or more types of charged vesicle forming lipids, e.g. phosphatidylglycerol, phosphatidyletha nolamine, (di)stearylamine, phosphatidylserine, dioleoyl trimethylammonium propane, phosphatidic acids and cholesterol hemisuccinate.

As used herein, "poly (lactide-co-glycolide) (PLG)" refers to a biodegradable synthetic polymer for sustained release formulations, such as described in Madhu et al. (2009) [4]. In some embodiments, PLG may also include PLGA or poly(lactic-co-glycolic acid). PLGA is synthesized by means of ring-opening co-polymerization of two different monomers, the cyclic dimers (1,4-dioxane-2,5-diones) of glycolic acid and lactic acid. Polymers can be synthesized as either random or block copolymers thereby imparting additional polymer properties.

As used herein, "poly(beta-amino ester)s or (PBAEs)" refers to nanoparticles of poly(beta-amino) esters. Poly (beta-amino) esters are degraded by hydrolysis of the ester bonds in the polymer backbone, enabling reduced cytotoxicity when compared to non-degradable controls. Poly(beta-amino) esters may also be end modified to synthetically attach one or more desired therapeutic agents.

As used herein, "drug containing microbubbles which rupture upon insonation by ultrasound" refers to bubbles smaller than one millimeter in diameter, but larger than one micrometer [5]. Microbubbles may be used for drug delivery [6]. Two possible strategies for delivering drugs and genes with microbubbles are emerging. The first consists on the ultrasound-mediated microbubble destruction, which is based on the cavitation of microbubbles induced by ultrasound application, and the second is the direct delivery of substances bound to microbubbles in the absence of ultrasound. In some embodiments, liposomes and microbubbles may be combined.

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

The present invention contemplates the above-described compositions in "therapeutically effective amounts" or "pharmaceutically effective amounts", which means that amount which, when administered to a subject or patient for treating a disease, is sufficient to effect such treatment for the disease or to ameliorate one or more symptoms of a disease or condition (e.g. ameliorate pain).

In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

Pharmaceutically acceptable sugars include but are not limited to sucrose, dextrose, maltose, galactose, rhamnose, and lactose. Pharmaceutically acceptable sugar alcohols include but are not limited to mannitol, xylitol, and sorbitol.

As used herein, "extended release" refers to providing continuous therapeutic level of an active agent (e.g., neuregulin) over a period of time. The extended release includes, without limitation various forms of release, such as continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slow acting, sustained action, sustained-action medications, and controlled release. The ability to obtain extended release, controlled release, timed release, sustained release, delayed release, long acting, pulsatile delivery or immediate release is performed using well-known procedures and techniques available to the ordinarily skilled artisan.

The amount of time over which the active agent continues to be released depends on the characteristics of the active agent and the extended release technology or technologies used, but in all cases is longer than that of administration of the active agent without the extended release technology or technologies. Other forms of slow release compositions are described in the following: U.S. Pat. No. 4,828,836 [7], U.S. Pat. No. 6,190,591 [8].

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 24A shows a control group. FIG. 24B shows the TAE treatment group. FIG. 24C shows the results of the TAE+Bumex (butetanide).

FIG. 41A shows saline therapy. FIG. 41B shows bumetanide therapy. The images displayed here show the spatial changes in the Fp, Ps and Vp parameters that developed over time for both the saline control (FIG. 41A) and bumetanide (FIG. 41B) treatment groups. By the end of the 3-week treatment period, vascularity and permeability were largely confined to the periphery of bumetanide-treated tumors, contrary to that of the control tumors.

DETAILED DESCRIPTION OF THE INVENTION

The present invention relates to a pharmaceutical cocktail and methods of cancer. In particular, one such cocktail comprises a combination of effective amounts of a carbonic anhydrase inhibitor, a member of the hydroxycinnamate class of drugs or a derivative thereof, and/or an angiogenesis inhibitor, including a vascular endothelial growth factor (VEGF) inhibitor such as bevacizumab in combination with blood vessel occlusion. As most cancers in an untreated state uses both aerobic and anaerobic/glycolytic pathways treatments contemplated herein can affect both metabolic pathways.

Although it is not necessary to understand the mechanism of an invention, it is believed that treatments that target the anaerobic and aerobic metabolic pathways more completely deprives cancer of ATP energy production, thereby producing greater damage or killing of cancerous cells. Treatment of the aerobic pathway alone temporarily controls cancer but it induces mutation to a glycolytic form, which does not respond to anti-VEGF or other anti-vascular growth factor agents.

In other embodiments, it relates to compositions and methods of treating cancer involving effective amounts of a member of the hydroxycinnamate class of drugs. Pharmaceutical compositions and methods of treating cancer (eliminating the tumor, shrinking the tumor, prolonging the life of the patient, increasing quality of life by decreasing the grade of adverse events seen with other cancer treatments, and/or preventing/reducing the likelihood of the tumor's metastases) are additional aspects of the present invention. In addition, the present invention may be used to favorably affect the therapeutic result of patients who have not responded to alternative, traditional anti-cancer therapy.

I. Introduction

In recent years, it has become recognized that cancers use both aerobic and glycolytic metabolism [20-22] and that glycolysis may also play a role. The need for vasculogenesis with aerobic metabolism has been well established [23, 24], but the character of vasculogenesis for glycolysis has only recently been described [25]. The traditional vasculogenesis concept explains that hypoxia induces vascular growth factors which support arterial development to supply oxygen [20, 23, 24]. The nature of glycolytic vasculogenesis formulated from the modern literature and data has recently been reported [25].

One vasculogenesis hypothesis, ALPHA (Acidic Lactate sequentially induced Lymphogenesis, PHlebogenesis, and Arteriogenesis) [25], suggests that glycolytic cancers, independent of oxygenation, may produce increased lactate, which stimulate vascular growth factors causing the sequential production of lymphatics, veins and arteries. For cancer to thrive, lactate levels are usually at low or moderate levels which is generally believed to enhance cancerous processes. Glycolytic vasculogenesis enhances the development of drainage vessels to better manage lactate levels.

Figure 1A:
FIG. 1A shows one well defined lesion with increased vascularization in the periphery.
Figure 1B:
FIG. 1B shows progressive growth of multiple larger masses which are hypovascular and hypoxic.

Inconsistencies of the traditional theory are commonly observed in the diagnostic imaging follow-up of cancer patients and those treated with embolization. A seldom recognized inconsistency with the traditional vasculogenesis concept is the evolutionary changes in tumor contrast vascular enhancement over the clinical course of a patient, FIGS. 1A&B. In most patients early small metastatic lesions show considerable enhancement which decreases over time as the tumors grow. Although the arterial enhancement decreases, the tumors continue growth unabated or faster in the hypovascular/hypoxic state. This continued growth and invasiveness of hypoxic tumors has been emphasized in the clinical literature [26, 27].

Figure 2:
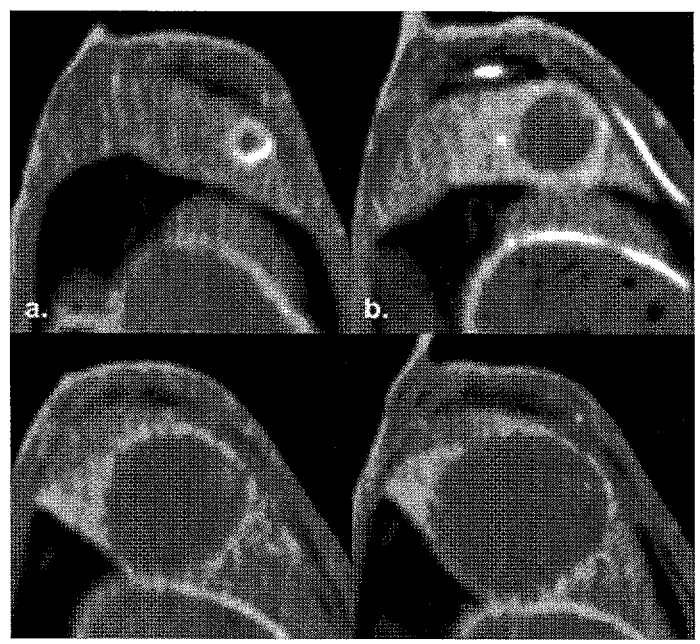
FIG. 2 shows a perfusion study by MDCT at 7, 14, 21, and 28 days.
Figure 3:
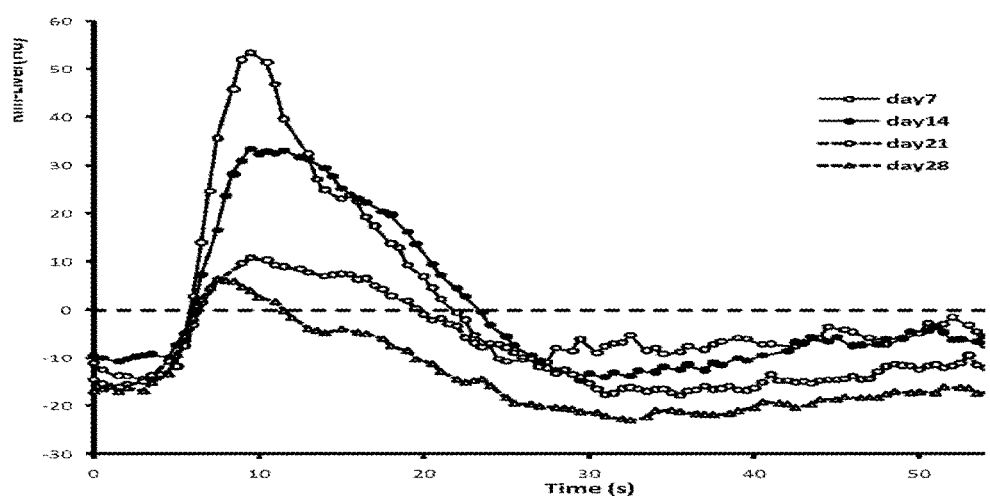
FIG. 3 shows a graph plotting tumor size, X axis, and arterial flow, Y axis, over the 28 day period. The arterial flow is measured in the enhancing rim only. The cancer growth continues unabated, even though arterialization decreases. R correlation=0.373 with p<0.042. With permission of publisher, Wu, Exner, Shi, Bear and Haaga, Dynamic Evolutional Changes in Blood Flow Academic Radiology 2009; 16; 1483-92 [9].

Both the natural evolution and growth of glycolytic tumors and their increased aggressiveness have been documented in the literature. The conversion to glycolysis which sustains rapid tumor growth was confirmed in a long term VX2 liver implant model in rabbits by our group [9]. After tumor implantation, the tumor size and its MDCT perfusion were quantified weekly over a 28 day period. The arterial flow was the greatest at 1 week and decreased subsequently with each weekly examination, FIGS. 2A & B. The TDC (time contrast curves) over the growth period graphically display the evolution from a vascular aerobic tumor to a hypovascular tumor, FIG. 2B. Tumor growth continued unaffected by the progressive decrease in arterial flow. An R correlation between the arterial flow of the enhancing rim with the area of the viable tumor confirmed no correlation=−0.373, p=0.042, see FIG. 3.

Figures 4A, 4B:
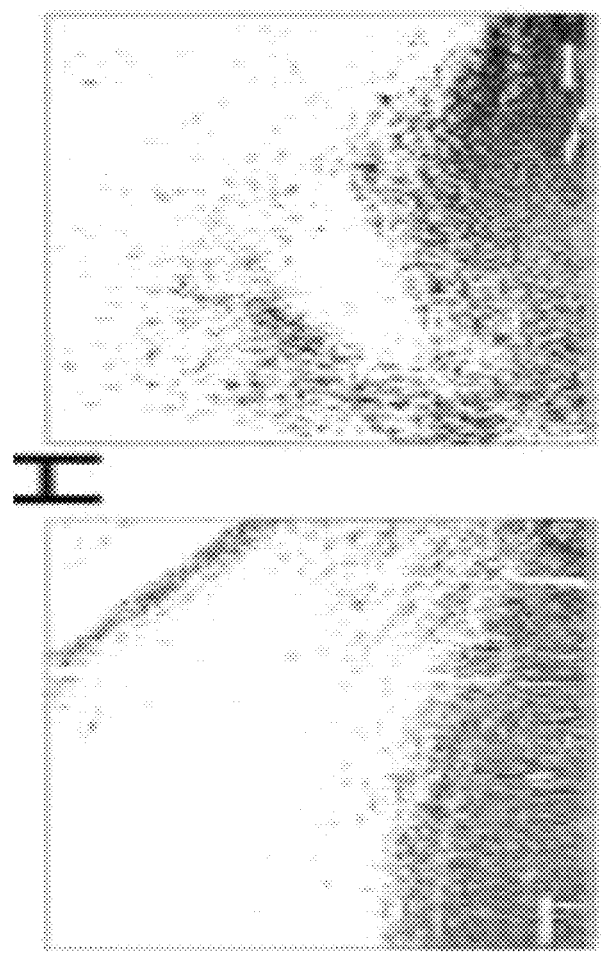
FIG. 4A and FIG. 4B show quantification of the nestin-positive cells outside the tumor core (G and H) shows a 68% increase in cell invasion after treatment from Keunen, O et al, PNAS, Mar. 1, 2011, vol 108, no 9, p 3749-3754 [10].
Figures 5A, 5B:
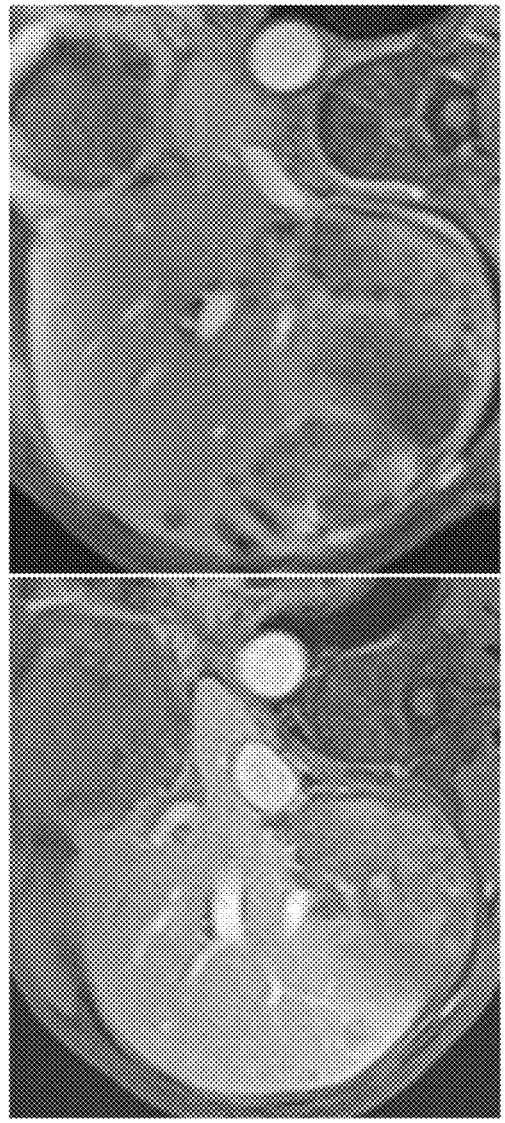
FIG. 5A shows two large masses, one in segment 3 and the second in medial segment 7.
FIG. 5B. Several months later, both lesions have reduced in size but multiple enlarging masses are noted in the lateral part of segment 7 and 8.

When arterial flow is reduced by anti-VEGF drug treatments [10] or arterial embolization [28], cancerous lesions may temporarily recede but can recur as a more aggressive glycolytic form. Keunen et al. who studied a glioblastoma xenograft model treated with anti-VEGF antibodies confirmed that tumors become more aggressive and invasive after hypoxia conversion to a mostly glycolytic tumor, FIG. 4. With hypoxia aerobic cells either die or lose mitochondrial function. Similarly, tumors embolized with particles, even Yttrium may respond initially but can recur with an even more aggressive form, FIG. 5. This continued growth of hypoxic tumors is counter to the traditional concept but modern data explains that glycolysis drives cellular proliferation and tumor growth by abundant energy, building substrates and other advantages, as subsequently described.

Teleological Basis and Tenants of Glycolytic Vasculogenesis

Glycolytic vasculogenesis has numerous tenets, including, but not limited to: 1) Glycolysis produces increased ATP and increased lactate using only glucose without oxygen so arteries are not needed; 2) Glycolysis with lactate production is the preferred metabolic pathway at all oxygenation levels, because it modulates many advantageous processes which support cancer; 3) Excessive high lactate levels impairs or stops glycolysis, which cause cells to lapse into cellular arrest; 4) To restore cell growth, proliferation and pro-cancer advantages, excessive lactate levels must be reduced to favorable levels by lymphatics and veins; 5) Lactate increases the vascular growth factors and other mechanisms for initiating vasculogenesis which complements and supplements traditional vasculogenesis; and. 6) To give lactate drainage priority, the sequence of vessel development is lymphatics first, veins, and then arteries.

Glycolysis Produces Increased ATP and Increased Lactate Using Only Glucose without Oxygen, so Arteries are not Needed.

Considering the chemical reactions of oxidative phosphorylation and glycolysis, the types of vessels needed for each process become quite clear. Aerobic metabolism very efficiently uses its substrates, oxygen and glucose, to make large amounts of ATP energy: 1 glucose molecule and 1 oxygen molecule make 38 ATP's with 2 $CO_2$. In contrast, glycolysis uses 19 glucose molecules without oxygen to produce the equivalent 38 ATP's with 38 lactates. Arteries for oxygen or glucose are not needed but drainage vessels are (predominantly) lymphatics to clear lactate.

Figure 6:
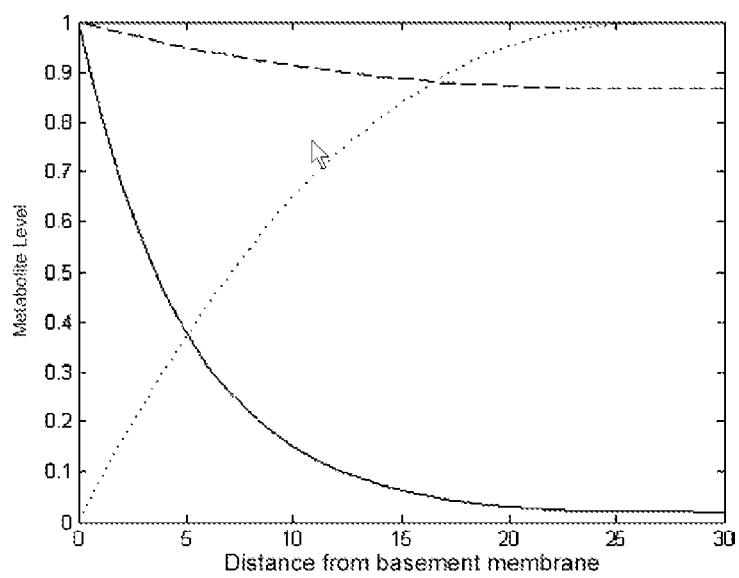
FIG. 6 shows substrate and metabolic profiles found in premalignant intraductal tumor using reaction-diffusion modeling. Oxygen concentrations (solid line), glucose concentrations (dashed line), and H+ concentrations (dotted line) are shown. Graph shows that as the distance from artery supply to cells increase oxygen (solid line) levels drop because of poor diffusion. Glucose levels (dashed line) remain constant because glucose diffuses well and is actively transported. With permission of the publisher, Gillies and Gatenby, (2007) *J. Bioenerg. Biomembr.* 39:251-257 [11].
Figure 7B:
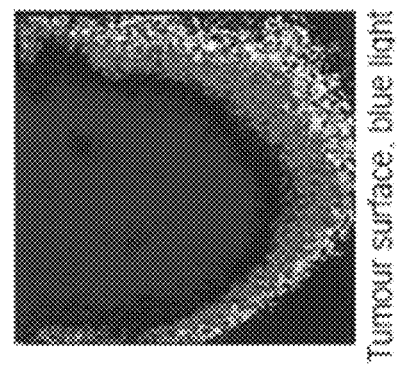
FIG. 7A shows autogradiography of FDG in a tumor mass. The very highest concentration of the FDG is centrally where the hypoxia is greatest and the GLUT transporters are the highest, Zhao, S, Kuge, Y, Mochizuki, T, et al, (2005), *J. Nucl Med,* 46(5); 675-682 [12], FIG. 7B. Fluorescent oxygen imaging of tumor in transparent window model shows oxygenation in the periphery but severe hypoxia centrally, Dewhirst et al, (1999), British Journal of Cancer 79(11/12); 1717-1722 [13].
Figure 7A:
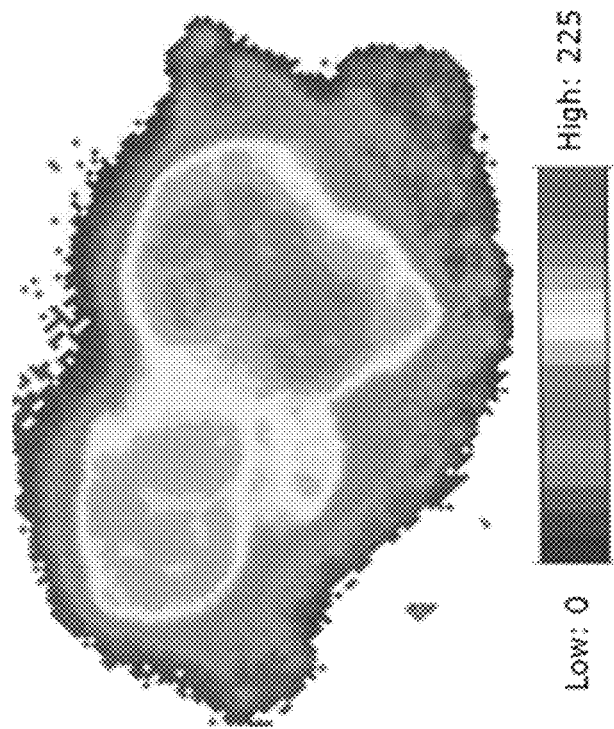

Abundant arterial supply is necessary for oxygen transport but not for glucose supply. Oxygen diffuses poorly over distance however glucose diffuses quite well and has specialized glucose transporters (GLUTS), FIG. 6. Even if the center of a mass has poor arterial flow and is hypoxic there is always abundant glucose in the deepest part of the tumor, FIG. 7. This has been confirmed by comparison studies between clinical radionuclide blood flow and FDG PET studies. These show there is no correlation between arterial flow/oxygenation and FDG uptake [29] which confirms abundant glucose if available for glycolysis without significant arterial flow.

Some suggest that cancer cells prefer oxidative phosphorylation because it is so chemically efficient (38 ATP per glucose), but glycolysis provides advantages which supersede this efficiency. While glycolysis is not as efficient in its use of glucose, it more than compensates to provide abundant energy by way of its very rapid reaction speed. Glycolysis produces ATP energy 100 times faster than aerobic metabolism, because it has fewer reactions and two feed forward catalytic steps [25].

Glycolysis with Lactate Production is the Preferred Metabolic Pathway for Cancer at all Oxygenation Levels Because it Provides Many Advantages for Cancer.

For example, such cancer advantages may include but is not limited to the production of building substrates for cellular growth and the initiation and support of many pro-cancer processes.

The role of glycolysis for providing building substrates for cell growth and proliferation has been reported [30, 31]. The essential proteins, lipids, nucleotides, etc. are produced by numerous side reactions related to glycolysis. Before cell proliferation can occur, mother cells must double their biomass before division to ensure that each daughter cell is fully endowed with the necessary cellular components, such as DNA, RNA, cell membranes, organelles etc. Without such growth, cell division cannot proceed and cells lapse into cellular arrest or quiescence.

Figure 8:
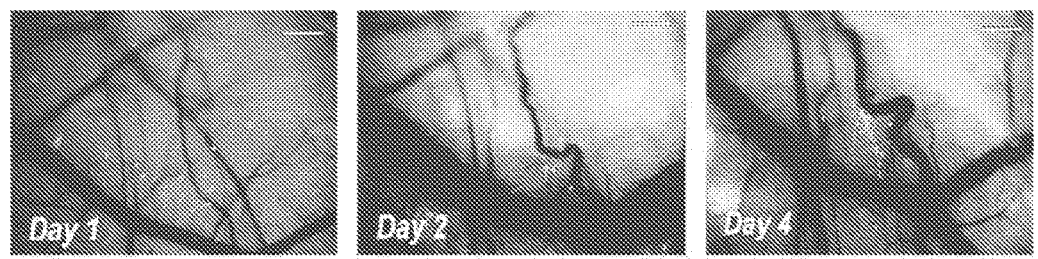
FIG. 8 shows growth of a tumor from single 4T1 cells in a BALB/c mouse window chamber. Approximately 20 cells were injected in a BALB/c mouse window chamber, and their growth was followed serially after the initial implantation. Note that both processes (i.e. growth and angiogenesis) were visible at the approximately 20- to 50-cell stage of tumor growth. before the $10^5$ cell number which is the threshold for hypoxia. Accordingly, the vasculogenesis is likely due to increased lactate from cancer cells. The cancer cells with fluorescent green show motility and move between days 1, 2, and 4. Such cell movement also depends on lactate, which activates the motogenic genes [14, 15].
Figure 9:
FIG. 9 shows a CT scan revealing breast cancer in medial portion of right breast, vertical arrow, and an enlarged lymph node seen in lateral portion of breast, horizontal arrow. Spread to lymph nodes is enhanced by increased fluid flow, but, also, the ameboid movement of cancer cells. Cell movement depends upon lactate's induction of the molecular hyaluronan, which activates the motogenic genes [15].

The lactate produced by glycolysis is generally considered a "waste product", but in fact it has variable roles and modulatory effects at different concentrations, which are beneficial to cancer cells. At low concentrations, lactate is a high energy substrate which can be used by adjacent aerobic normal or cancerous cells [32, 33]. At moderate concentrations, lactate initiates many processes which support cancerous activities: a) lactate creates a hostile low pH/high lactate selective environment, which kills normal or unadapted cancer cells but selective adapted cancer cells have special waste management (Carbonic anhydrase IX and lactate transporter MCT4) survive [11, 14, 34]. These enzymes are believed to protect the surviving aggressive cancerous phenotypes. b) low pH and lactate initiates transformation of the microenvironment by activating metalloprotease enzymes, which alters tissue structure and releases and activates biomarkers [11, 15]. c) lactate initiates cancer cell motility through an intermediate, molecule, hyaluronan, which turns on the motogenic genes [15, 35], Such movement facilitates local cell invasion or lymph node metastases, see FIG. 8 and FIG. 9, b) increased lactate levels impair the local host immune cells, so that lymphocytes, natural killer cells, dendritic, and macrophages cannot proliferate, recognize antigens, nor produce cytotoxic cytokines [25, 36]. e) cancer cells, incubating in lactate and ketones from glycolysis, transform into a stem cell like state capable of unlimited mutations [37]. f) molecules are induced by lactate, which are anti-apoptotic [38-41]. g) lactate, independent of oxygenation, increases HIF1a, a very important modulator for cancer proteins and enzymes [25, 42-46]. h) finally lactate directly and indirectly stimulates different cells and processes which produce vascular growth factors (VEGF, FGF, VEGFC, etc) for vasculogenesis [45-55]. This production occurs at all oxygenation states (normoxia, hypoxia, or hyperbaric oxygen), so lactate complements and supplements the traditional hypoxic vasculogenesis.

High Lactate Levels Impairs Cancer Growth Because it Causes Cellular Quiescence or Arrest.

Figure 10:
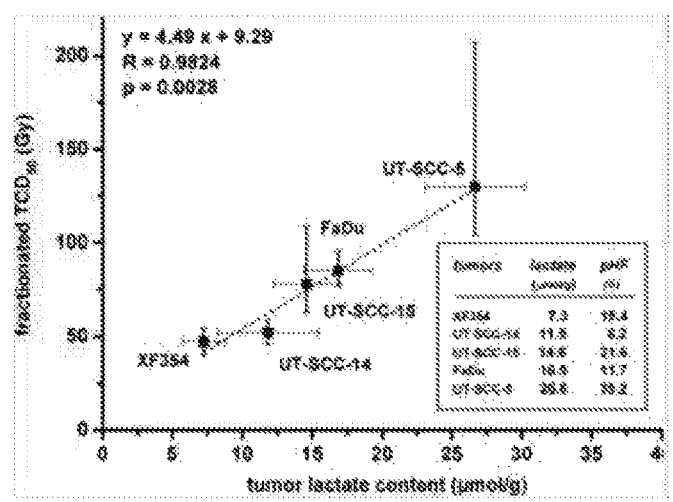
FIG. 10 shows a correlation of radioresistance to high lactate levels.

High lactate levels and the associated low pH can impair or stop glycolysis, which precludes the benefits described above. This cessation of glycolysis occurs because of basic chemical principles. The low pH caused by lactate stops glycolysis at the rate limiting enzyme phosphofructose kinase. Further, high lactate inhibits glycolysis by end product inhibition or "negative feedback" [56-60]. With the loss of the abundant building substrates and increased ATP needed for cell growth and division, cell proliferation is reduced or ceases. Non-growing mother cells lapse into cellular quiescence or arrest [30, 31]. Sattler and Quennet [61, 62] reported that increased lactate directly correlates with radioresistance. Quennet found the correlation of radioresistance to high lactate levels was R=0.9824, p+0.0028, FIG. 10. The causes of radioresistances have not been elucidated but likely cellular arrest and anti-apoptotic processes [38-40, 55] contribute to radioresistance.

To prevent excessively increased lactate which can retard cell growth, proliferation, and pro-cancer advantages, lymphatics and veins are needed to clear lactate [61, 62] to maintain optimal lactate levels. Lymphatic vessels may drain lactate laden extracellular interstitial fluid [63]. Rutz asserted that lactate from glycolysis is a factor causing increased interstial fluid [64]. When cancer cells make excess lactate it is transported through the cell membrane into the interstitial space. The exported lactate makes the interstitial fluid hypertonic, which causes the influx of free water increasing the interstitial fluid pressure and subsequent flow. A recent de novo skin cancer model reported by Eitchen [16] emphasized that lymphatic development may occur when cells make the transition from a premalignant state to carcinoma in situ. They observed that lymphatics are normal sized in the premalignant phase but when carcinoma in situ and locally invasive progresses, the normal lymphatics dilate with increased fluid flow and rapid proliferation of lymphatic endothelial cells.

Figure 11:
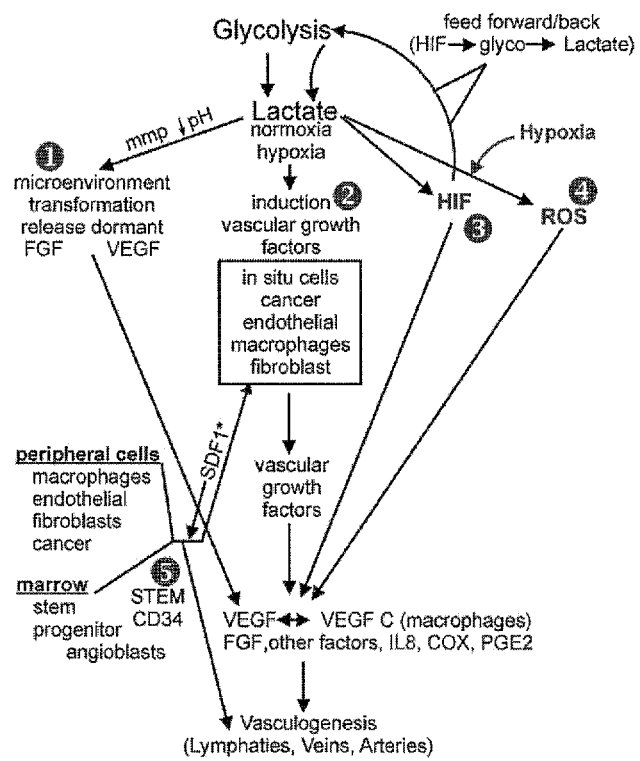
FIG. 11 shows a flow chart demonstrating the five mechanisms by which lactate initiates vasculogenesis: 1) microenvironment release of FGF and VEGF 2) induction from in situ and chemoattracted cells 3) production of HIF1a by the effects of lactate on multiple mechanisms. Both lactate and hypoxia increase HIF (which regulates VEGF, etc.) by decreasing the HIF's degradation enzyme PhD (prolyl hydroxylase 4) ROS reactive oxygen species produced by both lactate and hypoxia increases VEGF 5) stem cell chemo attraction of the unique CD34+133+VEGFR3+ cells. These mechanisms for lactate function at all oxygenation levels normoxia, hypoxia, or hyperbaric. There is even a feed forward mechanism for lactate to HIF to glycolysis to lactate, etc.

Lactate increases vascular growth factors [45-55] and causes chemoattraction of key cells important for vasculogenesis [65-67]. Increase of vascular growth factors by lactate comes from multiple processes, FIG. 11, including the release of dormantly stored factors in the extracellular matrix, non HIF induction of growth factors from many cells and increased HIF1a, (hypoxia induction factor). There are two additional independent vasculogenic pathways, ROS (reactive oxygen species) and stem cell angiogenesis which are stimulated by lactate.

The initial increase of factors are FGF (fibroblast growth factors) and VEGF (vascular endothelial growth factor) which are released from their dormant form in the extracellular matrix [17, 47, 48]. These are released when low pH and lactate activate metalloproteases which degrade and transform the microenvironment [15, 34]. The disruption of the existing matrix and collagen facilitates cellular movement and vasculogenesis. Additional production of vascular growth factors is stimulated by lactate from in situ cells and chemoattracted cells (cancer cells, fibroblasts, endothelial cells and macrophages). The chemoattractant SDF-1 (stromal derived factor-1) for these cells is produced by lactate via HIF1a (Hypoxia Induction Factor) as an intermediary [46].

Figure 12:
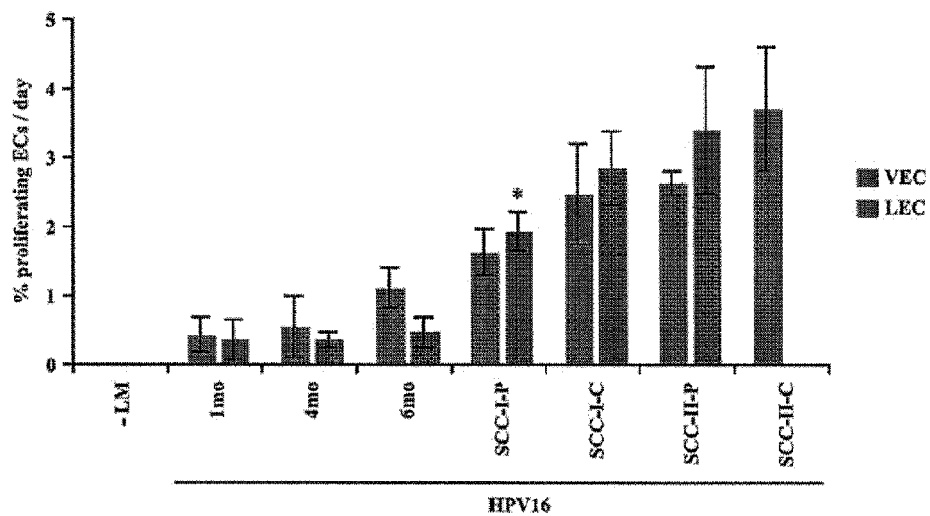
FIG. 12 shows the rate of lymphatic endothelial cell proliferation is greater than that of vascular endothelial cells during the transition into the malignant form (SCC-I-P, SCC-I-C, SCC-II-P). VEC and LEC proliferation in premalignant and carcinoma tissue. Quantitative analysis of proliferating VECs and LECs in -LM, premalignant and carcinoma tissue. Proliferating LECs were identified in the periphery and center of well-differentiated grade 1 SCCs (SCC-I) but limited to periphery of less-differentiated grade 2 SCCs. Absence of open lumen lymphatic vessels SCC-II centers precluded analysis of LECs in that locale. *, P≤0.05, two-tailed unpaired nonparametric Mann-Whitney U, (2007) *Cancer Res,* 67(11): 5211-20 [16].

More vascular growth factors are made by these cells by the action of HIF1a, which is a modulator of VEGF and/or glycolysis. HIF1a is stimulated by hypoxia but it is also produced in greater amounts by lactate through multiple mechanisms [25, 42-46]. Both hypoxia and increased lactate increase HIF by reducing its degradation enzyme PhD (prolyl hydroxylase), FIG. 12. When PhD decreases, the levels of HIF rise because less HIF is destroyed. The lactate mechanisms are more significant than hypoxia because lactate increases HIF in normoxia, hypoxia and hyperoxia [25, 42-46]. Further, greater amounts of HIF are made by lactate because it causes a "feed forward" reaction, which can be self perpetuating. When lactate increases HIF1a, glycolytic enzymes are increased which increases lactate [43] which increases HIF, etc.

The two other lactate related mechanisms which may increase vasculogenesis are ROS (reactive oxygen species) [45] and the chemoattraction of marrow progenitor stem cells [66, 67].

The attracted stem cells have two separate roles, assisting existing vessel morphogenesis and initiating an additional independent pathway. Unspecified angioblasts assist with morphogenesis of existing vessels by aiding the "budding" and channel formation. The specific character of the vessel formed (i.e., for example, lymphatic, veins, and/or arteries) is determined by the interaction of different biomarkers (i.e., for example, PI3K and Ephrin B4 for veins; Notch and Ephrin B2 for arteries).

The unique stem cell CD34+, 133+ with VEGFR3+, which is a lymphatic endothelial cell precursor has a remarkably unique role. Although the mechanism has not yet been defined, this cell through VEGFC and Wnt/respondin pathways can initiate vasculogenesis in and of itself without other processes [66, 67].

To give lactate drainage priority, the essential growth factors VEGFA and FGF2 produce vessel development with lymphatics first, veins, and then arteries. To appreciate the numerous reports on vessel development it is important to understand the important role of VEGFA and FGF2 for starting the initial angiogenic burst which results in sustained vasculogenesis [68-70]. The recent report by Indraccolla et al [68] confirmed that a transient angiogenic burst caused by VEGFA and FGF2 within the transformed microenvironment starts the entire vasculogenesis process.

The VEGFA molecule was originally named VPF (vascular permeability factor), because it controls vascular permeability but the name was changed after synthesis of the VEGFA molecule and introduction of anti-VEGF antibodies [18, 71]. The receptor for VEGFA(VPF) and permeability occur in veins, not arteries [71-73] as proven by immunohistochemistry, electron microscopy, radionuclide and macromolecule diffusion. Since the primary receptor sites aren't arterial it is logical that hypoxia caused by anti-VEGF drugs occurs by means of venous infarction. If veins are closed, arterial flow ceases.

The sequence of vessel morphogenesis (lymph, veins, arteries) has been confirmed by many different models (de novo spontaneous squamous cell cancer model, xenograft implants. FGF growth factor pellet implants; and VEGF gene transfection).

In a de novo skin cancer model [16], lymphatic cells proliferated and enlarged existing lymphatics before blood vessel changes. This occurred when the tumor changed from premalignant to malignant occurred. After the tumor became larger and more invasive, blood vessel endothelial cells proliferated FIG. 12.

Figure 13:
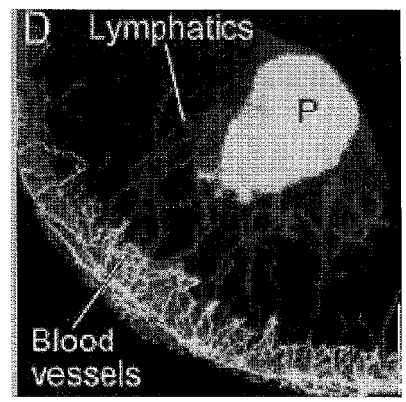
FIG. 13 shows FGF-2 stimulates corneal lymphangiogenesis. Lowering the dose of the FGF2 pellet to 12.5 ng (P) and moving it farther from the limbus results in less angiogenesis, although lymphatic vessels still reach the pellet, Chang et al, (2004) *Proc Natl Acad Sci USA*. 101(32): 11658-11663 [17].

Chang et al [17] characterized the types of vessels morphed by implanted FGF2 pellets, see FIG. 13. At low concentrations, FGFb induced lymphatics via VEGFC and D without hemangiogenesis. Higher concentrations of FGFb equally stimulated both lymphatics and blood vessels via VEGFA. VEGFA came from attracted macrophages and released from the extracellular matrix [17, 34, 47, 48]. VEGFC and D for lymphatics came from attracted macrophages [17].

Figure 14:
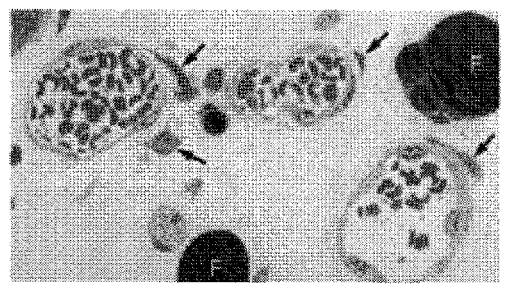
FIG. 14 shows three different mother veins at different stages of dilation. The center cell shows very early separation of pericyte from wall. The vein to the right shows some dissolution of the basement membrane and minimal separate of the pericyte. The vein on the left shows degradation of the basement membrane and complete separation of the pericytes. Reproduced with permission of publisher, Pettersson, et al. (2000) *Lab Invest* 80:99-115 [18].
Figure 15:
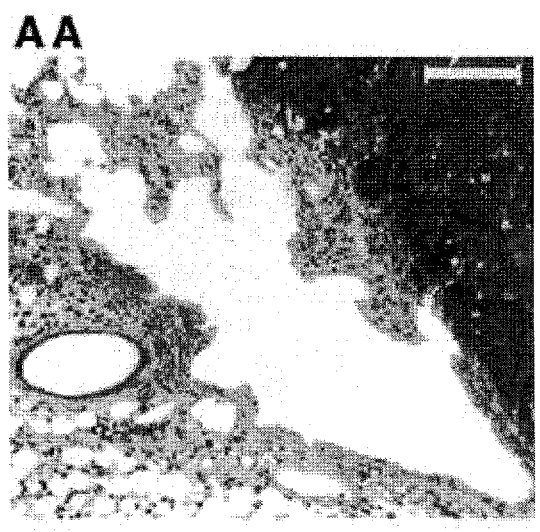
FIG. 15 shows microdissection from Patan et al., showing large ecstatic host venule with intussception and in the process of dividing into multiple veins, Patan, S et al. (2001) *Circ Res*. 89:732-739 [19].
Figure 16:
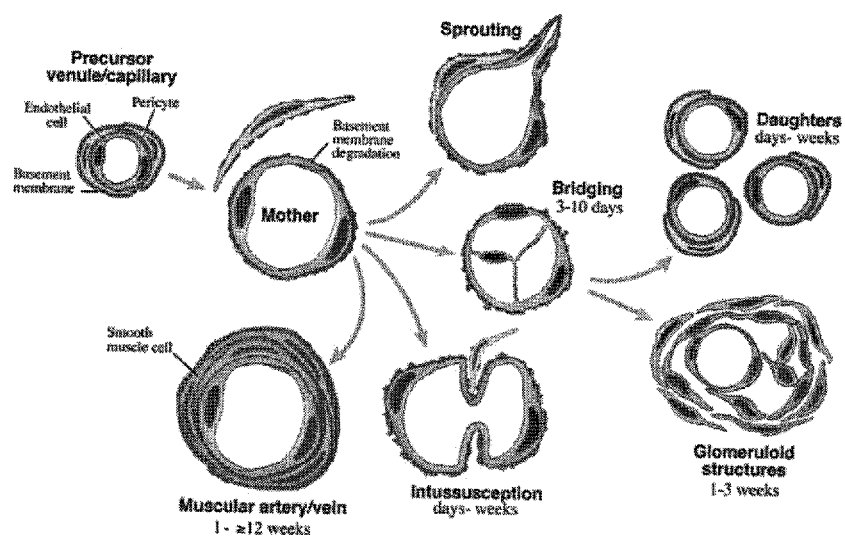
FIG. 16 shows a schematic diagram summarizing the progression of the angiogenic response that follows introduction of aden-vpf/vegf into adult tissues of immunodeficient mice and rats. The host venule changes into a mother vessel by degradation of the basement membrane and detachment of the pericytes. From this state the vein may sprout or develop endothelial bridging created multiple channels which form multiple small daughter veins. Muscular fibers may develop to become artery/vein over weeks. The glomerulid structure is a transient entity, Pettersson et al. (2000) *Lab Invest,* 80:99-115 [18].
Figure 17:
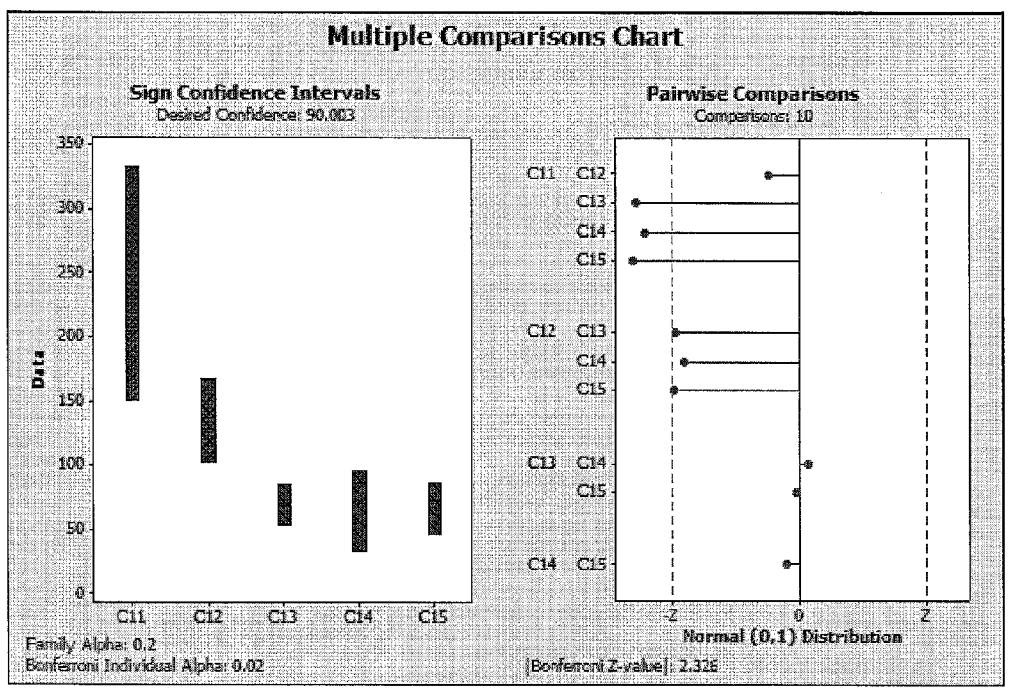
FIG. 17 shows 0.5 week c11, Control; c12, TAE; c13, Bumex (Bumetanide); c14, ferulic acid; c15, caffeic acid.
Figure 18:
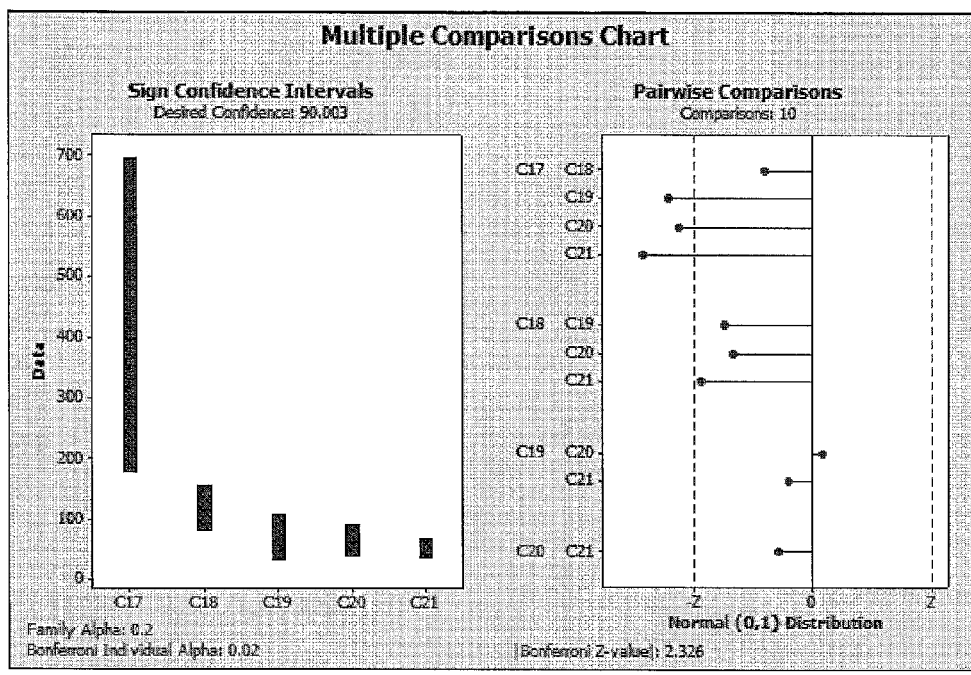
FIG. 18 shows 1 week: c17, Control; c18, TAE; c19, Bumex (Bumetanide); c20, ferulic acid; c21, caffeic acid.
Figure 19:
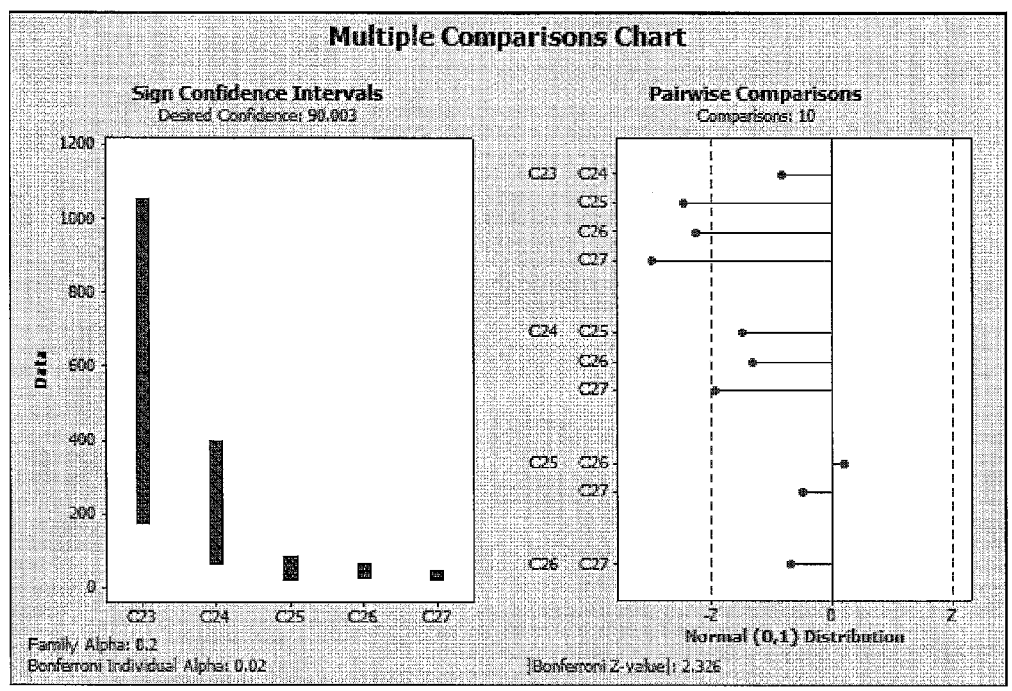
FIG. 19 shows 1.5 Week: c23, Control; c24, TAE; c25, Bumex (Bumetanide); c26, ferulic acid; c27, caffeic acid.
Figure 20:
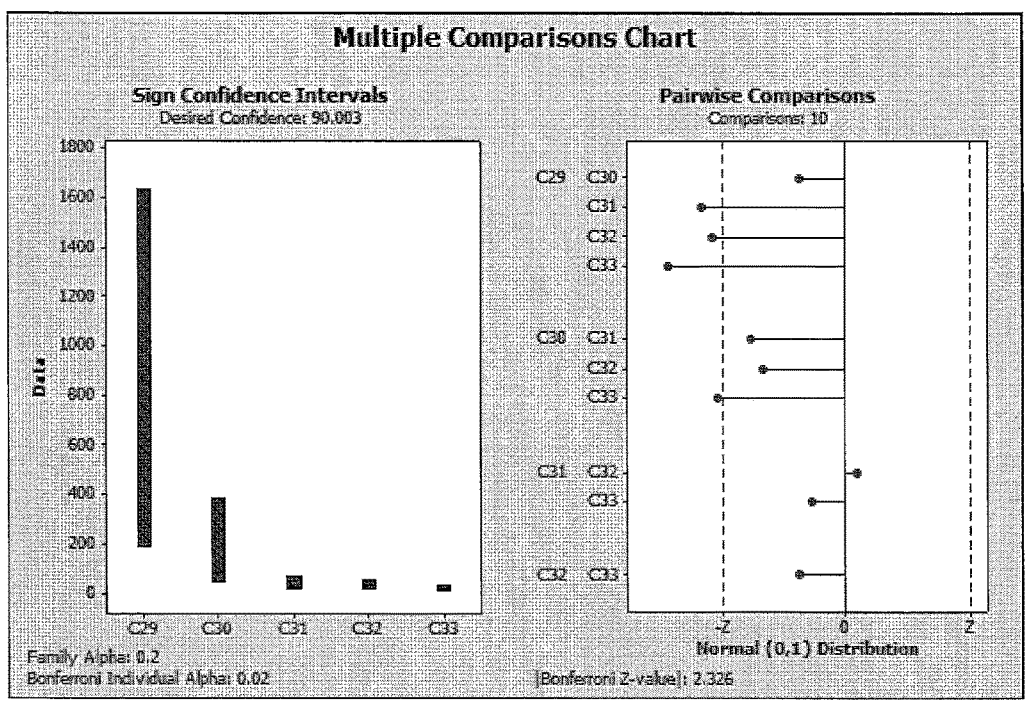
FIG. 20 shows 2 Week: c29, Control; c30, TAE; c31, Bumex (Bumetanide); c32, ferulic acid; c33, caffeic acid.
Figure 21:
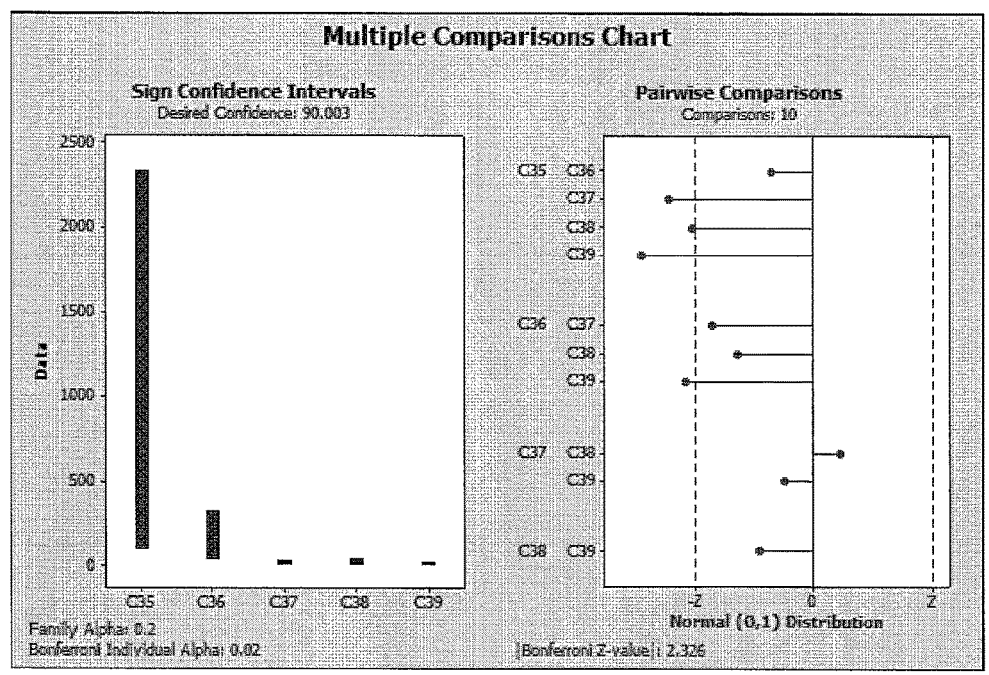
FIG. 21 shows 2.5 Week: c35, Control; c36, TAE; c37, Bumex (Bumetanide); c38, ferulic acid; c39, caffeic acid.
Figure 22:
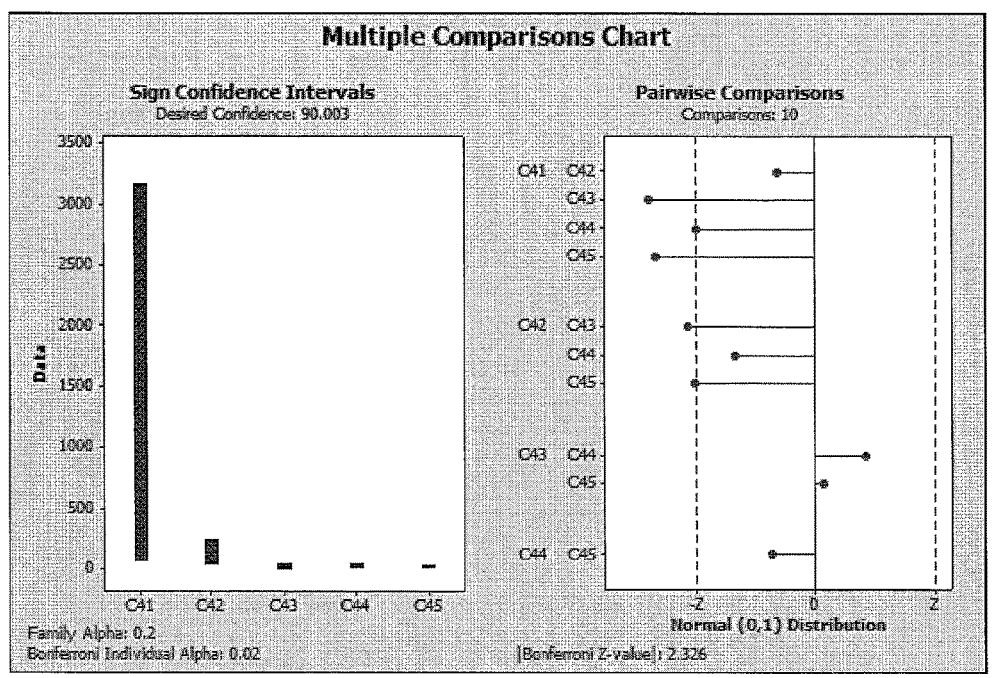
FIG. 22 shows 3 Week: c41, Control; c42, TAE; c43, Bumex (Bumetanide); c44, ferulic acid; c45, caffeic acid.
Figure 23:
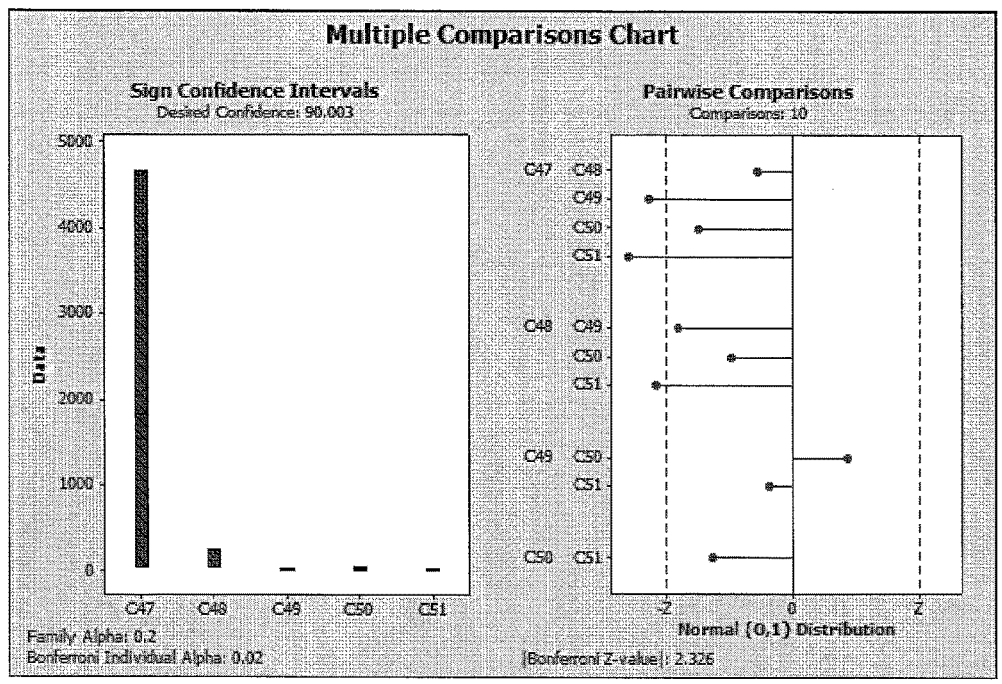
FIG. 23 shows 3.5 Week: c47, Control; c48, TAE; c49, Bumex (Bumetanide); c50, ferulic acid; c51, caffeic acid.
Figure 24:
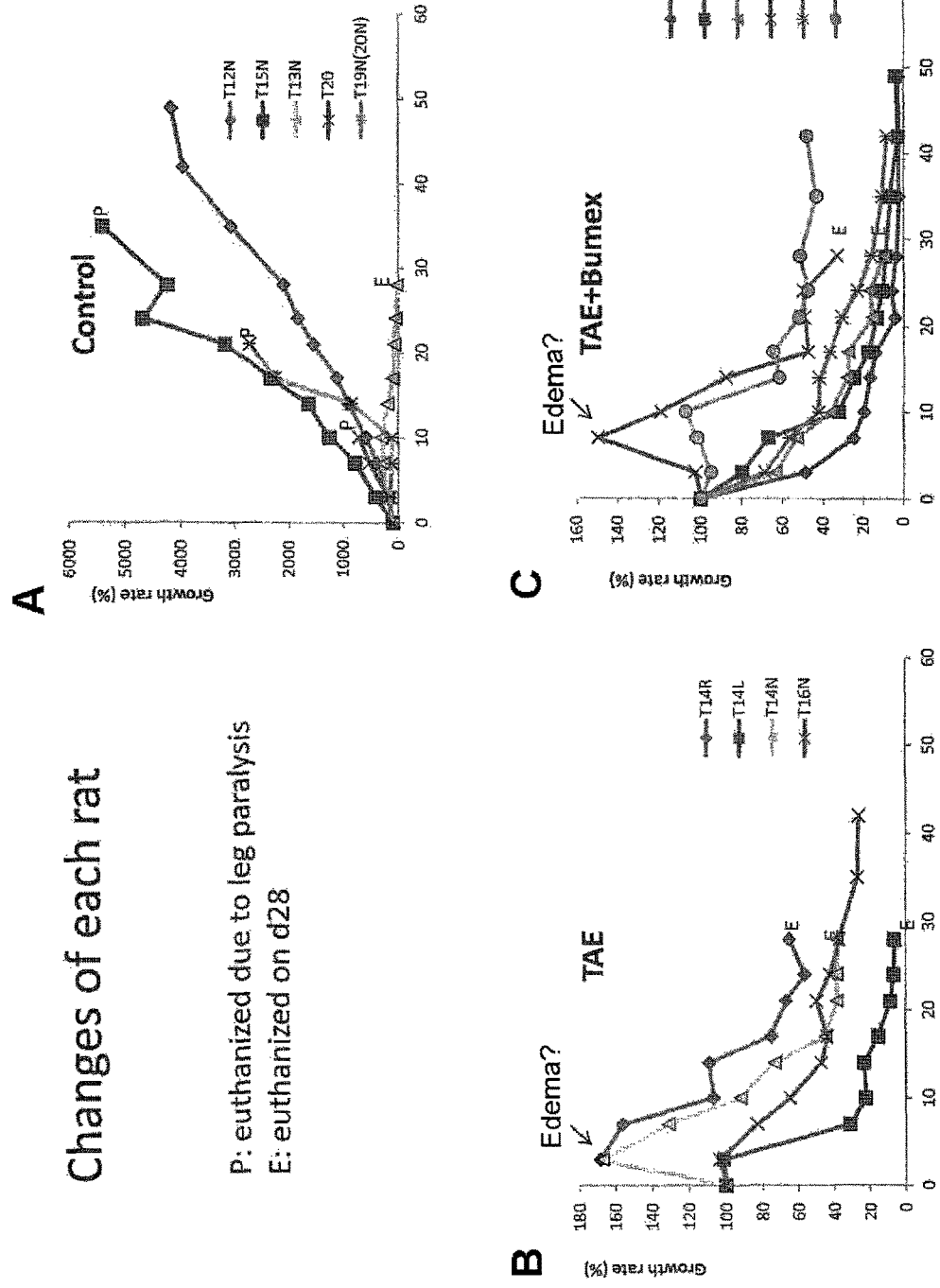
FIG. 24A-C show the changes of each rat under different conditions.
Figure 25:
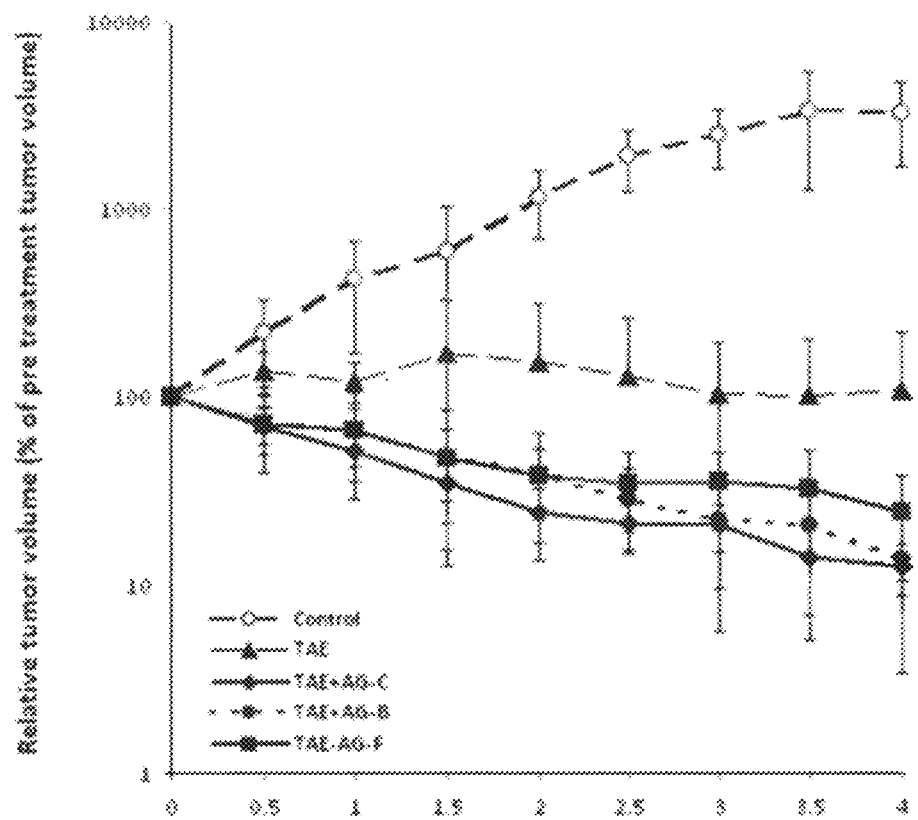
FIG. 25 shows the relative tumor volume comparing the different treatments over four weeks. Bumex (Bumetanide), ferulic acid, and caffeic acid proved effective at reducing tumor volume in the mouse leg tumor model.
Figure 26:
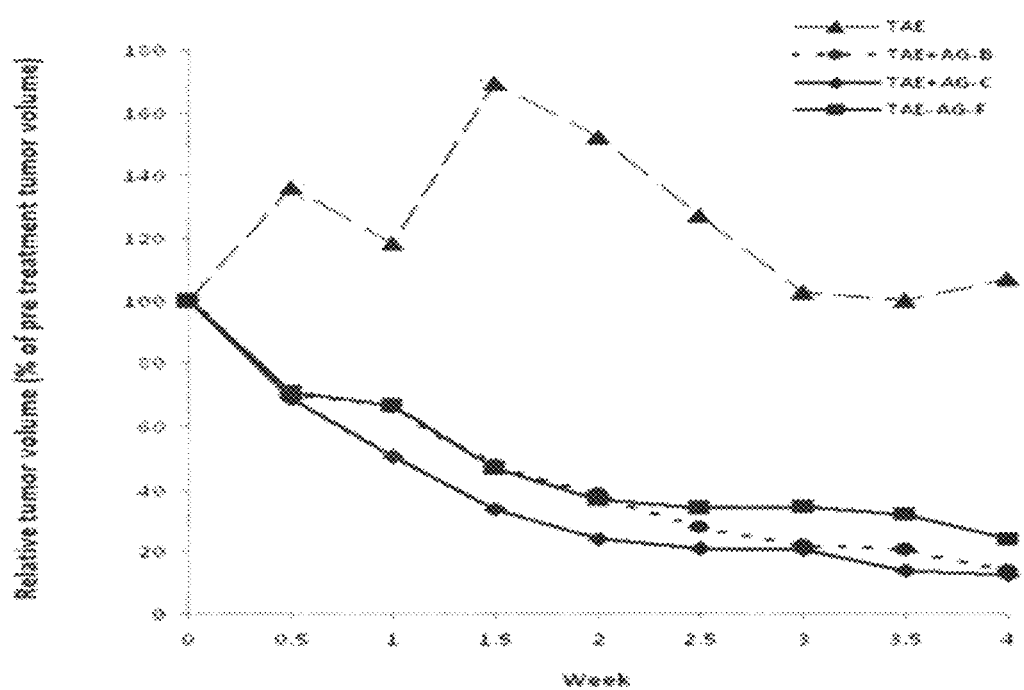
FIG. 26 show a graph comparing tumor volume versus time for control, TAE, and TAE+three antiglycolytic agents.
Figure 27:
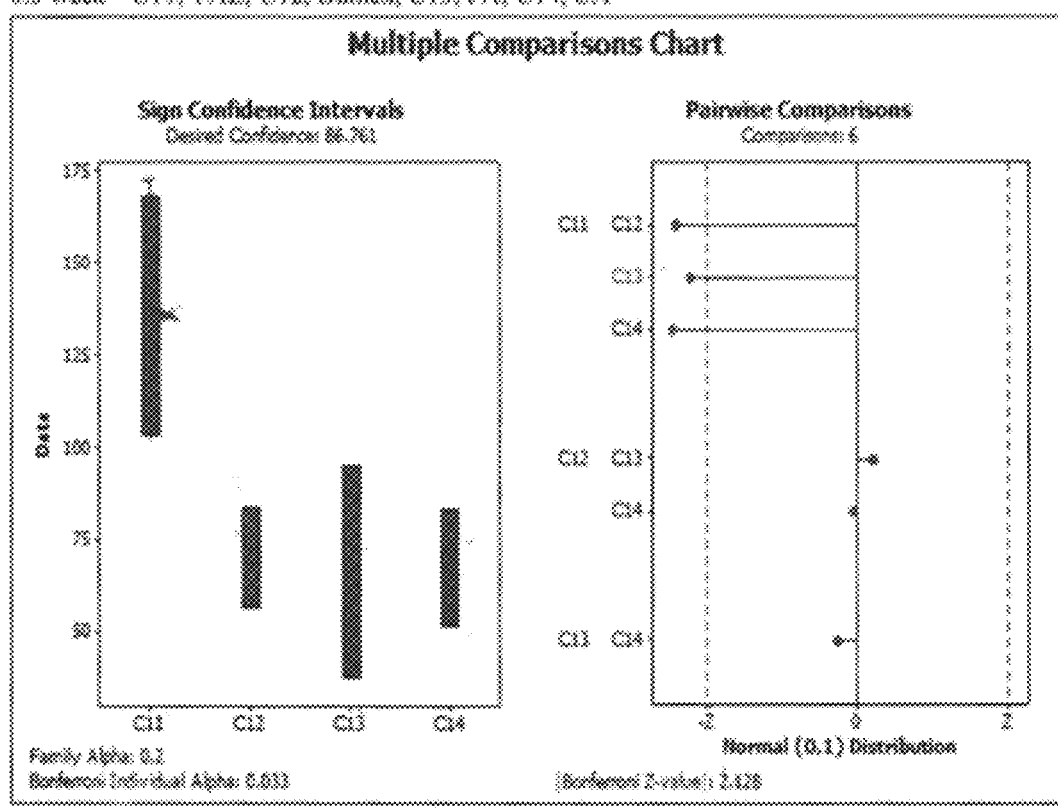
FIG. 27 shows the results at 0.5 week for different treatments of tumors: c11, TAE; c12, Bumex (Bumetanide); c13, ferulic acid; c14, caffeic acid.
Figure 28:
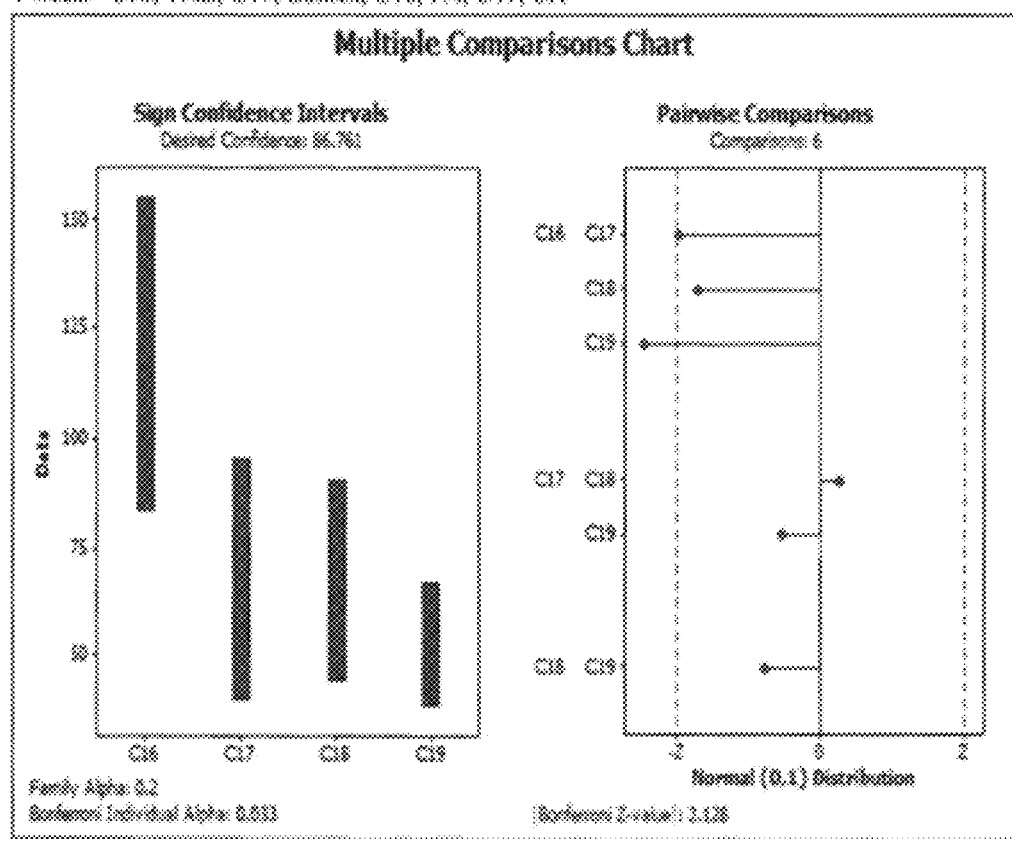
FIG. 28 shows the results at 1 week for different treatments of tumors: c16, TAE; c17, Bumex (Bumetanide); c18, ferulic acid; c19, caffeic acid.
Figure 29:
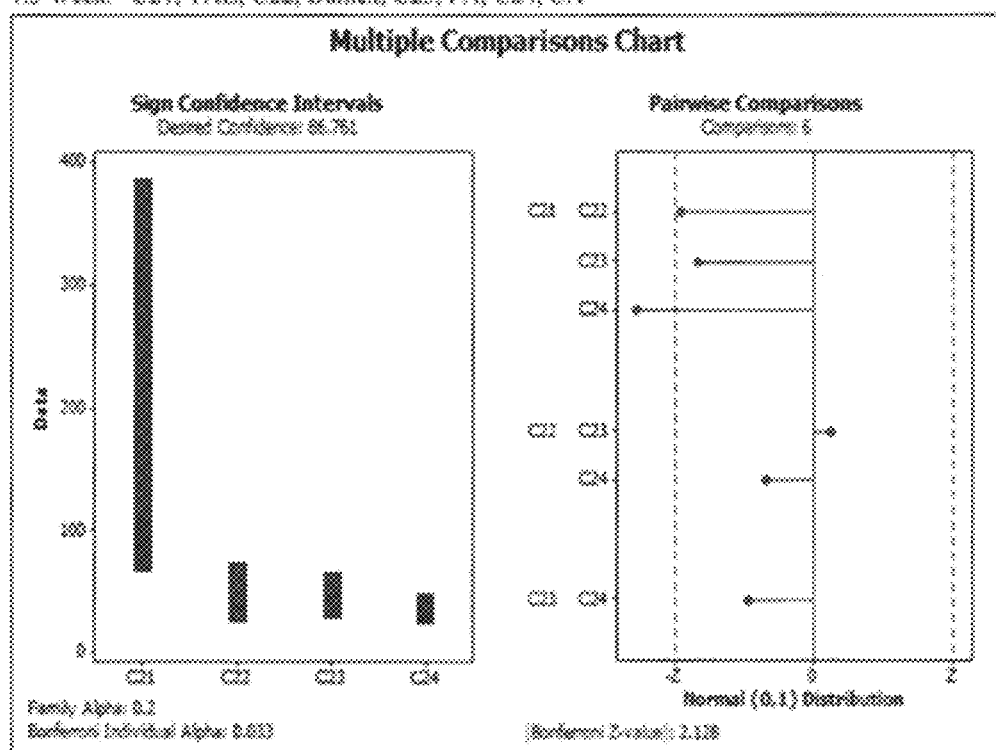
FIG. 29 shows the results at 1.5 weeks for different treatments of tumors: c21, TAE; c22, Bumex (Bumetanide); c23, ferulic acid; c24, caffeic acid.
Figure 30:
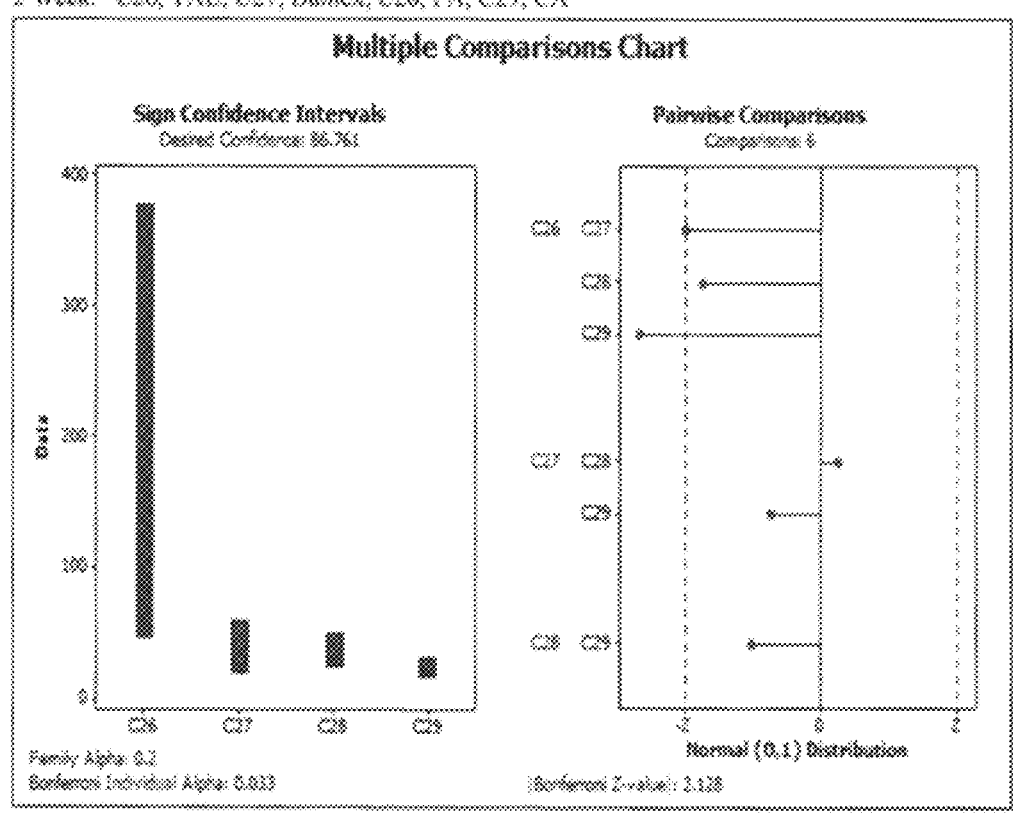
FIG. 30 shows the results at 2.0 weeks for different treatments of tumors: c26, TAE; c27, Bumex (Bumetanide); c28, ferulic acid; c29, caffeic acid.
Figure 31:
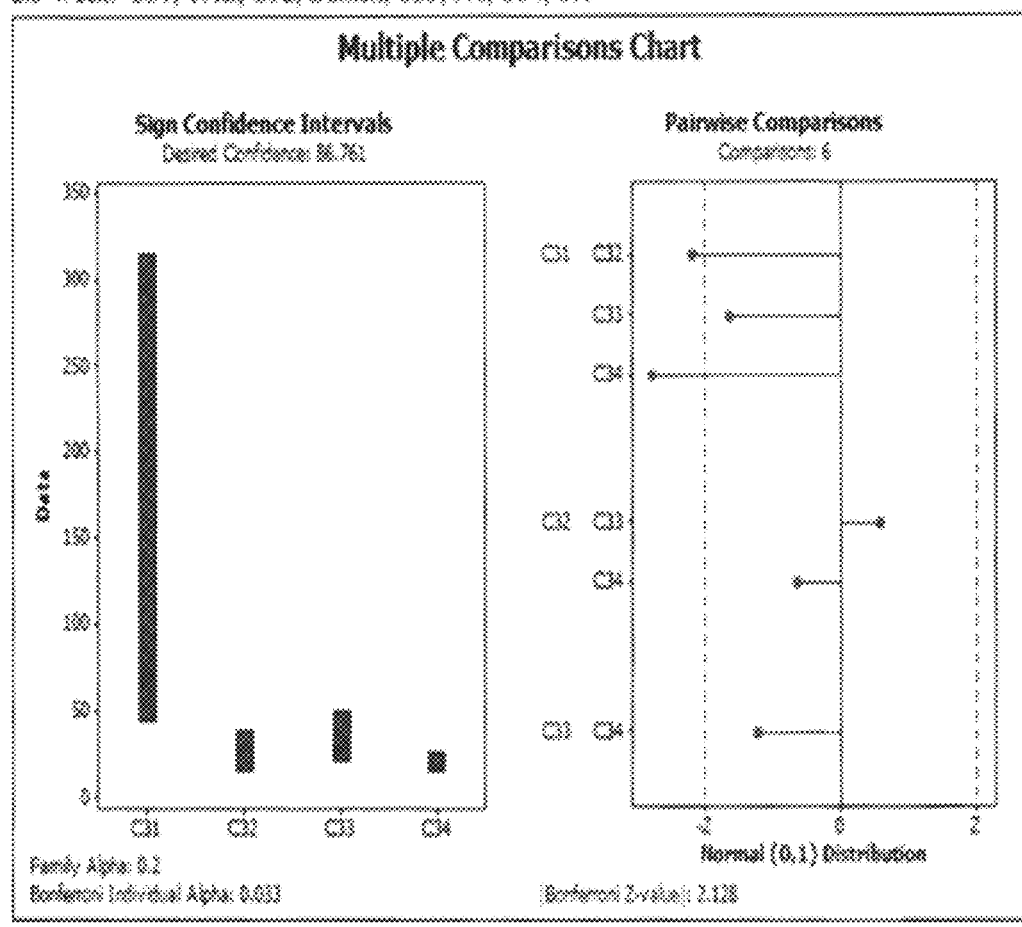
FIG. 31 shows the results at 2.5 weeks for different treatments of tumors: c31, TAE; c32, Bumex (Bumetanide); c33, ferulic acid; c34, caffeic acid.
Figure 32:
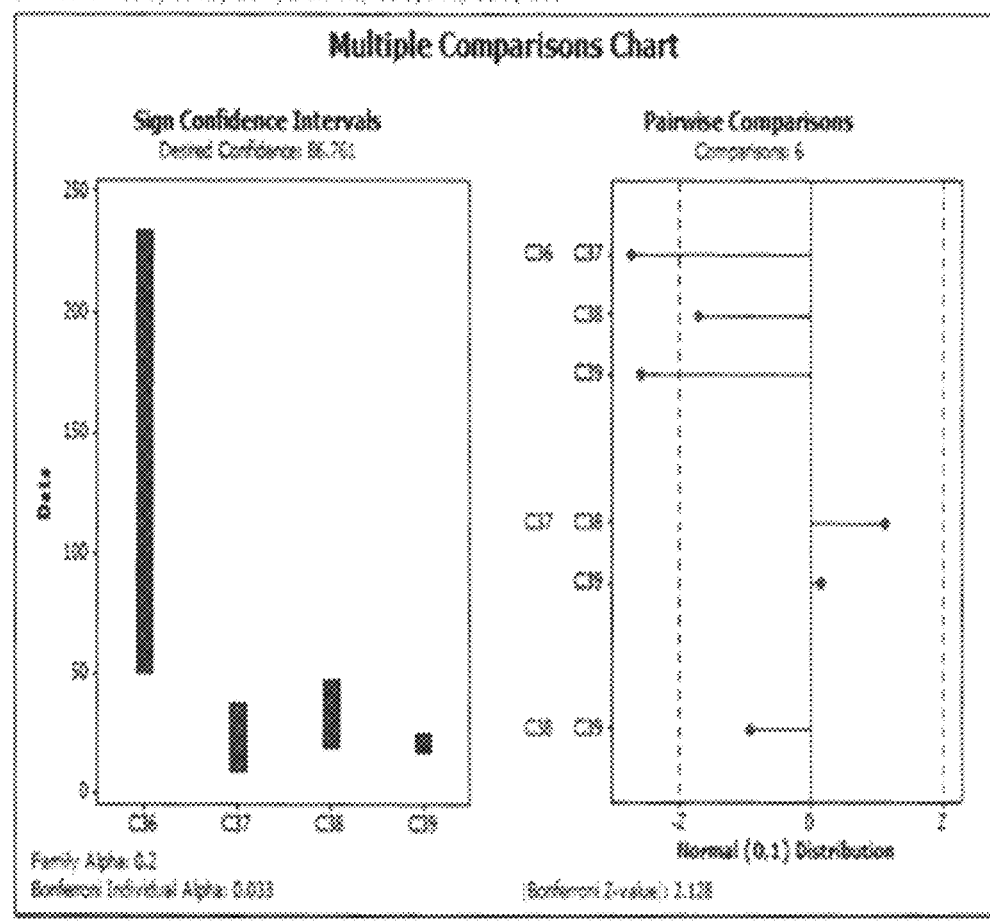
FIG. 32 shows the results at 3.0 weeks for different treatments of tumors: c36, TAE; c37, Bumex (Bumetanide); c38, ferulic acid; c39, caffeic acid.
Figure 33:
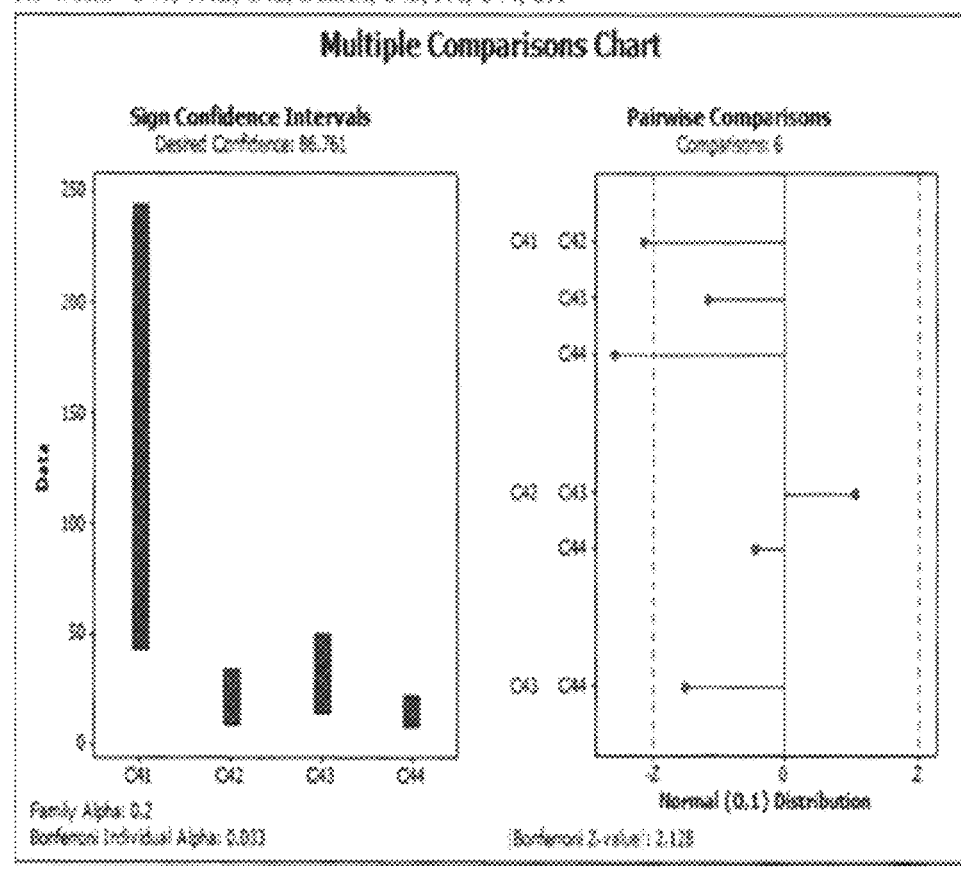
FIG. 33 shows the results at 3.5 weeks for different treatments of tumors: c41, TAE; c42, Bumex (Bumetanide); c43, ferulic acid; c44, caffeic acid.
Figure 34:
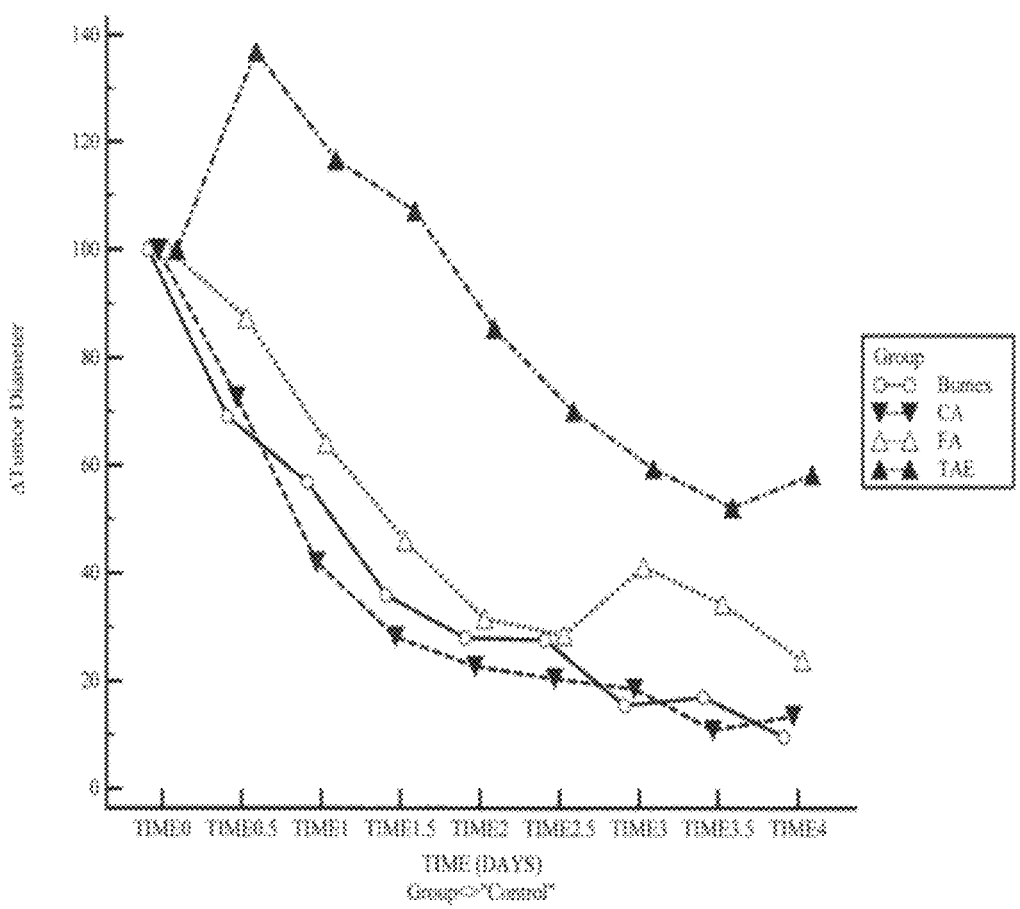
FIG. 34 shows a graph demonstrating the change in tumor diameter over time with the different treatment regimens.
Figure 35:
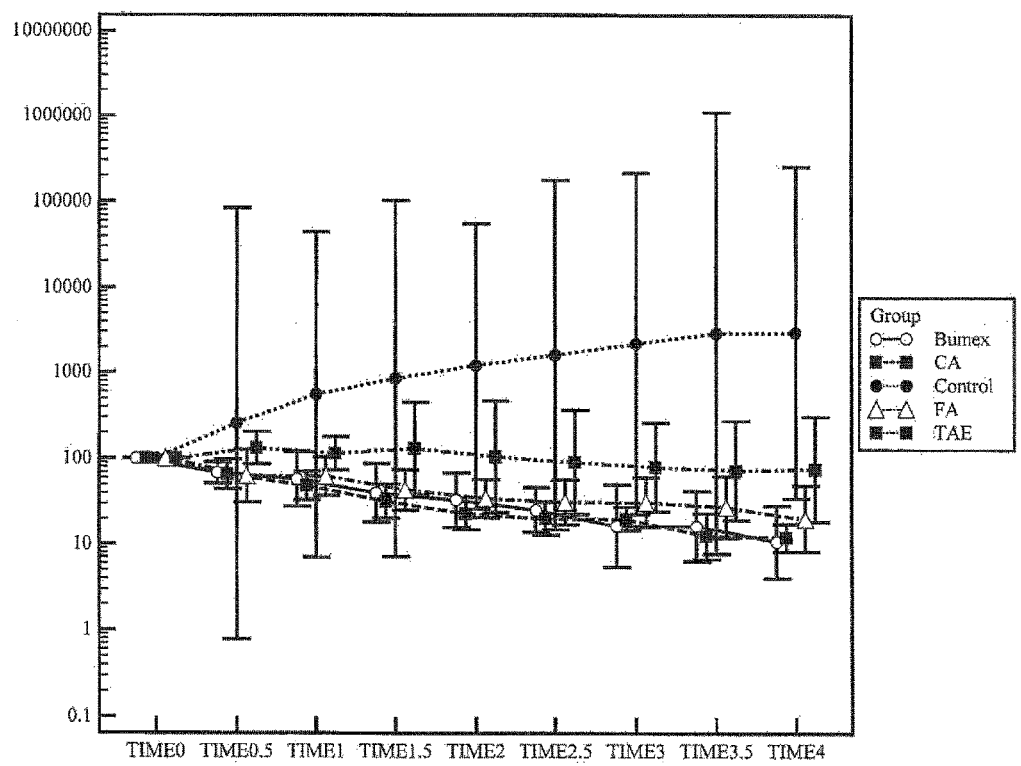
FIG. 35 shows a graph demonstrating the change in tumor diameter over time with the different treatment regimens with confidence intervals.
Figure 36:
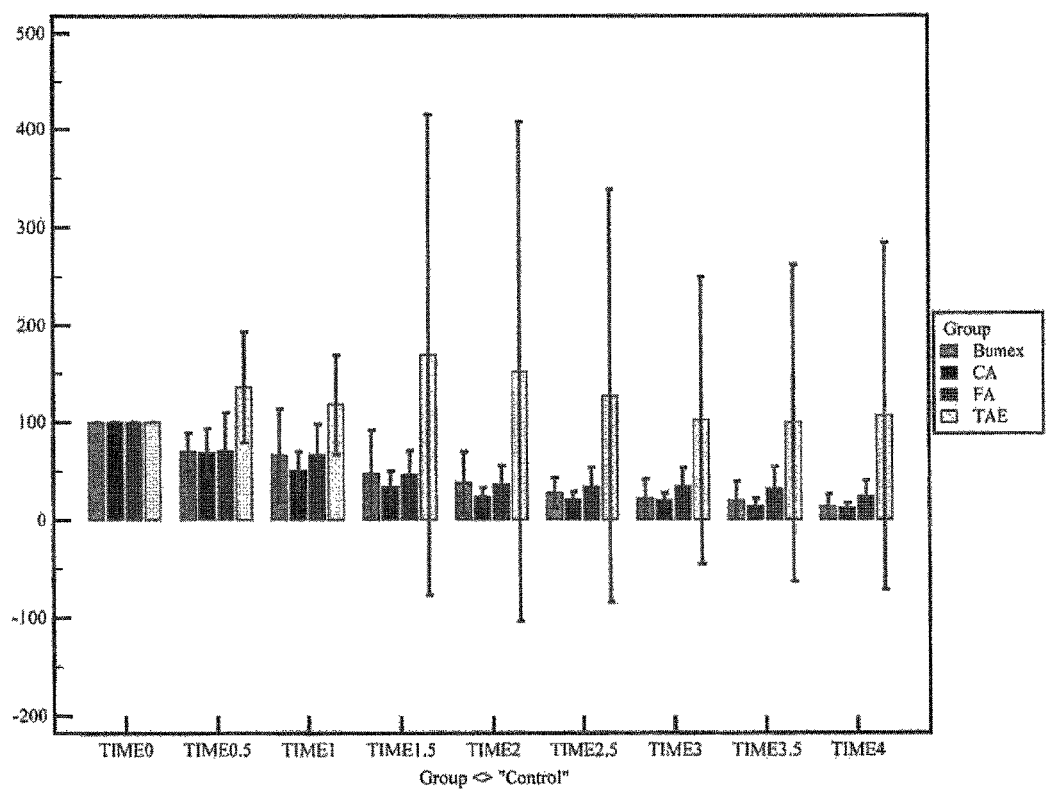
FIG. 36 shows a graph demonstrating the change in tumor diameter over time with the different treatment regimens with confidence intervals.
Figure 37:
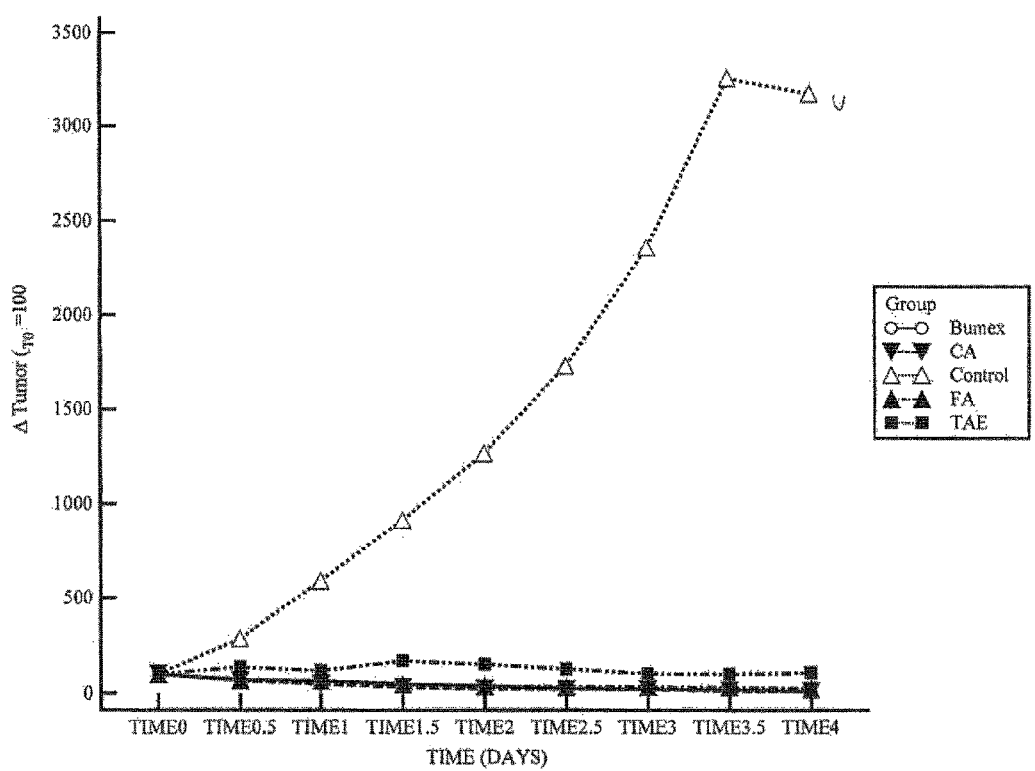
FIG. 37 shows a graph demonstrating the change in tumor diameter over time with the different treatment regimens.

The effects of the VEGFA on vessel formation were determined by adenovirus transfection of a VEGFA gene into normal mouse ears [18, 74, 75]. Lymphatic morphogenesis occurred at 1-3 days. Veins dilated and divided into smaller daughter veins at 3-5 days [18, 19, 71, 75], FIG. 14 and FIG. 15. Arterial capillaries and arterial venous malformations development occurred later at 7-10 days [18, 74, 75], FIG. 16.

Patan et al. [19], also, reported that the first tumor blood vessels to form are venous, which develop from the pre-existing host veins. Patan studied a xenograft colon cancer implant mouse model which grew for 21 days. From examination of the harvested masses she concluded, "Reconstruction of 3500 histological serial sections demonstrated that a new vascular network composed of venous-venous loops of varying sizes grows inside the tumor from the wall of the adjacent main vein". It should be noted that the author did not see any arterial changes in these dissections, FIG. 15.

Cancers can use both aerobic and glycolytic metabolic pathways. Each pathway requires vasculogenesis, but of a different nature. While aerobic metabolism is supported by arteries to supply oxygen, glycolytic metabolism depends upon lymphatic and venous drainage (ALPHA vasculogenesis) to manage lactate levels. The two processes are complementary, but ALPHA has a greater role because virtually all tumors eventually may lose their arterial supply and convert to predominantly glycolytic metabolism. Understanding the nature of ALPHA is important to radiologists because the modern imaging perfusion techniques are more consistent with ALPHA than the traditional oxygen based theory.

Example 1 describes a comparison study on hepatocellular rat model treatment using arterial embolization and embolization combined with anti-glycolytic agents. The example demonstrates that anti-glycolytic agents could enhance the effect of TAE on liver tumor.

Although it is not necessary to understand the mechanism of the current invention, it is believed that when either bumetanide or the hydroxycinnamates are given, glycolysis is interrupted. Although it is not necessary to understand the mechanism of the current invention, it is believed that bumetanide and acetazolamide may block carbonic anhydrases IX and XII which cause the intracellular pH of cancer to become less or more acidic. The low pH inhibits the rate limiting step of glycolysis, phosphofructose kinase. Although it is not necessary to understand the mechanism of the current invention, it is believed that bumetanide acts as a NKCC inhibitor. Although it is not necessary to understand the mechanism of the current invention, it is believed that with hydroxycinnamates the lactate transporters on the cell membrane are blocked so lactate accumulates inside the cell making it more acid and blocking the glycolytic reaction by "end product inhibition". Although it is not necessary to understand the mechanism of the current invention, it is believed that when either of these occurs glycolysis ceases so there is no ATP produced nor building substrates (proteins, lipids, nucleotides) produced which permit growth of the "mother cell" which is needed so division to occur to produce two daughter cells fully endowed with membranes, etc. If the cells cannot divide, they lapse into G0 cellular arrest. Non-dividing cells are not sensitive to radiation, or radioresistant i.e. radioprotectant. This is true of normal cells (radioprotectant) or cancer cells (radioresistant). When the activity of the drug wears off, cancer metabolism can again use both glycolysis and aerobic metabolism with existing mitochondria. Normal cells are more likely to have mitochondria so they have less reduction of ATP.

Embolization

Preoperative embolization of tumors is a well-established procedure that has been successfully applied in various clinical situations [76-80]. Preoperative embolization can reduce the vascularity of tumors resulting in a clearer operative field, easier dissection, decreased blood loss, and, in some cases, a decrease in tumor size.

A number of different materials have been used for embolization of tumors. Gelfoam has been used commonly in the past; however, because of the relatively large particle size, proximal occlusion of large vessels can lead to ineffective embolization. Sundaresan et al. used absolute ethanol for the preoperative embolization of spinal metastases from renal cancer with good results [81]. N-butyl cyanoacrylate and polymethlymethacrylate are commonly used embolic agents [82], and one author has described the use of a detachable balloon to occlude a vertebral artery before surgery for a cervical vertebral tumor Breslau et al. [83]. Non-absorbable PVA particles are one of the most frequently used embolic agents reported in the literature. PVA particles 150-250-mm in diameter result in distal embolization with occlusion at the capillary level. Larger particles, 250-500-mm in diameter, can then be used to embolize larger vessels or anastomoses. The use of non-absorbable PVA microspheres might prevent the recurrence of tumor hypervascularity due to recanalization of an embolized artery, which is commonly seen with absorbable gelatin sponges. Complications related to embolization are believed to be primarily due to devascularization of areas adjacent to the tumors being embolized, and in regions such as the spine, damage to adjacent areas can lead to permanent loss of functionality [84].

In some embodiments, the embolization material for embolic compositions comprises a polymer. Examples of polymers that can be used for creating particles for embolization include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly (lactic-co-glycolic) acids (e.g., poly(d-lactic-co-glycolic) acids) and copolymers or mixtures thereof. A preferred polymer is polyvinyl alcohol (PVA). The polyvinyl alcohol, in particular, is typically hydrolyzed in the range of from about 80 percent to about 99 percent. The weight average molecular weight of the base polymer can be, for example, in the range of from about 9000 to about 186,000 (e.g., from about 85,000 to about 146,000, from about 89,000 to about 98,000).

In general, individual embolization particles can have a diameter of from about ten microns to about 3,000 microns (e.g., from about 40 microns to about 2,000 microns; from about 100 microns to about 700 microns; from about 500 microns to about 700 microns; from about 100 microns to about 500 microns; from about 100 microns to about 300 microns; from about 300 microns to about 500 microns; from about 500 microns to about 1,200 microns; from about 500 microns to about 700 microns; from about 700 microns to about 900 microns; from about 900 microns to about 1,200 microns). In some embodiments, particle 10 can have a diameter of about 3,000 microns or less (e.g., about 2,500 microns or less; about 2,000 microns or less; about 1,500 microns or less; about 1,200 microns or less; about 1,000 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,000 microns or more; about 1,200 microns or more; about 1,500 microns or more; about 2,000 microns or more; about 2,500 microns or more).

In some embodiments, multiple particles are combined with a carrier fluid (e.g., a saline solution, a contrast agent, or both) to form an embolic composition. Such embolic compositions can be delivered to various sites in the body, including, for example, sites having cancerous lesions, such as the breast, prostate, lung, thyroid, or ovaries. The embolic compositions can be used in, for example, neural, pulmonary, and/or AAA (abdominal aortic aneurysm) applications. The compositions can be used in the treatment of, for example, fibroids, tumors, internal bleeding, arteriovenous malformations (AVMs), and/or hypervascular tumors in addition to cancerous lesions. The compositions can be used as, for example, fillers for aneurysm sacs, AAA sac (Type II endoleaks), endoleak sealants, arterial sealants, and/or puncture sealants, and/or can be used to provide occlusion of other lumens such as fallopian tubes, Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted. In some embodiments, a composition containing the particles can be used to prophylactically treat a condition.

The magnitude of a dose of an embolic composition can vary based on the nature, location and severity of the condition to be treated, as well as the route of administration. A physician treating the condition, disease or disorder can determine an effective amount of embolic composition. An effective amount of embolic composition refers to the amount sufficient to result in amelioration of symptoms or a prolongation of survival of the subject. The embolic compositions can be administered as pharmaceutically acceptable compositions to a subject in any therapeutically acceptable dosage, including those administered to a subject intravenously, subcutaneously, percutaneously, intratracheally, intramuscularly, intramucosaly, intracutaneously, intraarticularly, orally or parenterally.

An embolic composition can include a mixture of particles (e.g., particles that include different types of therapeutic agents), or can include particles that are all of the same type. In some embodiments, an embolic composition can be prepared with a calibrated concentration of particles for ease of delivery by a physician. A physician can select an embolic composition of a particular concentration based on, for example, the type of embolization procedure to be performed. In certain embodiments, a physician can use an embolic composition with a relatively high concentration of particles during one part of an embolization procedure, and an embolic composition with a relatively low concentration of particles during another part of the embolization procedure.

Suspensions of particles in saline solution can be prepared to remain stable (e.g., to remain suspended in solution and not settle and/or float) over a desired period of time. A suspension of particles can be stable, for example, for from about one minute to about 20 minutes (e.g. from about one minute to about ten minutes, from about two minutes to about seven minutes, from about three minutes to about six minutes).

In some embodiments, particles can be suspended in a physiological solution by matching the density of the solution to the density of the particles. In certain embodiments, the particles and/or the physiological solution can have a density of from about one gram per cubic centimeter to about 1.5 grams per cubic centimeter (e.g., from about 1.2 grams per cubic centimeter to about 1.4 grams per cubic centimeter, from about 1.2 grams per cubic centimeter to about 1.3 grams per cubic centimeter).

In some embodiments, the carrier fluid of an embolic composition can include a surfactant. The surfactant can help the particles to mix evenly in the carrier fluid and/or can decrease the likelihood of the occlusion of a delivery device (e.g., a catheter) by the particles. In some embodiments, the surfactant can enhance delivery of the embolic composition (e.g., by enhancing the wetting properties of the particles and facilitating the passage of the particles through a delivery device). In certain embodiments, the surfactant can decrease the occurrence of air entrapment by the particles in a composition (e.g., by porous particles in a composition). Examples of liquid surfactants include Tween® 80 (available from Sigma-Aldrich) and Cremophor EL® (available from Sigma-Aldrich). An example of a powder surfactant is Pluronic® F127 NF (available from BASF). In certain embodiments, an embolic composition can include from about 0.05 percent by weight to about one percent by weight (e.g., about 0.1 percent by weight, about 0.5 percent by weight) of a surfactant. A surfactant can be added to the carrier fluid prior to mixing with the particles and/or can be added to the particles prior to mixing with the carrier fluid.

In some embodiments, a plurality of the particles (e.g., in an embolic composition) can be delivered through a catheter having a lumen with a cross-sectional area that is smaller (e.g., about 50 percent or less) than the uncompressed cross-sectional area of the particles. In such embodiments, the particles are compressed to pass through the catheter for delivery into the body. Typically, the compression force is provided indirectly, by depressing the syringe plunger to increase the pressure applied to the carrier fluid. In general, the particles are relatively easily compressed to diameters sufficient for delivery through the catheter into the body. The relatively robust, rigid surface region of the particles can resist abrasion when the particles contact hard surfaces such as syringe surfaces, hard plastic or metal stopcock surfaces, and/or the catheter lumen wall (made of, e.g., Teflon) during delivery. Once in the body, the particles can substantially recover to original diameter and shape for efficient transport in the carrier and body fluid stream. At the point of occlusion, the particles can again compress as they aggregate in the occlusion region. The particles can form a relatively dense occluding mass. The compression of the particles in the body is generally determined by the force provided by body fluid flow in the lumen. In some embodiments, the compression may be limited by the compression profile of the particles, and the number of particles needed to occlude a given diameter may be reduced.

In one embodiment, the present invention contemplates a method for cancer treatment comprising embolization in combination with metabolic pathway modulation drugs. Non-limiting examples of polymeric embolization materials and methods are described in U.S. Pat. No. 7,964,123 [85]. Although it is not necessary to understand the mechanism of the current invention, it is believed that when embolic material is administered with either bumetanide or the ferrulic acid or caffeic acid, the ATP production is more severely reduced because neither pathway is functional. Closure of the vessel by embolic blockage prevents blood flow and oxygenation. With markedly reduce ATP, cells die from programmed cell death or apoptosis (if ATP reduced by about 20%) or necrosis if reduced more than 20%).

Although it is not necessary to understand the mechanism of the current invention, it is believed that when Avastin is combined with Bumetanide, a similar effect occurs. Small arteries are occluded from anti-VEGF damage to the small veins. With vein occlusion, it is believed that arterial occlusion concomitantly occurs because artery inflow is dependent upon venous outflow. With Avastin administration, sites of neoangiogenesis are more affected so tumors are affected more than stable normal tissue. Resulting in, for example, reduced ATP energy, apoptosis or necrosis as described above.

Although it is not necessary to understand the mechanism of the current invention, it is believed that either Avastin or bumetanide/hydoxycinnamates may partially affect tumors temporarily until cancer switches from aerobic to glycolysis or back (apparently there can be "gained" attributes from mutations, i.e. mitochondria can regenerate in cancer cells. However, without ATP it is believed that the cells may not be able to live.

Both Cancer cells and normal cells make ATP by BOTH aerobic (oxygen/artery) and glycolysis. If the arteries are impaired by occlusion/emboli and cessation of glycolysis occurs, the cells die. It is said if ATP is reduced by 20%, programmed death occurs (apoptosis). If a greater reduction occurs, the cells necrose quickly. Without ATP production, the cells cannot live. The animal models show the effect of interrupting both aerobic and glycolysis simultaneously.

Two separate reports, one showing the effects of anti VEGF (i.e. Avastin) on a glioblastoma tumor (Keunen 2011 [10]) and the effects of a hydroxycinnamate compound on a glioblastoma (Colen 2011 [86]) reflect possible impacts of individual compound therapy. Individually, both show a reduction of tumor size. Combining the two compounds is thought to likely destroy aerobic cells and glycolytic cells (blocks lactate transport and thereby end product inhibition of glycolysis). With the two components, cancer should be denied of all ATP. Normal cells which use aerobic may have little or no lactate, i.e. lactate transporters. Normal tissues may not have new angiogenesis (target of Avastin).

Although it is not necessary to understand the mechanism of the present invention, it is believed that hydroxycinnamates have an effect in which the compounds block the transport of lactate through the MCT transporters so that glycolysis temporarily blocks glycolysis by virtue of end product inhibition of glycolysis by increased lactate. Bumetanide likely blocks glycolysis by prevent CAIX from producing $HCO_3$ which buffers acidity, thereby producing low pH intracellularly. The rate-limiting step of glycolysis phosphofructose kinase is very sensitive to low pH so inhibits glycolysis. The effects of either compound is to impair glycolysis so less ATP is available and Mother dividing cells lapse into G0 because the substrates derived from the side reactions of glycolysis (makes proteins, nucleotides, etc).

Although it is not intended to limit the present invention, it is believed that it is possible that long term Bumetanide or long-term hydrocinnamates could induce cellular arrest G0. These are very safe drugs and putting a tumor into dormancy (e.g., not growing) is perhaps as good as or better than killing a tumor. Seeking ways to put tumors into dormancy for management as chronic diseases, in lieu of killing them, may be a preferable therapeutic avenue. Cancer cell killing therapies have disadvantages because most chemical treatments select out "resistant clones" which then become more aggressive. Although it is not intended to limit the present invention, it is believed that because hydroxycinnmates or Bumetanide inhibit glycolysis temporarily, sustained administration may produce long-term dormancy. They can both be taken orally.

Although the invention has been described with reference to these preferred embodiments, other embodiments can achieve the same results. Variations and modifications of the present invention may be obvious to those skilled in the art and it is intended to cover in the appended claims all such modifications and equivalents. The entire disclosures of all applications, patents, and publications cited above, and of the corresponding application are hereby incorporated by reference.

Thus, specific compositions and methods of targeted treatment of anaerobic cancer have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Detailed Description of Drugs

VEGF inhibitors or anti-VEGF therapy may involve binding of an agent to VEGF to prevent its modulation of a receptor such as VEGFR-1 (flt-1), VEGFR-2 (flk-1 or KDR), or through inhibition of tyrosine kinase in promoting angiogenesis or it may inhibit the binding of VEGF to one or more of its receptors by any one or more mechanisms. Regardless of the mechanism of action, anti-VEGF activity associated with the use of an effective amount of a VEGF inhibitor in the present invention results in a reduction in VEGF activity (angiogenesis/vascularization) in the tumor, and a response which is inhibitory to cancer growth, elaboration and metastases and which helps to promote cancer remission in combination with the other agents. Bevacizumab is a preferred VEGF inhibitor for use in the present invention. Compounds/compositions according to the present invention which represent anti-VEGF therapy (angiogenesis inhibitors) include for example, ZD6474, ZD 6126, AZD2171 (Astra Zeneca), SU6668 and SU5416 (Sugen), bevacizumab (Avastin), mv833, anti-FLT-1 ribozyme (Angiozyme), and the tyrosine kinase inhibitors SU5416 (Semaxanib), PTK 787 (ZK 222584), ZD4190, ZD6474, CEP-7055, SU11248 and mixtures thereof. In one embodiment anti-angiogenic agents include tumor-vascular disrupting agents described by Siemann (2011) [87], incorporated herein by reference.

Vandetanib (rINN, trade name Caprelsa), also known as ZD6474, is an antagonist of the vascular endothelial growth factor receptor (VEGFR) and the epidermal growth factor receptor (EGFR). It is a tyrosine kinase inhibitor, being developed by AstraZeneca.

ZD6126 is a vascular-targeting agent and a prodrug of N-acetylcolchinol, related to colchicine.

Cediranib (tentative trade name Recentin), also known as AZD2171, is a potent inhibitor of vascular endothelial growth factor (VEGF) receptor tyrosine kinases developed by Astra Zeneca.

SU6668, a multitargeted angiogenesis inhibitor described in Klenke et al. (2007) [88], incorporated herein by reference.

Semaxanib (SU5416) is a tyrosine-kinase inhibitor drug designed by SUGEN as a cancer therapeutic. It is an experimental stage drug, not licensed for use on human patients outside of clinical trials. Semaxanib is a potent and selective synthetic inhibitor of the Flk-1/KDR vascular endothelial growth factor (VEGF) receptor tyrosine kinase. It targets the VEGF pathway, and both in vivo and in vitro studies have demonstrated antiangiogenic potential.

Mv833 is anti-human VEGF monoclonal antibody.

Anti-FLT-1 ribozyme or Angiozyme is a substance that is being studied in the treatment of kidney cancer. It may prevent the growth of blood vessels from surrounding tissue to the tumor. It belongs to the families of drugs called VEGF receptor and angiogenesis inhibitors. Angiozyme is also called RPI.4610.

The tyrosine kinase inhibitors include, but are not limited to: SU5416 (Semaxanib), PTK 787 (Vatalanib), ZD4190, ZD6474 (Vandetanib), CEP-7055, and SW 1248 (Sunitinib).

Semaxanib (SU5416) is a tyrosine-kinase inhibitor drug designed by SUGEN as a cancer therapeutic. Semaxanib is a potent and selective synthetic inhibitor of the Flk-1/KDR vascular endothelial growth factor (VEGF) receptor tyrosine kinase. It targets the VEGF pathway, and both in vivo and in vitro studies have demonstrated antiangiogenic potential.

Vatalanib (also known as PTK787 or PTK/ZK) is a small molecule protein kinase inhibitor that inhibits angiogenesis. Vatalanib is being developed by Bayer Schering and Novartis. It inhibits all known VEGF receptors, as well as platelet-derived growth factor receptor-beta and c-kit, but is most selective for VEGFR-2.

Vandetanib (trade name Caprelsa), also known as ZD6474, is an antagonist of the vascular endothelial growth factor receptor (VEGFR) and the epidermal growth factor receptor (EGFR). It is a tyrosine kinase inhibitor, being developed by AstraZeneca.

Sunitinib (marketed as Sutent by Pfizer, and previously known as SU11248) is an oral, small-molecule, multi-targeted receptor tyrosine kinase (RTK) inhibitor.

Bevacizumab (Avastin®) (rhuMAb-VEGF)(Anti-VEGF monoclonal antibody) is a recombinant human/murine chimeric monoclonal antibody directed against vascular endothelial growth factor (VEGF).). It is prepared by engineering VEGF-binding residues of a murine anti-VEGF monoclonal antibody into framework regions of human immunoglobulin-1 (IgG1) (Prod Info Avastin, 2004). Only 7% of the amino acid sequence is derived from the murine antibody, with 93% from IgG1, Figg, W. D. et al. (2002) [89] incorporated herein by reference.

Human VEGF mediates neoangiogenesis in normal and malignant vasculature; it is overexpressed in most malignancies and high levels have correlated with a greater risk of metastases and poor prognosis in many. When VEGF interacts with its receptor in in vitro models of angiogenesis, endothelial cell proliferation and new blood vessel formation occur. In animal models, VEGF has been demonstrated to induce vascular endothelial-cell proliferation/migration, sustain survival of newly-formed blood vessels, and enhance vascular permeability. Bevacizumab binds and neutralizes all human VEGF forms via recognition of binding sites for the two human VEGF receptor types (flt-1 and flk-1). In animal models, the antibody has been shown to stabilize established tumors or suppress tumor growth by inhibiting angiogenesis induced by VEGF, Gordon, M. S. et al. (2001) [90] incorporated herein by reference.

Toxicology of Bevacizumab: Minor bleeding or hemorrhage (e.g., epistaxis, and hemoptysis), and thromboembolic events (e.g., deep vein thrombosis) have accompanied administration of bevacizumab in some cancer patients. Other serious but uncommon events included; gastrointestinal hemorrhage, subarachnoid hemorrhage, fatal pulmonary hemorrhage, and hemorrhagic stroke (Prod Info Avastin™, 2004). Grade ¾ hypertension (12%), deep venous thrombosis (9%), and intra-abdominal thrombosis (3%)

occurred in patients receiving bolus irinotecan/5-fluorouracil/leucovorin plus bevacizumab in a trial of patients with untreated metastatic colorectal cancer. Myocardial infarction and hypotension have also been reported. Modest increases in diastolic and systolic blood pressures and clinical hypertension have been reported frequently during bevacizumab therapy (23% to 34% of patients) and may need to be controlled with antihypertensive medications. Mild asthenia and headache have been common during therapy (up to 70% and 50% of patients, respectively), but may be dose-dependent. Dizziness (22%), hypokalemia (14%) and bilirubinemia (4%) vomiting (50%), anorexia (40%), constipation (30%), stomatitis (30%), dyspepsia (20%), weight loss (15%), taste disorder (16%) and flatulence (16%), myalgia (10%), skin ulcer (6%) and confusion (3%) may occur. Grade ¾ diarrhea (30%) and abdominal pain (6%) were also reported. Nausea and vomiting may be more severe with higher doses. Gastrointestinal perforation occurred in 2% of patients receiving bolus irinotecan/5-fluorouracil/leucovorin plus bevacizumab versus 4% of patients receiving 5-fluorouracil/leucovorin plus bevacizumab in a trial of patients with untreated metastatic colorectal cancer; a typical presentation included abdominal pain, constipation, and vomiting, Hurwitz, H. (2003)[91], incorporated herein by reference.

Proteinuria of varying severity or nephrotic syndrome has been described during therapy with bevacizumab, Cobleigh, M. A. et al. (2003) [92] incorporated herein by reference. Life threatening or fatal pulmonary hemorrhage occurred in 3 to 1% of patients with squamous cell non-small cell lung cancer (4% nonsquamous cell histology) receiving bevacizumab in combination with chemotherapy compared to 0% in the chemotherapy alone group; these events presented suddenly as major hemoptysis and occurred in patients with cavitation and/or necrosis of the tumor, either preexisting or developing during therapy, Chen, et al. (2001) [93] incorporated herein by reference. Skin rash (type unspecified) has been described in some patients following infusion. Low-grade fever and infection have occurred with variable frequency during therapy. The incidence of immunogenicity with bevacizumab exists, but has not been determined (prod info Avastin™, 2004). No antibodies to bevacizumab were reported in a phase I study (n=25) where patients received four doses of 0.1 to 10 mg/kg over 42 days, and assays were performed for up to 70 days, Gordon, M. S. et al. (2001) [90] incorporated herein by reference. There is insufficient clinical experience with bevacizumab to confirm its safety in pregnancy.

Black Box Warnings for Bevacizumab: Gastrointestinal Perforations/Wound Healing Complications: Avastin administration can result in the development of gastrointestinal perforation and wound dehiscence, in some instances resulting in fatality. Gastrointestinal perforation, sometimes associated with intra-abdominal abscess, occurred throughout treatment with Avastin (i.e., was not correlated to duration of exposure). The incidence of gastrointestinal perforation in patients receiving bolus-IFL with Avastin was 2%. The typical presentation was reported as abdominal pain associated with symptoms such as constipation and vomiting. Gastrointestinal perforation should be included in the differential diagnosis of patients presenting with abdominal pain on Avastin. Avastintherapy should be permanently discontinued in patients with gastrointestinal perforation or wound dehiscence requiring medical intervention. The appropriate interval between termination of Avastin and subsequent elective surgery required to avoid the risks of impaired wound healing/wound dehiscence has not been determined.

Hemorrhage: Serious, and in some cases fatal, hemoptysis has occurred in patients with non-small cell lung cancer treated with chemotherapy and Avastin. In a small study, the incidence of serious or fatal hemoptysis was 31% in patients with squamous histology and 4% in patients with adenocarcinoma receiving Avastin as compared to no cases in patients treated with chemotherapy alone. Patients with recent hemoptysis should not receive Avastin.

Pharmacology of Bevacizumab: The pharmacokinetics of bevacizumab are linear after doses of 0.3 mg/kg or greater. Following 90-minute intravenous infusions of 0.3, 1, 3, and 10 mg/kg in advanced cancer patients (n=25), peak serum concentrations of bevacizumab ranged from 5 to 9 mcg/mL, 21 to 39 mcg/mL, 52 to 92 mcg/mL, and 186 to 294 mcg/mL, respectively; slight accumulation was observed with repeat doses (weekly), but this was not significant and pharmacokinetics remained linear. Steady-state levels of bevacizumab were obtained in 100 days in 491 patients who received 1 to 20 mg/kg weekly, every 2 weeks, or every 3 week Following 90-minute intravenous infusions of 0.3, 1, 3, and 10 mg/kg in advanced cancer patients (n=25), $AUC_{inf}$ values ranged from 31 to 87, 240 to 382, 550 to 1720, and 2480 to 6010 mcg/mL×day, respectively, Gordon, M. S. et al. (2001) [90] incorporated herein by reference. Central volume of distribution of bevacizumab was greater in males than in females (3.25 L vs. 2.66 L) in 491 patients who received 1 to 20 mg/kg weekly, every 2 weeks, or every 3 week. The clearance of bevacizumab was higher (0.262 L/day vs. 0.207 L/day) in males than females; patients with a higher tumor burden (at or above median value of tumor surface area) also had a higher clearance (0.249 L/day vs. 0.199 L/day). The estimated elimination half-life of bevacizumab was 20 days (range 11 to 50 days) in a pharmacokinetic population analysis of 491 patients receiving 1 to 20 mg/kg weekly, every 2 weeks, or every 3 weeks.

VEGF Serum Level Changes: In advanced cancer patients, free VEGF serum levels were reduced significantly following the first dose of bevacizumab 1 to 10 mg/kg, and remained below the limit of detection for the duration of the study (repeat doses at 28, 35, and 42 days). Levels of total VEGF increased with all doses (0.1 to 10 mg/kg), presumably as a result of increased VEGF synthesis/distribution or reduced VEGF clearance secondary to complex formation (between VEGF and bevacizumab), Gordon, M. S. et al. (2001) [90] herein incorporated by reference.

Storage And Stability: Store bevacizumab vials protected from light, under refrigeration at 2 to 8 degrees Celsius/36 to 46 degrees Fahrenheit. Do not freeze or shake. This product contains no preservative (Prod Info Avastin™, 2004).

Diluted solutions of bevacizumab in 100 mL 0.9% Sodium chloride Injection may be stored for up to 8 hours under refrigeration (2 to 8 degrees Celsius/36 to 46 degrees Fahrenheit) (Prod Info Avastin™, 2004). Early phase I trials were conducted with bevacizumab diluted in 5% Dextrose for Injection. However, results indicate that dextrose inactivates bevacizumab.

Dosage and Administration: The recommended dose of bevacizumab is 5 milligrams/kilogram infused intravenously over 30 minutes every 2 weeks until disease progression diminishes. Bevacizumab should follow chemotherapy. Efficacy of single-agent bevacizumab has not been established. The calculated dose of bevacizumab in 100 milliliters of 0.9% Sodium Chloride Injection should initially be infused over 90 minutes; subsequent doses can be administered in shorter periods of time (60 minutes for the second infusion and 30 minutes for the third infusion, if well-tolerated). Do not administer as an intravenous bolus or push (Prod Info Avastin™, 2004).

The term "effective" or "effective amount" means an amount of a compound which is used to effect an intended result. In the present application, the favorable treatment of cancer is the intended effect, manifest in a remission or shrinkage of the cancer/tumor and/or the prevention or a reduction in or the likelihood of the spread (metastases) of the cancer and a substantial increase in the time of survival. The present method may result in an increase in survival of a patient diagnosed with cancer to at least about 1.5 times, at least about 2 times, at least about 2.5 times, at least about 3 times, at least about 3.5 times, at least about 4 times, at least about 5 times, at least about 6 times, at least about 7 times, at least about 8 times, at least about 9 times and at least about 10 times or more the length of time of survival of the untreated patient determined from the time the cancer is diagnosed in the patient. Optimally, the present invention may result in the improvement of the well being of the patient, a shrinkage of the tumor, a prolongation of survival, the remission of cancer and the prevention (as a manifestation of a reduced likelihood or prevention) of metastases of the cancer to other areas of the patient's body. In general, effective amounts of each of the compounds used in the combined therapy according to the present invention include:

Bumetanide—between about 100 mg and 2.5 grams, preferably about 500 mg to about 2000 mg, preferably about 800 mg, about 1000 mg or about 1500 mg/mm$^2$. A slow release form of bumetanide is preferably used such that release of the drug would be evenly released over 8 to 12 hours. In another embodiment, the bumetanide is incorporated into polymers for much longer term release.

Bevacizumab (which may be coadministered with bumetanide, or within a week before or after chemotherapy), is administered intravenously, at about 1 mg/kg to about 15 mg/kg, preferably about 5 mg/kg.

The above combination is preferably administered once about every one-two weeks (preferably about every two weeks twice with each course—one course equals 2 dosages—(preferably a total of 6 courses) preferably being administered over a 4-8 week period (preferably over 4 weeks), although the regimen may be administered more frequently depending upon the disease state. Of course, further courses of the combination therapy may be given, as the disease state merits. The dosage of each of the components may be modified to reflect the size and weight of the patient, as well as the severity of the disease state to be treated.

In some aspects of the present invention, the combined therapy described above is administered once every two weeks for a total of 12 dosages. The components are preferably coadministered, although it is sometimes desirable to administer the bevacizumab (anti-VEGF therapy) within one week of the chemotherapeutic compounds or compositions and/or a carbonic anhydrase inhibitor, such as acetazolamide.

In additional aspects of the present invention, the premedications dexamethasone, at about 5-10 (preferably 8 mg) mg every 12 hours for six doses (three days) and/or zofran (5-10 mg, preferably 8 mg IV) are administered in effective amounts prior to chemotherapy and then intermittently during further therapy pursuant to physician discretion. The dosage schedules according the present invention are referred to herein as low dose, frequent administration.

Formulations

A "pharmaceutically acceptable monosaccharide" is a pharmaceutically acceptable aldose sugar, a pharmaceutically acceptable ketose sugar, or other specified sugar. Among the pharmaceutically acceptable aldose sugars within the contemplation of the present invention are erythrose, threose, ribose, arabinose, xylose, lyxose, allose, altrose, glucose, mannose, gulose, idose, galactose and talose. Among the pharmaceutically acceptable ketose sugars preferred for use in the composition of the present invention are erythrulose, ribulose, xylulose, psicose, fructose, sorbose, tagatose, and sedoheptulose. Among the other specified sugars preferred for use in the composition of the present invention are fucose, fuculose, rhamnose, or any other deoxy sugar. Although either (D) or (L) isomers may be employed, the (D) form is generally preferable.

The pharmaceutical compositions of the present invention may be prepared by formulating them in dosage forms that are suitable for peroral, rectal or nonparenteral administration, the last-mentioned including intravenous injection and administration into the cerebrospinal fluid. For this purpose, common carriers and routine formulation techniques may be employed.

"API" or "active pharmaceutical ingredient" means the substance in a pharmaceutical drug that is biologically active.

"Common carriers" means those that are employed in standard pharmaceutical preparations and includes excipients, binders and disintegrators the choice of which depends on the specific dosage form used. Typical examples of the excipient are starch, lactose, sucrose, glucose, mannitol and cellulose; illustrative binders are polyvinylpyrrolidone, starch, sucrose, hydroxypropyl cellulose and gum arabic; illustrative disintegrators include starch, agar, gelatin powder, cellulose, and CMC. Any other common excipients, binders and disintegrators may also be employed.

In addition, of the carriers described above, the pharmaceutical composition of the present invention preferably contains antioxidants for the purpose of stabilizing the effective ingredient. Appropriate antioxidants may be selected from among those that are commonly incorporated in pharmaceuticals and include ascorbic acid, N-acetylcysteine, acetylcysteine, L-cystein, D, L-α-tocopherol, and natural tocopherol.

Formulations of the pharmaceutical composition of the present invention which are suitable for peroral administration may be provided in the form of tablets, capsules, powders, granules, or suspensions in non-aqueous solutions such as syrups, emulsions or drafts, each containing one or more of the active compounds in predetermined amounts.

The granule may be provided by first preparing an intimate mixture of one or more of the active ingredients with one or more of the auxiliary components shown above, then granulating the mixture, and classifying the granules by screening through a sieve.

The tablet may be prepared by compressing or otherwise forming one or more of the active ingredients, optionally with one or more auxiliary components.

The capsule may be prepared by first making a powder or granules as an intimate mixture of one or more of the active ingredients with one or more auxiliary components, then charging the mixture into an appropriate capsule on a packing machine, etc.

The pharmaceutical composition of the present invention may be formulated as a suppository (for rectal administration) with the aid of a common carrier such a cocoa butter. The pharmaceutical composition of the present invention may also be formulated in a dosage form suitable for non-parenteral administration by packaging one or more active ingredients as dry solids in a sterile nitrogen-purged container. The resulting dry formulation may be administered to patients non-parenterally after being dispersed or dissolved in a given amount of aseptic water.

The dosage forms are preferably prepared from a mixture of the active ingredients, routine auxiliary components and one or more of the antioxidants listed above. If desired, the formulations may further contain one or more auxiliary components selected from among excipients, buffers, flavoring agents, binders, surfactants, thickening agents, and lubricants.

The dose of the various pro-drugs may of course vary with the route of administration, the severity of the disease to be treated, and the patient to be treated, but the exact dose ultimately chosen should be left to the good discretion of the doctor responsible for the treatment. If a desired dose is determined, the active ingredient may be administered once a day or, alternatively, it may be administered in up to as many portions as deemed appropriate at suitable intervals. The active ingredient may be straightforwardly administered without being mixed with any other components. However, for several reasons, typically for the purpose of providing ease in controlling the dose level, the active compound is preferably administered in a pharmaceutical dosage form.

EXPERIMENTAL

Example 1

Comparison Study on Hepatocellular Rat Model Treatment Using Arterial Embolization and Embolization Combined with Anti-Glycolytic Agents Purpose:
To determine if anti-glycolytic agents (AG) combined with transarterial embolization (TAE) improves treatment of an N1-S1 tumor model implanted in Sprague-Dawley rat livers.
Methods:
The animal experiments were approved by the Institutional Animal Care and Use Committee. Subcapsular implantation of N1-S1 hepatoma in the liver after laparotomy was carried out in Sprague Dawley rats. 10-15 days later, a laparotomy and retrograde placement of a catheter into the gastroduodenal artery was performed, the following different agents of interventional treatment were injected into the hepatic artery on 5 different treatment groups: 1) Control (n=5, 1 ml normal saline); 2) TAE (n=4, 10 mg 50-150 μm polyvinyl alcohol (PVA) particle in 1 ml normal saline), 3) TAE+Bumetanide (n=5, 10 mg PVA in 1 ml AG-B (Btunetanide)); 4) TAE+AG-F (ferulic acid) (n=5, 10 mg PVA+30 mg AG-F (ferulic acid) in 1 ml normal saline); 5) TAE+AG-C (caffeic acid) (n=5, 10 mg PVA+30 mg AG-C (caffeic acid) in 1 ml normal saline). The agents were slowly injected within 2 minutes. Tumor length (L), width (W), and height (H) was measured by 2D-ultrasound before treatment and twice a week for 4 weeks after treatment. Tumor volume (V) was calculated by the formula: V=0.5*L*W*H. Relative tumor volume after treatment was calculated as the percentage of pre-treatment tumor volume. Kruskal-Wallis test with Minitab 16 was used to compare the difference of relative tumor volume between five groups on each observation time point.
Results:
The differences between all five groups were not significant (706.1 mm$^3$±633.7, 580.4 mm$^3$±192.4, 455.8 mm$^3$±192.1, 732.2 mm$^3$±549.2, and 467.6 mm$^3$±181.6 in groups 1, 2, 3, 4 and 5, respectively), Three animals were euthanized before the end of observation (on days 10, 11, and 21 respectively) due to rapid tumor growth and anorexia in control group. In TAE group, one kept growing after treatment. In other three animals, the tumor volume increased in the early observation time points (1 within 1 week, 2 within 2 weeks after treatment) and then shrunk. In other three TAE+AG groups, the tumor volumes decreased after treatment. Significant differences in relative tumor volume were noted between control group and 3 TAE+AG groups on all observation time point except on week 3.5 and 4 in TAE+AG-F (ferulic acid) group. Significant differences were also noted between TAE group and TAE+AG-C (caffeic acid) group on week 2-4. At 4 weeks after treatment, the median relative tumor volumes were 3,174.5% in control group, 58.2% in TAE group, 9.6% in TAE+AG-B (Bumetanide) group, 23.8% in TAE+AG-F (ferulic acid) group, and 13.4% in TAE+AG-C (caffeic acid) group, see FIG. 17-FIG. 23.
Conclusions:
Anti-glycolytic agents could enhance the effect of transarterial embolization on liver tumor. In the baseline state, both glycolysis and aerobic metabolism can be used by either normal cells or cancerous cells. The difference between the two is that cancer is more dependent upon glycolysis than normal cells (see last item on Bumetanide after reading). The types of normal cells that use aerobic and glycolysis are rapidly proliferating cells.

Example 2

Additional Comparison Study on Hepatocellular Rat Model Treatment Using Arterial Embolization and Embolization Combined with Anti-Glycolytic Agents Purpose:
To determine if anti-glycolytic agents (AG) combined with transarterial embolization (TAE) improves treatment of an N1-S1 tumor model implanted in Sprague-Dawley rat livers.
Methods:
The animal experiments were approved by the Institutional Animal Care and Use Committee. Subcapsular implantation of N1-S1 hepatoma in the liver after laparotomy was carried out in Sprague Dawley rats. 10-15 days later, a laparotomy and retrograde placement of a catheter into the gastroduodenal artery was performed, the following different agents of interventional treatment were injected into the hepatic artery on 4 different treatment groups: 1) TAE (n=4, 10 mg 50-150 μm polyvinyl alcohol (PVA) particle in 1 ml normal saline), 2) TAE+Bumetanide (n=5, 10 mg PVA in 1 ml AG-B (Bumetanide)); 3) TAE+AG-F (ferulic acid) (n=5, 10 mg PVA+30 mg AG-F (ferulic acid) in 1 ml normal saline); 4) TAE+AG-C (caffeic acid) (n=5, 10 mg PVA+30 mg AG-C (caffeic acid) in 1 ml normal saline). The agents were slowly injected within 2 minutes. Tumor length (L), width (W), and height (H) was measured by 2D-ultrasound before treatment and twice a week for 4 weeks after treatment. Tumor volume (V) was calculated by the formula: V=0.5*L*W*H. Relative tumor volume after treatment was calculated as the percentage of pre-treatment tumor volume. Kruskal-Wallis test with Minitab 16 was used to compare the difference of relative tumor volume between 4 groups on each observation time point.

Results:

See FIG. 24-FIG. 37.

Example 3

DCE-MRI with a Biodegradable Macromolecular Contrast Agent Reveals Anti-Angiogenic Effects of Bumetanide in a Colon Cancer Model Objectives:

The FDA approved drug, bumetanide, is an inhibitor of Na+-K+-2Cl—(NKCC1) cotransporters in the cell. Although it is not traditionally used in cancer therapy, it is possible that it may work to reduce the proliferation and migration of tumor and cells, while also enhancing susceptibility to apoptotic mechanisms in the presence of chemotherapeutics. The efficacy of bumetanide in cancer treatment was evaluated in an investigational study, described in the following, that utilized DCE-MRI to assess its potential anti-angiogenic effects.

Materials and Methods:

Dynamic contrast-enhanced (DCE) MRI is a non-invasive imaging technique that is able to quantify the anatomical and physiological progression of tumor angiogenesis in response to a variety of different cancer therapies. In order to allow for the safe use of macromolecular contrast medium, a novel polydisulfide-based agent, poly([(Gd-DOTA)-DETA]-co-DTBP) (GODP) was designed, which initially starts as a macromolecular agent during an DCE-MRI protocol, and is then gradually degraded by endogenous thiols in the reductive environment of the bloodstream to improve renal clearance. In this study, two groups of 3 mice, bearing flank HT29 colon cancer xenografts, were treated daily with either bumetanide or saline for a total of 3 weeks. DCE-MRI was performed before and after the start of treatment on a weekly basis, and the collected was analyzed using the adiabatic approximation to the tissue homogeneity (AATH) model. IHC and western blot analysis was performed to study the changes in CD31, VEGF, and tissue hypoxia.

Results:

Here, the new GODP contrast agent was shown able to aid in detecting the ability of bumetanide to reduce tumor vascularity during the treatment period. DCE-MRI revealed that the bumetanide therapy induced greater reductions in the PS and $V_p$ parameters than the saline control therapy, in comparison to their respective pre-treatment levels. The accuracy of these changes was verified by the significant decline of CD31 and VEGF expression. Despite a significant regression in vascularity, the tumors remained highly proliferative, as tumor size and Ki67 levels did not subside at all. Overexpression of the transcription factor HIF-1α in response to elevated hypoxia is thought to be the driving force behind the uninterrupted tumor expansion. Since VEGF is a downstream target of HIF-1α, it is possible that bumetanide possesses a direct inhibitory effect on the production of this angiogenic factor, thus contributing to the decline in tumor vascularity.

Conclusions:

This study demonstrated the effectiveness of GODP in detecting vascular changes in the tumor microenvironment following the administration of bumetanide therapy. The findings suggest that bumetanide has the potential ability to curtail growth of the tumor vasculature and can be employed in future therapeutic strategies, although further studies are required to uncover the biological mechanisms behind its anti-angiogenic effects.

Introduction

Dynamic contrast enhanced (DCE) MRI is a robust imaging methodology that is commonly used to non-invasively characterize changes in tumor vascularity over time, as a way to assess the therapeutic efficacy of anticancer strategies. With this technique, an intravenously administered bolus of contrast agent is monitored and profiled over a select period of time as it passes through a region of interest [94]. Angiogenic tumor vasculature is known to be very leaky, owing to the fact that they contain large gaps in the endothelial and basement membrane linings of the blood vessels. Therefore, once in circulation, the extravasation of contrast agents from the vasculature is significantly enhanced at these tumor sites. Concentration-time curves can be constructed and characterized by a variety of qualitative and quantitative measures to provide numerical biomarkers that provide physiological insight to changes in the tumor vasculature [95]. Qualitative analysis superficially describes the uptake curves, and typically include calculations of area-under-the-curve, peak enhancement, time to peak enhancement, and maximum upslope [96]. On the other hand, quantitative analysis involves fitting pharmacokinetic models to the data in order to extract parametric values that reflect underlying physiological and anatomical properties of the vasculature. Such measures are extremely valuable due to their insensitivity to variations in the imaging protocol and scanner that may be used in separate studies [97].

However, the ability to quantify the vascular parameters in DCE-MRI relies on the use of a proper gadolinium-based contrast agent for T1-weighted imaging. Traditionally, low molecular weight clinical agents (LMCM) (<1000 Da), such as Gd-DTPA, have been utilized in DCE-MRI studies. Although they are readily excreted through the kidneys, LMCMs are not optimal agents for this imaging technique since they can non-selectively extravasate from both the normal and tumor vasculature. In addition, studies have shown that their extremely high diffusional rates can mask physiological changes in permeability and plasma volume fraction that may occur during anti-angiogenic therapies, limiting the robustness of these vascular parameters as informative biomarkers. Therefore, macromolecular Gd-based contrast agents (MMCM) are preferable for DCE-MRI since their large size (>20 kDa) limits extravasation strictly to the hyper-permeable vessels within the tumor, while also slowing diffusion into the interstitium to make the pharmacokinetic modeling analysis more sensitive to vascular remodeling events. However, there are inherent safety concerns regarding the use of MMCMs since they are too large for renal filtration (>5 nm). Some agents have been shown to persist in the body for several weeks until they are degraded and cleared, and during this time, the Gd ions may dissociate from their chelates to threaten patient safety [98-100].

As a result, a new class of biodegradable polydisulfide Gd(III) macromolecular contrast agents that is excreted more readily than tradition MMCM to alleviate potential toxicity issues was previously developed. Degradation of these polydisulfide contrast agents gradually occurs as endogenous thiols in the blood plasma effectively break the disulfide bonds in their polymeric backbones, facilitating degradation into low molecular weight monomeric subunits for fast renal excretion. In addition, DCE-MRI with such biodegradable macromolecular agents was demonstrated that it provides a more accurate assessment of tumor vascularity and therapeutic response to anticancer treatment than low molecular weight alternatives. However, the reported polydisulfide Gd(III) contrast agents were originally composed of linear Gd-DTPA bisamide subunits, which possess low chelating stability. Therefore, a polydisulfide agent was recently synthesized that incorporated Gd(III) macrocyclic, rather than linear, chelates in order to improve stability. In this study, the latest polymeric contrast agent was further optimized by incorporating smaller monomeric subunits into the backbone to achieve greater T1 relaxivity. The new macrocyclic agent, poly([(Gd-DOTA)-DETA]-co-DTBP) (GODP), is synthesized by covalently attaching DETA-(DOTA-Gd) and dithiobispropionic acid (DTBP) monomers together using NHS ester reaction chemistry.

The applicability of GODP for DCE-MRI evaluation of tumor response to cancer therapy was assessed here in an investigational study exploring the potential anti-angiogenic effects of bumetanide, an FDA approved drug. Bumetanide is an inhibitor of the $Na^+$—$K^+$-$2Cl^-$ (NKCC1) cotransporter, which is responsible for modulating the volume changes in cells. NKCC1 is able to exert such an effect by actively pumping sodium, potassium, and chloride ions into the cells, driving the additional influx of water to maintain osmotic equilibrium. Although bumetanide is a traditional loop diuretic in the clinic, several groups have discovered that bumetanide displays a few features that could ultimately be exploited for cancer therapy.

By blocking the NKCC1 cotransporter, bumetanide has shown the ability to suppress the proper volume regulation required to support tumor growth and migration in an orthotopic glioma model [101.]. Bumetanide is also able to heighten glioma sensitivity to chemotherapeutics by preventing tumor's ability to resist the significant cellular volume loss that occurs at the onset of apoptosis [102]. Lastly, by inhibiting the volume increase that accompanies cell growth and division, bumetanide can effectively slow down the transition between the G1 and S phases of the cell cycle to decrease the overall rate of proliferation [103]. Together, these changes have the potential to greatly affect tumor progression and viability, although there is currently limited information detailing how bumetanide affects the development of various types of tumors.

In this study, the therapeutic efficacy of bumetanide in treating cancer was analyzed by utilizing DCE-MRI, with our in-house GODP contrast agent, to non-invasively evaluate its ability to significantly inhibit angiogenesis and reduce tumor vascularity. A subcutaneous HT29 colon cancer mouse model, which is known to express the NKCC1 cotransporter, was treated with bumetanide on a daily basis over a period of 3 weeks. DCE-MRI was performed weekly throughout the treatment in order to visualize gradual changes in the tumor vasculature. The adiabatic approximation to the tissue homogeneity (AATH) model was used to analyze the DCE-MRI data and calculate blood flow (Fp), permeability-surface area product (PS), and volume fractions of the plasma space (Vp) of the tumor [104, 105]. Histological analysis of CD31 and VEGF expression was performed upon completion of the therapy in order to validate the DCE-MRI parametric analysis. HT29 tumor growth and proliferation were also monitored during this study to determine whether changes in tumor vascularity correlated to changes in tumor burden following bumetanide administration.

Materials and Methods
Materials

Diethylenetriamine (DETA), di-tert-butyl dicarbonate (Boc), N,N-diisopropylethylamine (DIPEA), formic acid, sodium hydroxide (NaOH), 3,3'-dithiobis(sulfosuccinimidylpropionate) (DTSSP), and gadolinium(III) acetate were all purchased from Sigma-Aldrich. Ethyl acetate, hexane, dimethylformamide (DMF), dichloromethane (DCM) and tetrahydrofuran (THF) were purchased from Fisher. Benzotriazol-1-yl-oxytripyrrolidinophosphonium hexafluorophosphate (PyBOP) was purchased from Chem-Impex International, Inc. Primary antibodies for HIF-1α and CD31 were purchase from Novus Biologicals (Littleton, Colo.) and Abcam (Cambridge, Mass.), respectively, while the primary antibody for β-actin was purchased from Cell Signaling (Danvers, Mass.). The secondary antibodies Dk-anti-Rb-HRP and Dk-anti-Rb-Alexa647 were purchased from Jackson ImmunoResearch (West Grove, Pa.). The pimonidazole hypoxia stain was supplied by Hypoxyprobe Inc (Burlington Mass.).

Figure 38:
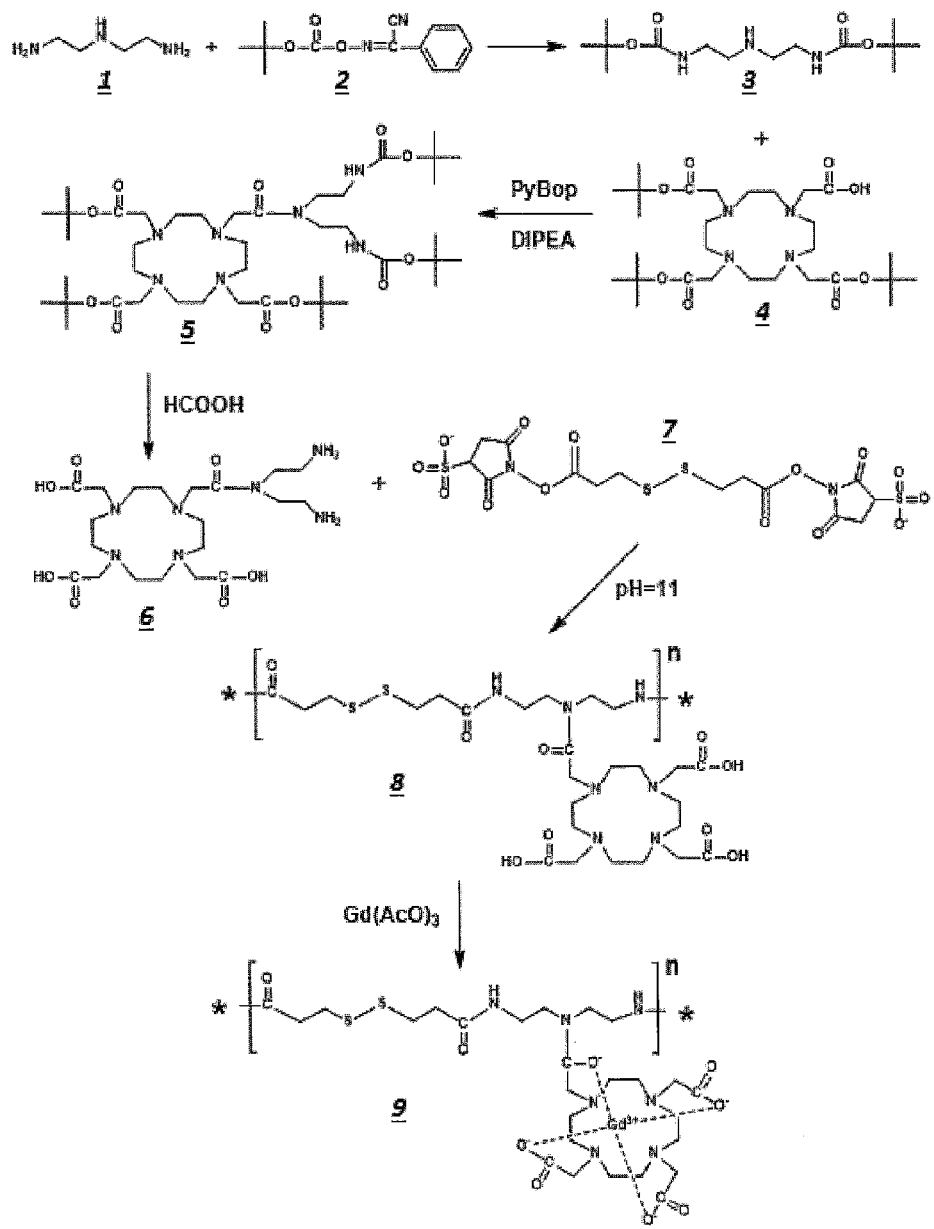
FIG. 38 shows the reaction scheme for the synthesis of GODP macromolecular contrast agent for DCE-MRI techniques.

Synthesis of Poly([(Gd-DOTA)-DETA]-Co-DTBP) (GODP) Macromolecular Contrast Agent The synthetic reaction scheme for the biodegradable macromolecular contrast agent poly(DTSSP-DOTA) is presented in FIG. 38. The following is a detailed description of each step in this process.

Synthesis of DiBoc-DETA:

DETA (1) (1.03 g, 10 mmol) was dissolved in 10 mL anhydrous THF and bubbled with nitrogen for 20 min. At 0° C., a 3× excess of Boc-ON (2), dissolved in 15 mL anhydrous THF, was added drop-wise into the DETA solution. The mixture was stirred at this temperature for another 2 h. The solvent was removed under vacuum and the product DiBoc-DETA (3) was purified using column chromatography with an ethyl acetate:hexane mobile phase at a 1:15 ratio (yield=90%).

Synthesis of DOTA-DETA:

DiBoc-DETA (3) (1.8 g, 5.95 mmol) was dissolved into 20 mL anhydrous DMF. TB-DOTA (4) (1.8 g, 3.14 mmol) was then added into this solution, along with PyBOP (2.45 g, 4.71 mmol) and DIPEA (0.65 g, 4.71 mmol) to catalyze the coupling reaction with DiBoc-DETA (3). After reacting overnight at room temperature the solvent was removed under vacuum and the DiBoc-DETA-DOTA (5) product was purified with column chromatography using an ethyl acetate: DCM mobile phase at a 1:15 ratio (yield=85%). DiBoc-DETA-DOTA (5) (2.0 g) was dissolved into 30 mL formic acid and stirred at 50° C. to remove the Boc protecting groups. Upon completion, the formic acid was removed under vacuum and the DOTA-DETA (6) product was purified with column chromatography using an ethyl acetate: DCM mobile phase at a 10:1 ratio (yield=95%).

Synthesis of poly([DOTA-DETA]-co-DTBP):

DETA-DOTA (6) (0.29 g 0.5 mmol) was dissolved in 0.8 mL DI water. Afterwards, the basicity of this solution was adjusted to pH=11 with saturated NaOH solution. DTSSP (7) (0.35 g, 0.56 mmol) was then added into the DETA-DOTA solution gradually over a 30 minute timespan. The NHS active esters on each end of the DTSSP were allowed to react to the amine groups on both ends of the DETA-DOTA structure at room temperature overnight to form a polymeric structure. FPLC analysis showed that 20% of the resulting product was the poly([DOTA-DETA]-co-DTBP) polymer (8) with a molecular weight of approximately 21 kDa. The polymer was then purified with a PG-50 column (polydispersity index=1.10). Afterwards, the poly([DOTA-DETA]-co-DTBP) polymer was dissolved in DI water and mixed with a 1.5 molar excess of gadolinium(III) acetate.

The acidity of this mixture was adjusted to pH=6, and the reaction proceeded for a total of 12 hours. The pH was monitored every two hours to ensure that the acidity remained constant. Once the complexation reaction was complete, the final product, poly([(Gd-DOTA)-DETA]-co-DTBP) (GODP) (9), was purified with dialysis and then lyophilized.

Relaxation Measurements:

Relaxation rates ($R_1$ and $R_2$) of the GODP contrast agent at five different concentrations were measured on a Bruker Medical Minispec machine at 1.5 T. Longitudinal and transverse relaxivities (r1 and r2) of the polymeric contrast agent equaled the slopes of the linear curves obtained by plotting the measured $R_1$ and $R_2$ relaxation rates versus Gd concentration.

Mouse Model and In-Vivo Tumor Treatment with Bumetanide

The anti-angiogenic effects of bumetanide were investigated in a mouse model bearing subcutaneous HT29 colon adenocarcinoma xenografts. HT29 cells were initially cultured in McCoy's 5A growth media (ATCC), supplemented with 10% FBS, 100 m/mL of streptomycin, and 100 units/mL of penicillin (Invitrogen). A total of $1 \times 10^6$ cells were then inoculated into athymic nude mice in a 250 µL volume of Matrigel (BD Biosciences). Before the start of treatment, tumors were allowed to grow for 10 days, until they were approximately 0.5 cm in diameter. This study comprised of 2 groups of 3 mice, one of which was treated with bumetanide, and the other with a saline control. The drug and saline control were injected intraperitoneally on a daily basis for 3 weeks, with a bumetanide dose of 10 mg/kg. All mice were sacrificed on day 21 of the treatment regimen. Tumor growth was measured at several time points during the therapy with a caliper. Volumes were calculated using the formula $(\frac{1}{6})\pi D_1^2 D_2^2$, where $D_1$ and $D_2$ were two diameters measured along perpendicular axes of the tumor lesion.

DCE-MRI

Changes in the tumor vascularity were monitored during the treatment by DCE-MRI. This imaging technique was performed on each mouse from both groups before the start of the bumetanide and saline therapies to acquire baseline data. The mice were then imaged again on days 7, 14, and 21 during the treatment period. Each mouse was catheterized in the tail vein using a 30 gauge needle that was inserted into a thin tubing approximately 1.5 meters long. The mice were then placed inside the scanner, where they were kept under constant anesthesia using isoflurane. The DCE-MRI acquisition was carried out on a Bruker 7 T system. Once inside the scanner, the mice were properly positioned with the aid of a simple tri-pilot sequence. Afterwards, a set of 17 2D axial images were acquired using a spin-echo sequence to identify the center position of the tumors for the ensuing DCE-MRI. Once these two pre-scans were completed, DCE-MRI acquisition commenced using a 3-dimensional FLASH gradient echo sequence with the following parameters: TR=10 msec, TE=1.05 msec, flip angle=15°, number of averages=1, FOV=3.53 cm×3.53 cm×2.04 cm, and pixel matrix size=128×96×17. The spatial resolution was 0.276 mm×0.368 mm×1.2 mm. Images were acquired for 90 seconds prior to the GODP bolus injection in order to obtain a baseline signal intensity. The contrast agent was then injected manually into the tail vein at a dose of 0.1 mmol Gd/kg in saline (100 µL) within 5 seconds. A total of 400 scans were acquired at a temporal resolution of 4.32 seconds. The entire scan time lasted for 28 min 48 sec.

DCE-MRI Data Analysis Using the AATH Model

After the DCE-MRI was complete, two different slices were extracted from 3D scan were acquired. One slice was selected to analyze the tumor, and the other slice was selected so that it contained a major artery in the body near the tumor tissue. Signal enhancement values ($\Delta$SI) were calculated for each pixel in these slices to account for the change in signal intensity over time by the GODP contrast agent. The general equation $\Delta SI(t)=[S(t)-S_0]/S_0$ was used for this calculation, where S(t) is the signal intensity in the image at time 't' during the DCE scan, and $S_0$ is the average baseline signal intensity during the 90 second scanning period prior to GODP injection. Here, it was assumed that $\Delta$SI was proportional to the GODP concentration, which is a typical approximation when utilizing low concentrations that are within the linear range.

Contrast-enhanced time curves were created for both the tumor and the artery by plotting $\Delta$SI versus scan time. Parametric non-linear curve-fitting was performed in MATLAB to mathematically fit the contrast-enhanced time curves to the AATH model in order to calculate the changes in blood flow, permeability, and plasma volume fraction that occurred during the bumetanide and saline control treatments. The parametric analysis was accomplished using average contrast-enhanced data from ROIs that covered the entire tumors. It was also done on a pixel-by-pixel basis to gather spatial heterogeneity information for each parameter.

Figure 39:
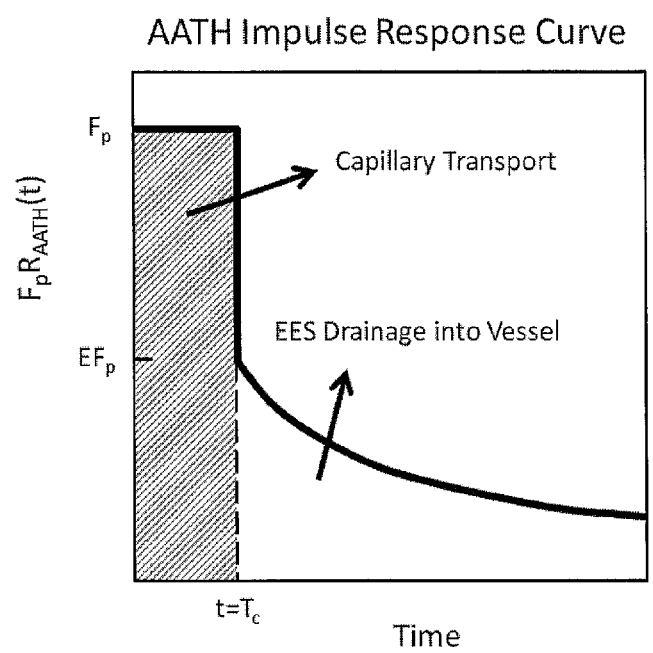
FIG. 39 shows a graphical representation of the AATH impulse response function that was used for DCE-MRI parametric analysis.

The AATH model is a simplified form of its parent tissue homogeneity model, with the approximation that the concentration of contrast agent changes much slower in the extravascular space due to diffusion, than it does in the intravascular space due to blood flow. This assumption decouples the intra- and extra-vascular compartments, and as a result, the impulse response function $R_{AATH}$ (FIG. 39) possesses two separate phases, whereby:

$$R_{AATH}(t) = \begin{cases} 1 & 0 \leq t < T_c \\ E \exp\left\{\frac{-EF_p}{V_e}(t - T_c)\right\} & t \geq T_c \end{cases} \quad (1)$$

Here, the capillary transit time $T_c = V_p/F_p$, and the extraction coefficient $E=1-\exp(-PS/Fp)$. The concentration in the tumor tissue $C_t$ was found by convolving the impulse response function with the arterial input function $C_a$, so that $C_t(t)=F_p C_a(t)*R_{AATH}$. The arterial input function was equal to the contrast-enhanced time curve from the center pixel of the artery.

Immunohistochemistry and Western Blotting

Once the final DCE-MRI scans were complete at the end of the therapy, the mice were intravenously injected with 60 mg/kg of pimonidazole, an established marker for the detection of tissue hypoxia. After one hour following the pimonidazole staining, the tumors from these mice were resected for further biological analysis. Half of each tumor that was collected was snap-frozen in liquid nitrogen for western blot, while the other half was sliced into thin sections and formalin-fixed/paraffin-imbedded for immunohistochemistry (IHC) staining. For western blot, cell lysates from the frozen tissue were prepared by homogenizing entire tumor tissues in RIPA lysis buffer supplemented with a Halt protease inhibitor cocktail (Thermo Fisher Scientific). A total of 50 µg protein from whole tumor lysate was loaded into each well of a 12% TGX gel, and after SDS-PAGE, the separated protein extracts were transferred onto a PVDF membrane (BioRad). The blots were blocked for 1 hr and then stained overnight at 4° C. with primary antibodies for HIF-1α and β-actin, the latter of which serving as the housekeeper control. Image J software was utilized to quantify the relative protein expression of HIF-1α from the blots by calculating the total pixel intensity from each protein band, and then normalizing these signals with its corresponding β-actin stain. Sections of the formalin-fixed tissue were stained with the antibodies for CD31 and the Ki67 nuclear proliferation marker. They were also stained with a primary antibody for the detection of the pimonidazole hypoxia marker. All of the primary antibodies used in this study were produced in rabbits, and were thus paired with donkey anti-rabbit secondary antibodies, either conjugated to a horseradish peroxidase for western blot, or to an AlexaFluor-647 dye for IHC. The primary antibody for pimonidazole was conjugated to a FITC label, and therefore did not require a secondary antibody.

Statistical Analysis

Statistical analyses were performed using unpaired two-tailed Student's t-tests with a 95% confidence interval, assuming equal variances. Probability values of p<0.05 were considered to be significant. Mean data values from this study are reported with their standard deviations (mean±SD).

Results

Synthesis of Biodegradable GODP Polymer

The biodegradable macromolecular contrast agent GODP was synthesized according to the reaction scheme in FIG. 38. DETA was first conjugated to the macrocyclic ligand DOTA to give DOTA-DETA, which possesses two available primary amine groups for polymerization. DOTA-DETA was then copolymerized with the disulfide-containing active ester monomer DTSSP to obtain the polymer poly(DOTA-DETA-co-dithiobispropionic acid). The final contrast agent poly[(Gd-DOTA)-DETA-co-dithiobispropionic acid] (GODP) was then synthesized by complexing the polymer with Gd(III). The number and weight average molecular weights of GODP were XX and XX kDa, and its r1 and r2 relaxivities were 11.45 and 13.09 mM-1 s-1 per Gd(III) at 1.5 T, respectively.

DCE-MRI Assessment of Tumor Vascularity

Figure 40:
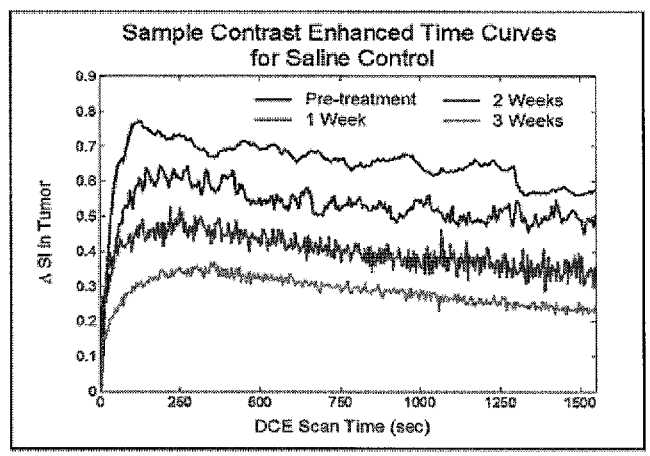
FIG. 40A-C shows contrast enhanced-time curves related to the study The images in (FIG. 40A) and (FIG. 40B) are contrast-enhanced time curves obtained from a representative mouse in the saline control and bumetanide-treated groups, respectively. The contrast enhanced-time curves in (FIG. 40C) were obtained from all of the mice in this study at the 3-week time point and show that the tumor uptake of GODP contrast agent is significantly compromised by the bumetanide therapy, suggesting a regression in vascularity.
Figure 40:
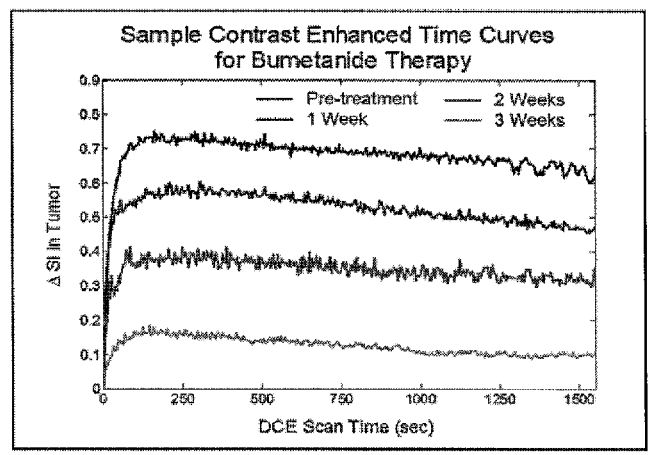
Figure 40:
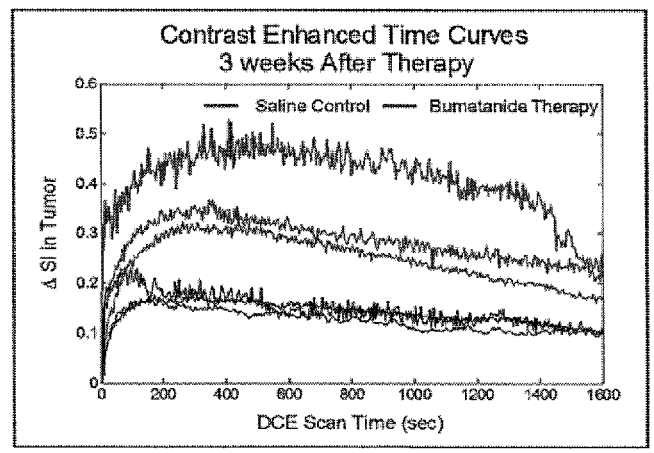

DCE-MRI data were acquired on a weekly basis both before and after the start of the bumetanide and saline treatments for a total of 3 weeks. Contrast-enhanced time curves were constructed from the DCE-MRI data by plotting the average signal enhancements for regions-of-interest covering the entire tumor for each individual mouse. FIG. 40A shows a representative set of contrast-enhanced time curves that were acquired at each weekly imaging time point for a single mouse in the saline control group, while FIG. 40B displays a similar set of time curves for a mouse treated with Bumetanide instead. In addition, FIG. 40C displays the final contrast-enhanced time curves that were obtained from all the mice in both groups at the completion of the 3-week treatment period. From the peak enhancements of these images, it is evident that the degree of GODP contrast agent uptake was significantly lower in the bumetanide-treated tumors than in the control tumors, suggesting that the tumor vascularity is significantly reduced by the bumetanide therapy.

Figure 41A:
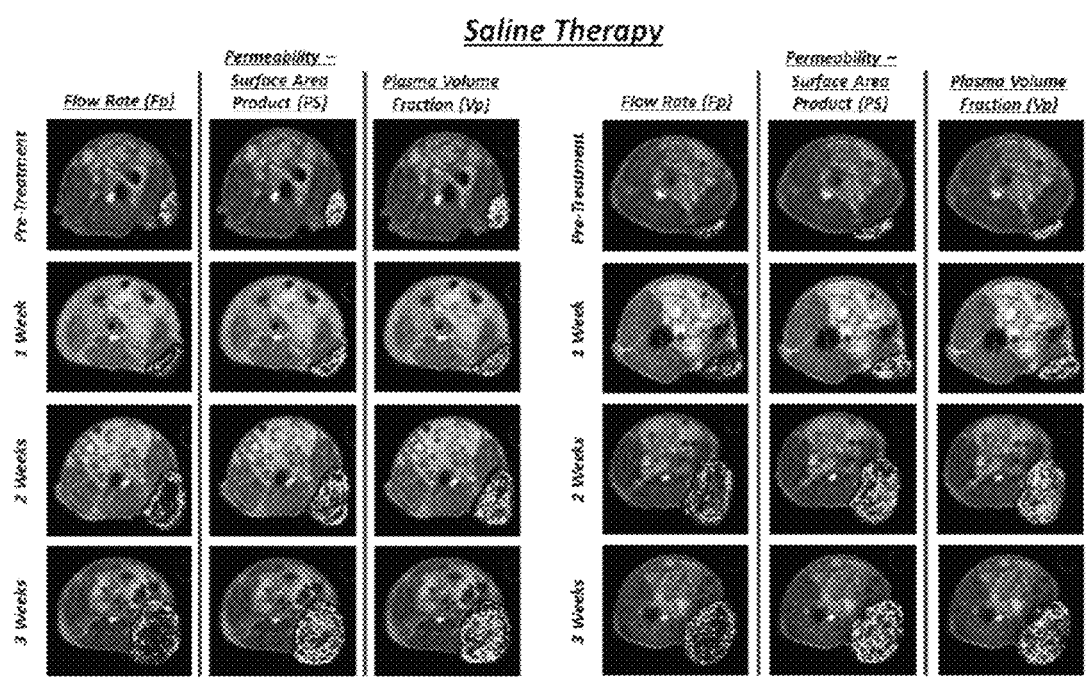
FIG. 41A-B shows parametric mappings were constructed by applying the AATH model on a pixel-by-pixel basis.

The AATH tracer kinetic model (Eq. 1, FIG. 39) was then parametrically fitted to the DCE-MRI data in order to quantitatively characterize how the bumetanide therapy compromised the vascular network, both anatomically and physiologically, in comparison to the control. The blood flow rate (Fp), permeability-surface area product (PS), and fractional plasma volume (Vp) parameters of the tumor vasculature were all calculated not only on a pixel-by-pixel basis, but also on a macroscopic level using average signal intensity data from regions-of-interest spanning entire tumor areas. FIGS. 41A&B shows a time-course of Fp, PS, and Vp pixel mappings from two representative mice in each treatment group. These images demonstrate a significant anti-angiogenic effect of the bumetanide therapy.

Prior to the start of treatment, each tumor lesion was uniformly well perfused (Fp) and well vascularized (Vp), while also exhibiting high permeability (PS). By the end of the three week period, the control mice maintained a similar spatial pattern in the PS and Vp mappings, suggesting significant vascular coverage and permeability throughout the lesion (FIG. 41A). However, there appeared to be a significant reduction in Fp in the tumor interior, as the values of this parameter were much greater along the tumor periphery.

Figure 41B:
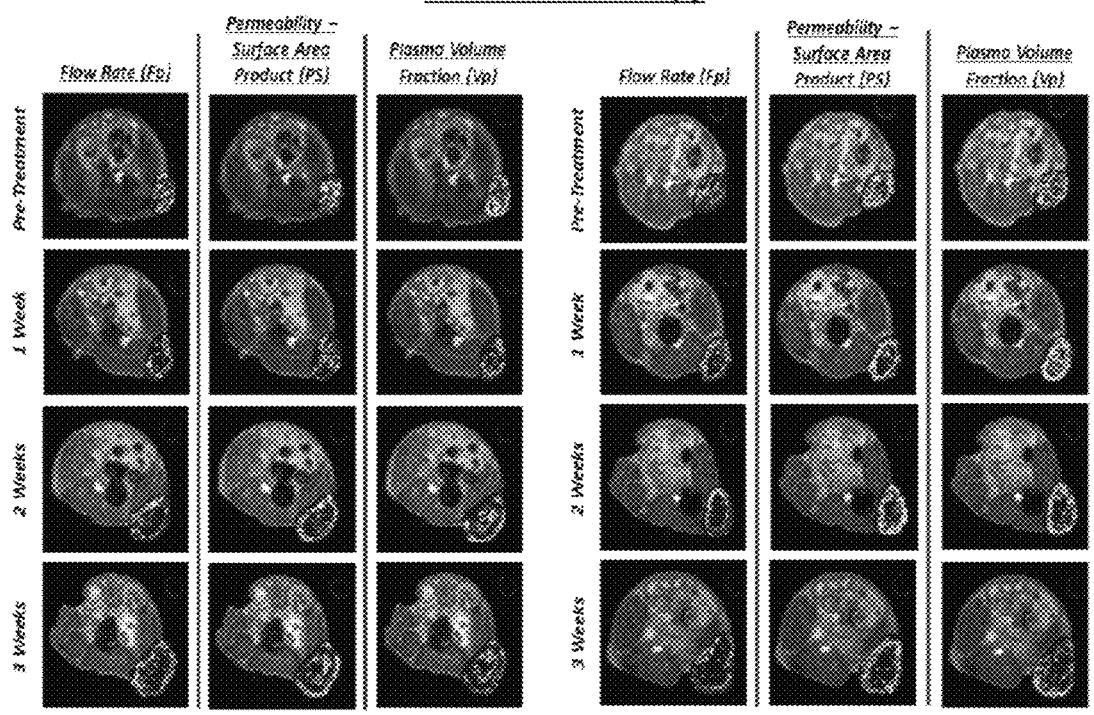

Meanwhile, the bumetanide-treated mice did not show this same result, as seen from the mappings in FIG. 41B. Here, it appears that after 2 weeks of the bumetanide treatment, the PS and Vp parameters both significantly declined in each of the tumor cores, with most of the remaining angiogenic activity limited to the tumor periphery. The changes observed in these parametric spatial distributions demonstrate the gradual vascular regression that occurs over time, to the point of near collapse in the interior microenvironment of the tumor tissue. Nevertheless, by the end of the 3-week treatment period, it was also consistently observed a significant reduction in the Vp mappings along the tumor periphery, although this was not necessarily the case for PS parameter. Despite the observed differences in the PS and Vp mappings between the two treatment groups, the Fp mappings from the bumetanide therapy appeared to be similar to those of the saline control therapy, thus demonstrating that the majority of the blood flow was concentrated to the outer rim of the tumor lesions, regardless of the administered treatment.

Figure 42:
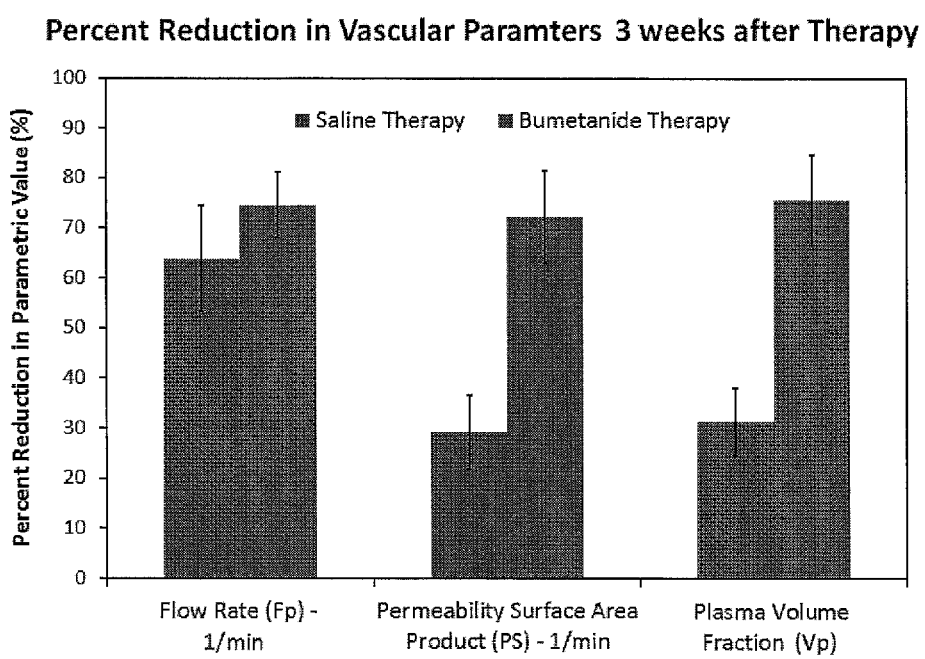
FIG. 42 shows average parametric values were obtained from the DCE-MRI analysis using the AATH tracer kinetic model. This figure shows the percent reductions between the pre- and post-treatment levels of each parameter. As seen here, the bumetanide therapy was able to induce significantly greater reductions in the PS (p=0.003) and Vp (p=0.002) parameters over the course of the 3-week treatment period as compared to the saline control therapy. However, no significant differences were observed in the flow rate.

Average parametric values for the entire tumor lesions at the 3-week time point are presented in FIG. 42. These results show that although both the control and bumetanide groups induced a decline in the average PS and Vp parameter levels in relation to their respective pre-treatment levels, the bumetanide therapy was able to induce greater reductions in these parameters compared to the control therapy. It was determined that the average reduction in PS and Vp was 29.2±7.39% and 31.3±6.71%, respectively, for the control group, while the bumetanide therapy was able to induce reductions of 72.2±9.26% and 75.6±8.97%, indicating that the latter had a significantly greater inhibitory effect on tumor vascularity (p=0.003 for PS and p=0.002 for Vp). These results also support the parametric mappings from FIG. 41A and FIG. 41B, which showed that the magnitudes of both PS and Vp were significantly lower in the tumor cores following administration of the bumetanide therapy.

On the contrary though, a similar trend was not observed in the Fp parameter from FIG. 42. The average value for this parameter decreased between pre- and post-treatment levels by 63.9±10.6% in the control group and 71.2±8.01% in the bumetanide group (p=0.397). However, this lack of a significant difference is in congruence with the Fp mappings in FIGS. 41A&B, which revealed that the spatial distributions and magnitudes of perfusion were not noticeably different between the two treatments.

Bumetanide Reduces CD31 and VEGF Expression in Tumor Tissue

After the 3-week therapies were complete, IHC analysis of the tumor vasculature revealed a significant decrease in CD31 expression following bumetanide administration, suggesting a regression in the blood vessel network. The images in FIG. 43A demonstrate that the number of vessels in both the tumor periphery and core regions is significantly lower in the bumetanide group than in the control group. The apparent vascular regression observed here supports the reduction in the average Vp parameter obtained from the DCE-MRI analysis in FIG. 42. In addition, the lack of substantial CD31 expression in the core tissue of the bumetanide-treated tumors is also strongly related to very low levels observed in the Vp parametric mappings of FIG. 41B.

Not surprisingly, the decrease in CD31 expression coincided with an elevation in tumor hypoxia levels. This is evident by the increased intensity in the representative pimonidazole stainings displayed in FIG. 43B. An increase in hypoxia following bumetanide therapy was expected, given that severe regression of the vascular network limits its ability to deliver oxygen throughout the tumor tissue.

Figure 44:
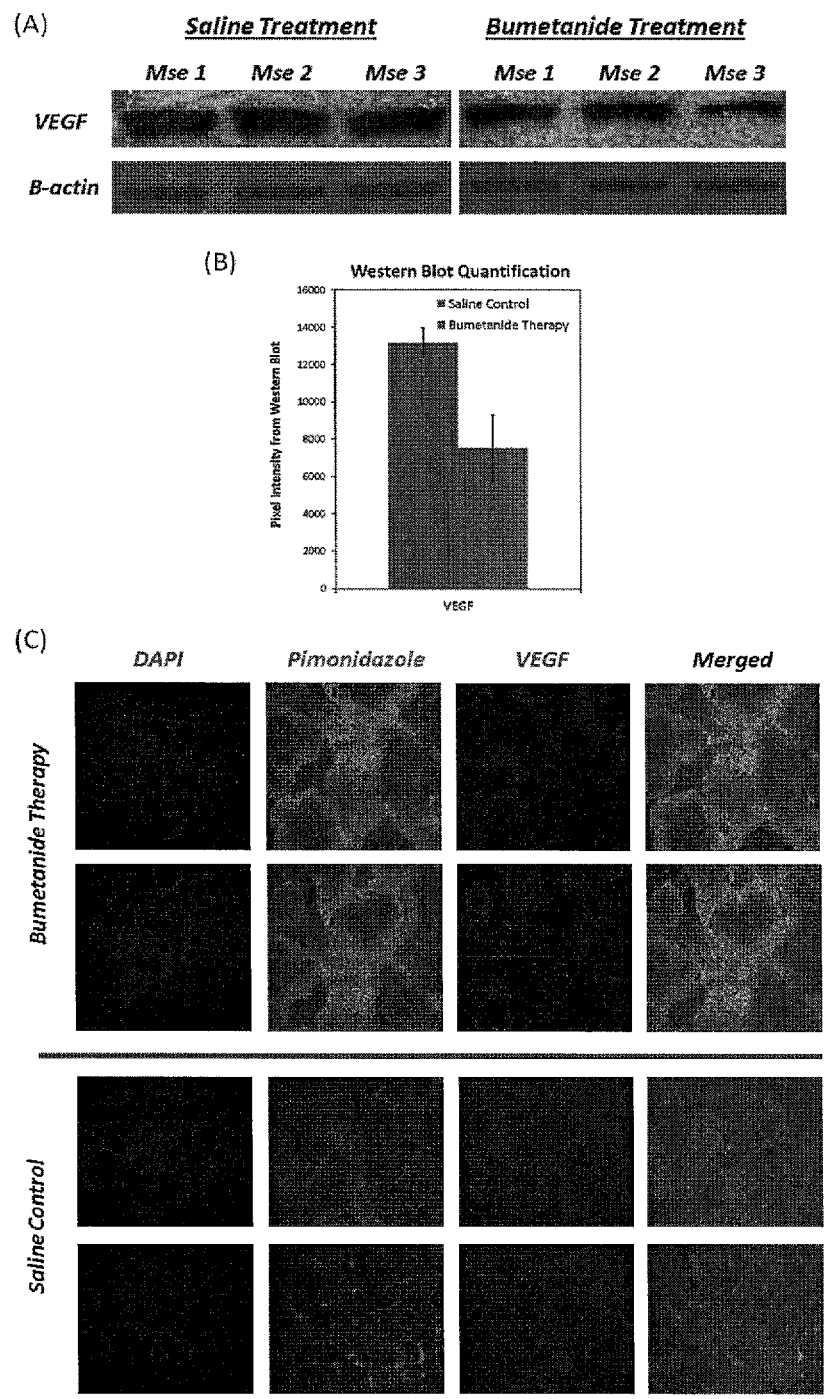
FIG. 44A shows Western blot data.
FIG. 44B reveals that VEGF expression was 42.9% lower in the bumetanide-treated tumors after 3 weeks of therapy, in comparison to the control tumors (p=0.021).
FIG. 44C shows IHC images in support this result and show that, much like CD31, a decrease in VEGF expression is associated with greater levels of hypoxia.

Similar to CD31, it was also discovered through western blot and IHC that VEGF, a common pro-angiogenic growth factor in tumors, was also significantly reduced in response to the bumetanide therapy compared to the saline control. The results in FIG. 44 show that VEGF protein levels were 42.9% lower, on average, in the bumetanide-treated group upon completion of the 3 week treatment period (p=0.021). The reduction in this angiogenic promoter may constitute a reason for the decline in CD31 expression and blood vessel coverage in response to the bumetanide therapy.

Tumor Growth Rate and Ki67 Expression Remain Unchanged after Bumetanide Therapy

Figure 45:
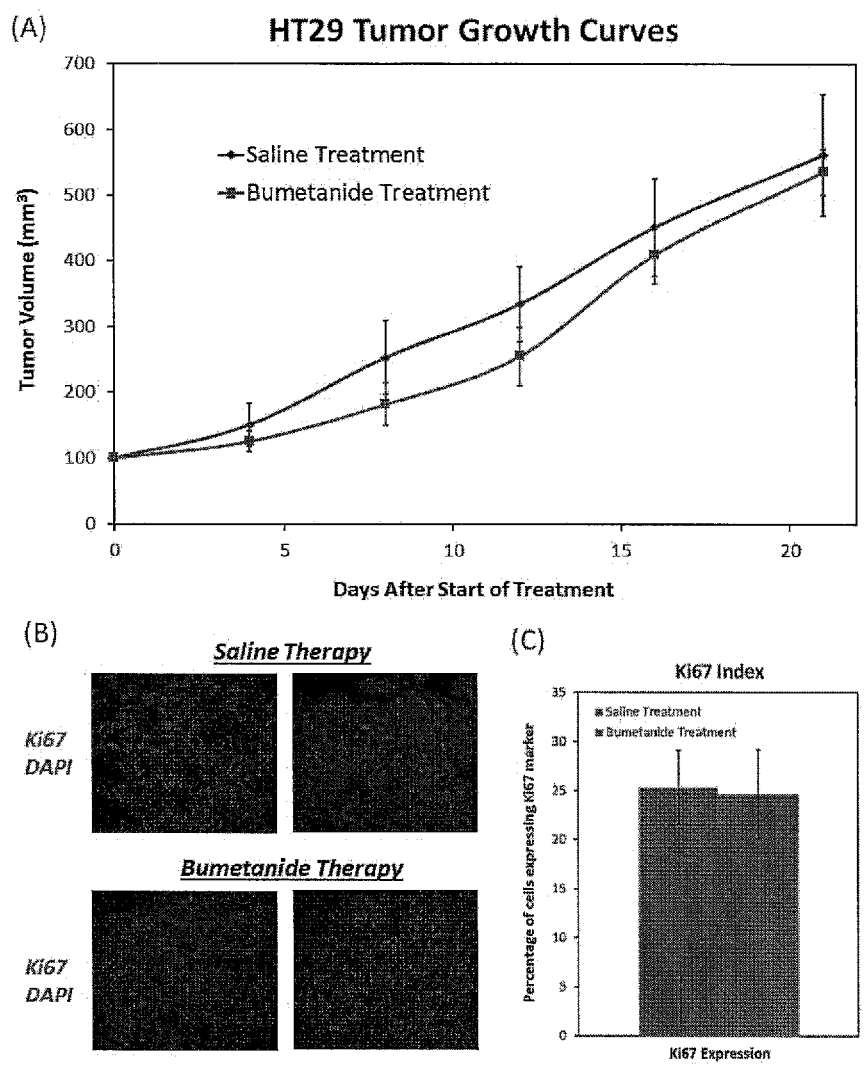
FIG. 45A shows the bumetanide therapy did not exhibit any effects on tumor growth and proliferation. Tumor size remained unchanged during the course of the treatment period in comparison to the control tumors.
FIGS. 45B&C shows IHC staining of the proliferation marker Ki67 also did not show a significant difference between the two groups (FIG. 45B and FIG. 45C).

Despite the fact that bumetanide inhibited angiogenesis and induced vascular regression, the therapy was not able to slow down the tumor growth rate over the course of the study. The growth curves in FIG. 45A show that no significant difference in tumor size was observed between the bumetanide-treated and saline control groups at any point during the 3-week administration period. In support of this result, IHC analysis revealed that expression of the nuclear cell proliferation marker Ki67 also did not change in response to the bumetanide therapy, which can be seen in FIG. 45B. Ki67 is a nuclear protein that is minimally expressed in quiescent cells, and undergoes a progressive increase until it reaches a maximum level during mitosis. Therefore, expression of this protein is widely used as a biomarker to determine the proliferative capacity of a tumor. A Ki67 index was calculated by determining the percentage of nuclei in a given area of the tissue expressed this factor. As a result, it was found that the Ki67 was approximately 25.3±3.79% and 24.7±4.51% for the control and bumetanide-treated tumors, respectively, suggesting that the tumors in each group were equally proliferative (FIG. 45C).

Bumetanide Increases HIF-1α Expression in Tumor Tissue

Figure 46:
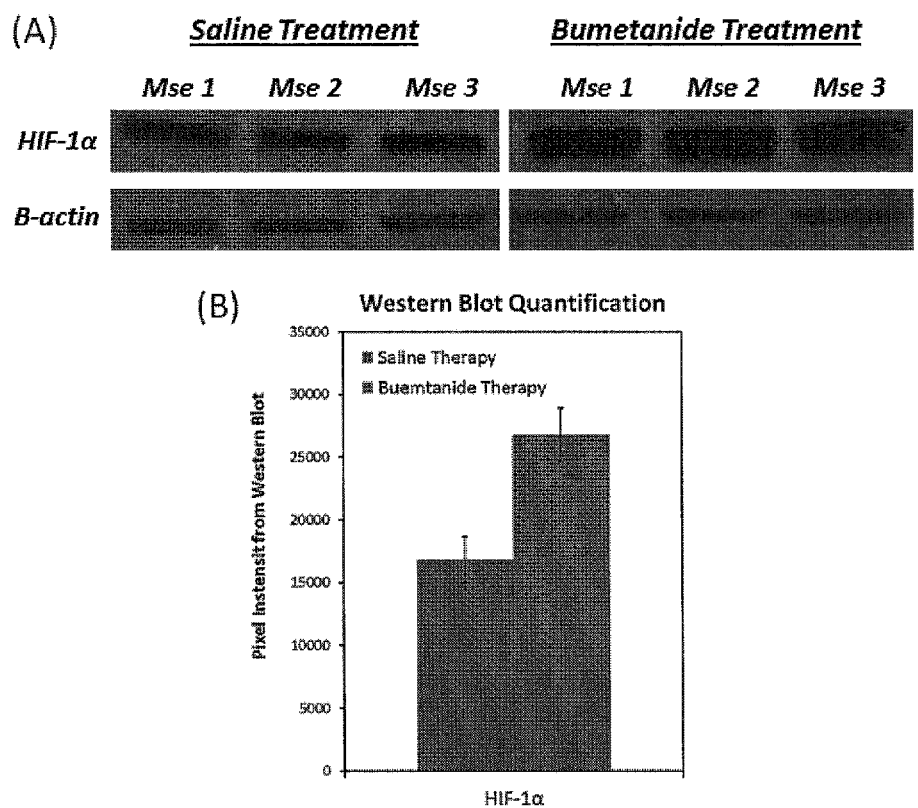
FIG. 46 shows a Western blotting showed that the HIF-1α expression was 59.1% greater in the bumetanide-treated tumors than in the control tumors (p=0.003). The increase in this transcription factor coincides with the increase in tumor hypoxia, as shown in FIG. 43.

Intuitively, the sustained tumor growth and proliferation was observed in response to the bumetanide therapy appears to be contradictory to its inhibitory effects on vascularity. When the blood vessel network is compromised in tumors, the lesions are unable to grow more than 1-2 mm3 in size due to an inadequate supply of nutrients and oxygen. However, a variety of tumor types are able to circumvent the inhibitory growth effects of an insufficient angiogenic network by initiating the hypoxia response pathway and stabilizing the HIF-1α transcription factor under low oxygen conditions. HIF-1α then promotes a number of adaptive measures that function to protect the tumor, and even instill greater invasive properties. After discovering an increase in tumor hypoxia, the tumor tissue was analyzed using western blot analysis and found that the bumetanide therapy increased the expression of HIF-1α by an average of 59.2% (p=0.003), relative to the protein levels that were observed in the saline control mice (FIG. 46). Such an increase may be may be the reason why bumetanide was unable to reduce the tumor growth rate, even though it was found to inhibit angiogenesis.

Discussion

In this study, a novel biodegradable macromolecular MRI contrast agent was developed that optimizes DCE-MRI techniques for accurate evaluation of tumor angiogenesis in response to a cancer therapy. This method has developed into a popular alternative to a more common and traditional approach of characterizing the angiogenic network of tumors that involves the use of a biopsy to calculate a histological estimate of microvascular density (MVD). Although the MVD biomarker has exhibited a correlation with the frequency of tumor metastasis and decreased survival time in a variety of cancers, it possesses several significant limitations for clinical application. This measurement is inherently invasive by requiring an intact tissue sample, fails to capture the spatial heterogeneity of the vascular network, and does not provide any functional information, such as the flow and permeability through these vessels. The latter limitation is especially important considering that only a fraction of tumor blood vessels are able to actively transport blood throughout the tumor tissue [106, 107].

The development of medical imaging modalities offers the opportunity to overcome the problems associated with MVD by providing the ability to periodically, yet non-invasively, monitor the angiogenic progression of tumors in vivo, throughout the entire lesion, as a way of evaluating the response to drug therapy [108]. Such prognostic tools have been shown to uncover anti-angiogenic effects in the vascular network within the first week of treatment, much before any reductions in tumor growth can be observed [109]. As a result, the use of imaging modalities can provide an enormous benefit for the identification of non-responders at the beginning stages of treatment, allowing physicians to determine if therapeutic strategies need to be altered at earlier points.

Among the many imaging modalities that are currently used in the clinic, MRI offers great potential for imaging angiogenesis since it is widely available, has good spatial resolution, and does not involve radiation exposure. In particular, DCE-MRI is a powerful technique that has the ability to capture changes in the angiogenic network by profiling the passage of a contrast agent bolus through tumor tissue. After data acquisition, pharmacokinetic compartment models can be applied to the concentration curves in order to extract physiological and anatomical information of the vascular network that cannot be captured from MVD measurements alone [110, 111]. When the adiabatic approximation to the tissue homogeneity (AATH) model is utilized, as done in this study, such information includes estimates of blood flow (Fp), permeability-surface area product (PS), and volume fraction of the plasma space (Vp). Changes in these vascular parameters during the course of an anti-cancer therapy have been shown to correlate with MVD density measurements and tumor growth inhibition in order to provide a robust diagnostic technique for disease management [112]. This reflects the fact that the extent of vascularization exhibits a strong relationship to both tumor grade and malignancy.

Traditional MRI contrast agents, such as Gd-DTPA chelates, with molecular weights less than 1 kDa, have been widely used for DCE-MRI protocols due to their clinical availability. However, their small size facilitates non-selective extravasation from both tumor and normal vasculature, leading to large first-pass extraction. On the other hand, macromolecular contrast media (MMCM), with molecular weights over 20 kDa, are not able to permeate through the vessel walls of normal vasculature. Instead, their rather large hydrodynamic diameters limit their extravasation through only hyperpermeable blood vessels of the tumor, albeit at a significantly reduced rate compared to low molecular weight agents. As a result, preclinical studies have shown that DCE-MRI performed with MMCMs can detect subtle changes in vascular parameter estimations that are not revealed by lower molecular weight alternatives with much greater wash-in and wash-out rates. Unfortunately, MMCMs are not readily excreted by the kidneys since they are generally greater than the 5 nm cutoff size for glomerular filtration. As a result, elimination of these agents are rather slow, and their prolonged retention in the body can persist for several weeks, potentially leading to toxic side effects [106, 113].

In recent years, the design of a novel class of biodegradable macromolecular contrast agents for DCE-MRI analysis has been explored. Such agents possess accelerated clearance profiles because they can readily degrade, following the completion of an imaging protocol, into low molecular weight subunits that are readily removed by the kidneys. Previous studies with Avastin have shown that our biodegradable contrast medium is also able to improve the accuracy of DCE-MRI parameter estimation, enhancing the characterization of progressive tumor vascularity changes. The new agent synthesized here, GODP, was a polymeric construct, around 21 kDa in size, with monomeric subunits that contained reducible disulfide bonds. Degradation and renal clearance was mediated through the disruption of these disulfide bonds in the presence of endogenous thiols during circulation. Macrocyclic DOTA chelators were also incorporated into the monomeric subunits, in place of the linear DTPA chelators was previously utilized, in order to improve the stability of Gd complexation and make this new macromolecular agent more desirable for in-vivo applications.

The GODP contrast agent was utilized in a DCE-MRI study that investigated the potential anti-angiogenic properties of the FDA approved drug bumetanide, an inhibitor of the $Na^+$—$K^+$-$2Cl^-$ (NKCC1) cotransporter. NKCC1 is ubiquitously expressed in most tissue types, aiding in cell volume regulation by pumping sodium, potassium, and chloride ions into the cell, along with osmotically obligated water. Historically, this drug has only been used as a loop diuretic in the clinic to treat hypertension and edema. However, the results from several earlier publications demonstrate the potential benefits this drug may have for cancer therapy.

Most notably, an orthotopic glioma study by Haas and Sontheimer revealed that bumetanide was able to inhibit the growth, cell migration, and invasion of glioma tumors. This effect was attributed to the fact that tumor cells require NKCC1 to localize to the leading edge of their invading processes and regulate the volume changes that are necessary to enable migration through tight extracellular spaces of the tumor interstitium. Therefore, inhibition of NKCC1 activity played a major role in preventing glioma cell dispersion away from the primary tumor mass [101]. Another glioma study by Algharabil et al. revealed that bumetanide was able to effectively enhance sensitivity to the chemotherapeutic drug temezolomide, inducing significant cell death. One of the major hallmarks of apoptotic events is a significant reduction in cell volume, resulting from a loss of $K^+$ and $Cl^-$ ions. However, by possessing the NKCC1 transporter, tumor cells are able to counteract such loss in ionic strength and pump water back into the cell, thus maintaining volume homeostasis and evading the induction of apoptosis, by chemotherapeutics. Therefore, blockage of the NKCC1 transporter with bumetanide inhibits this resistance pathway and facilitates the ensuing cell death mechanisms [102]. Lastly, studies have also demonstrated that bumetanide-mediated inhibition of the NKCC1 cotransporter can reduce the proliferation of human skin fibroblasts, bovine endothelial cells, rat vascular smooth muscle cells, and human lung cells in culture by inhibiting the regulatory volume increase necessary for the transition between the G1 and S phases of the normal cell cycle [103].

Although bumetanide has not been widely investigated for tumor therapy, the above studies show that this drug induces several downstream biological effects that reduce cellular growth and viability, which may be exploited for successful cancer treatment. As a result, it was hypothesized that blockage of the NKCC1 transporter with bumetanide would suppress proper volume regulation in the tumor cells, causing a reduction in cellular migration and proliferation, while also affecting tumor cell viability by increasing the sensitivity and susceptibility to apoptosis. In turn, this would ideally slow tumor growth, and subsequently hinder expansion of the vascular network. Nevertheless, blockage of NKCC1 could even induce a direct anti-angiogenic effect since bumetanide has also exhibited the potential to alter the growth of endothelial cells. It was anticipated that DCE-MRI imaging with the GODP contrast agent would be able to correlate changes in the tumor vasculature with changes in the overall growth rate. If successful, this agent could be used to provide an effective early, yet non-invasive, indication of tumor responsiveness to a multitude of other anti-cancer therapies.

In this study, the anti-angiogenic efficacy of bumetanide was investigated using an HT29 colon tumor model since literature has shown that this type of cancer possesses the NKCC1 cotransporter. Daily administration of the Bumetanide drug and a saline control lasted for 21 days after the start of the treatment. By performing weekly DCE-MRI scans of each mouse, the progressive changes in tumor vascularity was able to characterized throughout the entire study. As presented in FIG. 42, significant decreases in the average parametric values for Fp, PS, and Vp were observed for both treatments groups in comparison to their respective pre-treatment levels. However, relative to the control group, the bumetanide therapy was significantly more effective at reducing Vp and PS. Such changes are clearly supported by the representative parametric mappings in FIGS. 41A&B. Here, the pre-treated tumors from both the control and bumetanide groups displayed a rather uniform vascular network, possessing high Vp and PS levels throughout the tumor lesion. However, during the 3-week treatment period, the magnitude of these values not only declined at a faster rate in the bumetanide-treated tumors, but their spatial distributions appeared to differ as well. From the Vp and PS parameter mappings, it appears that the tumor vasculature severely regressed in the core regions of only the bumetanide treatment group, and not the control. Together, the greater reductions in these two vascular parameters, relative to the saline control, suggest that bumetanide is able to significantly induce anti-angiogenic effects in HT29 tumor tissue.

Figure 43:
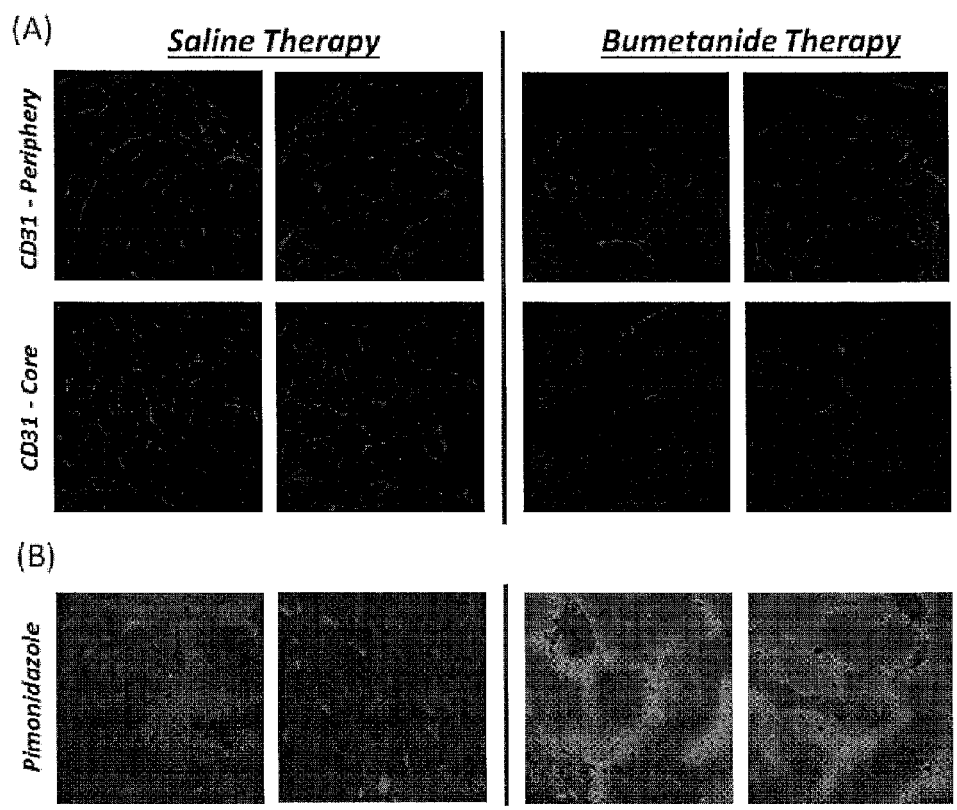
FIG. 43A shows IHC stains for CD31 expression reveal that vascularity is significantly compromised in both the periphery and core tissue of the bumetanide-treated tumors, compared to those treated with the saline control.
FIG. 43B shows pimonidazole staining of samples of both saline and bumetanide therapies. Not surprisingly, the decrease in CD31 coincided with an increase in tumor hypoxia, as evidenced by the increase in pimonidazole staining intensity.

Interestingly though, a significant difference was not observed in the average Fp parameter between the control and bumetanide therapies after the 3-week treatment period. Considering that bumetanide caused the Vp and PS parameters to regress in comparison to the control, it was expected that the average Fp would be lower as well. However, this was not case, as both treatments actually resulted in a substantial decrease in Fp throughout the tumor cores during the course of the study (FIGS. 41A&B). As a result, unlike the Vp and PS parameters, Fp did not prove to be a good prognostic indicator of anti-angiogenic activity for bumetanide. The percent reduction in Fp from pre-treatment levels, following the bumetanide therapy, was similar to that of the Vp and PS parameters, and therefore, was a reflection of the decline in tumor vascularity. Unfortunately the reduction in Fp was statistically the same for the control treatment, but potentially for a different reason. Since Vp and PS levels were greater in the controls, the presence of low flow in these tumors was likely not due to a vascular regression, but instead due to high interstitial pressures that collapse the blood vessels within the rapidly growing tumor mass In order to validate the parametric analysis, and thus the effectiveness of our new biodegradable, macromolecular GODP contrast agent for DCE-MRI, tissue sections were stained for CD31 expression as a way to directly visualize changes in the number of blood vessels. As seen in FIG. 43, the control tumors possessed a more extensive vascular network than their bumetanide-treated counterparts by the completion of the study, correlating with the changes observed in the Vp parameter from DCE-MRI analysis. This result demonstrates that the application of GODP for DCE-MRI is able to facilitate accurate assessment of tumor vascularity, and can ultimately aid in providing a strong indicator of tumor malignancy and therapeutic performance. Since angiogenesis is usually a strong indicator tumor malignancy, the application of this contrast agent for dynamic imaging can potentially eliminate the need to acquire biopsies for evaluating the performance of cancer therapies.

Although the bumetanide drug was effective at inhibiting angiogenesis, it did not necessarily correlate with the reduction in tumor growth curve and Ki67 proliferation index that was originally anticipated. It is possible that the greater levels of tissue hypoxia, and subsequent elevation of HIF-1α, were the major contributors to the unimpeded tumor expansion observed, despite the apparent reduction in vascularity. HIF-1α is a transcription factor that is constitutively expressed in cancer cells, but constantly degraded by prolyl hydroxylases in normoxic, well-oxygenated microenvironments. Under hypoxia, HIF-1α is stabilized and induces the transcription of a variety of downstream genes, many of which play an essential role in preserving cell survival, metabolism, and proliferation under low oxygen tension. In fact, many studies have reported the failures of anti-angiogenic therapies, including Avastin, due to the compensatory up-regulation of HIF-1α.

One of the primary roles of HIF-1α in cancer cells is to counteract the onset of tissue hypoxia by inducing angiogenesis to restore tumor growth and exacerbate invasion and metastasis. HIF-1α increases tumor vascularity through the production and secretion of several pro-angiogenic factors, the most prominent of which is VEGF. However, the opposite effect was observed in this study, whereby an increase in HIF-1α expression was instead accompanied by a decrease in VEGF levels during the 3-week bumetanide therapy. This suggests that bumetanide was able to subdue angiogenic activity through an off-target inhibitory effect on VEGF production in HT29 tumor cells. It is widely known that VEGF production is affected by multiple signal transduction pathways in tumor cells, and it is possible that bumetanide may interact any of these mechanisms to regulate the expression of this pro-angiogenic growth factor.

In the future, a more complete biological investigation needs to be conducted in order to verify if such a phenomenon exists, and whether or not it is ultimately responsible for the significant anti-angiogenic behavior of bumetanide. It is well known that VEGF is not only produced and secreted by tumor cells, but also by other stromal cells in the highly active microenvironment, including fibroblasts and tumor associated macrophages. Nevertheless, VEGF can also be secreted by endothelial cells as part of an autocrine signaling loop that is required for vascular homeostasis. Considering that VEGF can originate from a number of secondary sources within the microenvironment, a systematic analysis must be completed to determine if NKCC1 cotransporter inhibition from bumetanide affects the integrity of stromal and endothelial cells, and ultimately how their abilities to produce VEGF are compromised. As noted earlier, studies have revealed that bumetanide can impair the normal volume increase required for proper progression through the cell cycle. Any delays in the stromal and endothelial cell cycles may diminish the degree at which these two cell types can produce VEGF and support tumor angiogenesis.

Although it appears that that bumetanide was not effective at reducing tumor growth, its anti-angiogenic capabilities can be exploited in combination treatment regimens as a supplement to more traditional cytotoxic chemotherapeutic drugs. Combination therapies are currently gaining momentum as a new strategy to treat tumors in order to prevent the onset of resistance and to achieve long-term efficacy. Many studies have shown that the incorporation of anti-angiogenic agents into combination strategies is able to increase response rates and prolong survival in cancer patients. As a result, with further understanding and optimization of its anti-angiogenic capabilities, bumetanide may potentially be employed an advantageous drug candidate for future cancer therapies.

CONCLUSION

In conclusion, this investigative study demonstrated and validated the use of GODP as an efficient polymeric, biodegradable, macromolecular contrast agent for DCE-MRI applications. With the aid of the AATH pharmacokinetic model, this agent was shown to be able to reveal the anti-angiogenic activity of the NKCC1 inhibitor bumetanide. After 3 weeks of daily injections, bumetanide was able to induce a significantly greater decline in the vascular permeability and plasma volume fraction of HT29 xenografts compared to that achieved by the saline control therapy. The decline in tumor vascularity was verified by concurrent reductions in the CD31 and VEGF expression within the tumor tissue. This subsequently led to an increase in tumor hypoxia and HIF-1a expression, likely contributing to the observation that tumor growth and proliferation did not subside. Since HIF-1α typically induces VEGF expression, it is possible that bumetanide reduces tumor vascularity by inhibiting the production of this angiogenic growth factor. Future work is necessary to uncover the complex biology events responsible for VEGF inhibition and to optimize the use of this drug for combination therapies.

REFERENCES

1. Stahl, P. H. and Wermuth, C. G, (Eds.) (2002) *Handbook of Pharmaceutical Salts: Properties Selection and Use*, Verlag Helvetica Chimica Acta/Wiley-VCH, Zurich.

2. Cai, J. et al. "Identifying Molecules Modulating Protein-Protein Interaction," WIPO PCT Patent Publication Number WO/2009/032716, Application PCT/US2008/074543, filed Aug. 28, 2008. (published Mar. 12, 2009).
3. Allen, T. M. and Cullis, P. R. (2013) "Liposomal drug delivery systems: From concept to clinical applications," *Adv. Drug Delivery Rev.* 65(1), 36-48.
4. Madhu, M. et al. (2009) "Biodegradable Injectable Implant Systems for Sustained Delivery Using Poly (Lactide-Co-Glycolide) Copolymers," *Int. J. Pharm. Pharm. Sci.* 1(1), 103-107.
5. Tsutsui, J. M. et al. (2004) "The use of microbubbles to target drug delivery," *Cardiovasc. Ultrasound* 2, 23.
6. Sirsi, S. and Borden, M. (2009) "Microbubble Compositions, Properties and Biomedical Applications," *Bubble Sci. Eng. Technol.* 1(1-2), 3-17.
7. Elger, G A. et al. "Controlled release pharmaceutical composition," U.S. Pat. No. 4,828,836, application Ser. No. 07/052,580, filed May 19, 1987. (issued May 9, 1989).
8. Van Lengerich, B. H. "Embedding and encapsulation of controlled release particles," U.S. Pat. No. 6,190,591, application Ser. No. 09/269,763, filed May 17, 1999. (issued Feb. 20, 2001).
9. Wu, H. et al. (2009) "Dynamic Evolutionary Changes in Blood Flow Measured by MDCT in a Hepatic VX2 Tumor Implant over an Extended 28-day Growth Period: Time-Density Curve Analysis," *Acad. Radiol.* 16(12), 1483-1492.
10. Keunen, O. et al. (2011) "Anti-VEGF treatment reduces blood supply and increases tumor cell invasion in glioblastoma," *P.N.A.S.* 108(9), 3749-3754.
11. Gillies, R. and Gatenby, R. (2007) "Adaptive landscapes and emergent phenotypes: why do cancers have high glycolysis?," *J. Bioenerg. Biomembr.* 39(3), 251-257.
12. Zhao, S. et al. (2005) "Biologic Correlates of Intratumoral Heterogeneity in 18F-FDG Distribution with Regional Expression of Glucose Transporters and Hexokinase-II in Experimental Tumor," *J. Nucl. Med.* 46(4), 675-682.
13. Dewhirst, M. W. et al. (1999) "Quantification of longitudinal tissue pO2 gradients in window chamber tumours: impact on tumour hypoxia," *Br J. Cancer* 79(11-12), 1717-1722.
14. Swietach, P. et al. (2007) "Regulation of tumor pH and the role of carbonic anhydrase 9," *Cancer Metastasis Rev.* 26(2), 299-310.
15. Baumann, F. et al. (2009) "Lactate promotes glioma migration by TGF-β2-dependent regulation of matrix metalloproteinase-2," *Neuro-oncol.* 11(4), 368-380.
16. Eichten, A. et al. (2007) "Distinctive Features of Angiogenesis and Lymphangiogenesis Determine Their Functionality during De novo Tumor Development," *Cancer Res.* 67(11), 5211-5220.
17. Chang, L. K. et al. (2004) "Dose-dependent response of FGF-2 for lymphangiogenesis," *P.N.A.S.* 101(32), 11658-11663.
18. Pettersson, A. et al. (2000) "Heterogeneity of the Angiogenic Response Induced in Different Normal Adult Tissues by Vascular Permeability Factor/Vascular Endothelial Growth Factor," *Lab. Invest.* 80(1), 99-115.
19. Patan, S. et al. (2001) "Vascular Morphogenesis and Remodeling in a Human Tumor Xenograft: Blood Vessel Formation and Growth After Ovariectomy and Tumor Implantation," *Circ. Res.* 89(8), 732-739.
20. Gimbrone, M. A. et al. (1972) "Tumor Dormancy in Vivo by Prevention of Neovascularization," *J. Exp. Med.* 136(2), 261-276.
21. Warburg, O. (1966) "The Prime Cause and Prevention of Cancer," in *Annual Meeting of Nobel Laureates Jun. 30, 1966*, Landau, Germany.
22. Kim, J.-w. and Dang, C. V. (2006) "Cancer's Molecular Sweet Tooth and the Warburg Effect," *Cancer Res.* 66(18), 8927-8930.
23. Li, C.-Y. et al. (2000) "Initial Stages of Tumor Cell-Induced Angiogenesis: Evaluation Via Skin Window Chambers in Rodent Models," *J. Natl. Cancer Inst.* 92(2), 143-147.
24. Folkman, J. (2000) "Incipient Angiogenesis," *J. Natl. Cancer Inst.* 92(2), 94-95.
25. Haaga, J. R. and Haaga, R. (2013) "Acidic lactate sequentially induced lymphogenesis, phlebogenesis, and arteriogenesis (ALPHA) hypothesis: Lactate-triggered glycolytic vasculogenesis that occurs in normoxia or hypoxia and complements the traditional concept of hypoxia-based vasculogenesis," *Surgery* (0), (e-published Jul. 13, 2013).
26. Coleman, C. N. et al. (2002) "Tumor Hypoxia: Chicken, Egg, or a Piece of the Farm?," *J. Clin. Oncol.* 20(3), 610-615.
27. Chaudary, N. and Hill, R. P. (2007) "Hypoxia and Metastasis," *Clin. Cancer Res.* 13(7), 1947-1949.
28. Llovet, J. M. et al. (2002) "Arterial embolisation or chemoembolisation versus symptomatic treatment in patients with unresectable hepatocellular carcinoma: a randomised controlled trial," *Lancet* 359(9319), 1734-1739.
29. Mankoff, D. A. et al. (2002) "Blood Flow and Metabolism in Locally Advanced Breast Cancer: Relationship to Response to Therapy," *J. Nucl. Med.* 43(4), 500-509.
30. Vander Heiden, M. G. et al. (2009) "Understanding the Warburg Effect: The Metabolic Requirements of Cell Proliferation," *Science* 324(5930), 1029-1033.
31. Weinberg, R. A. (2007) "pRb and Control of the Cell Cycle Clock," in *Biology of Cancer*, Garland Science, New York.
32. Sonveaux, P. et al. (2008) "Targeting lactate-fueled respiration selectively kills hypoxic tumor cells in mice," *J. Clin. Invest.* 118(12), 3930-3942.
33. Semenza, G L. (2008) "Tumor metabolism: cancer cells give and take lactate," *J. Clin. Invest.* 118(12), 3835-3837.
34. Gatenby, R. et al. (2006) "Acid-mediated tumor invasion: a multidisciplinary study," *Cancer Res.* 66(10), 5216-5223.
35. Maxwell, C. et al. (2008) "Cell-surface and mitotic-spindle RHAMM: moonlighting or dual oncogenic functions?," *J. Cell Sci.* 121(Pt 7), 925-932.
36. Fischer, K. et al. (2007) "Inhibitory effect of tumor cell-derived lactic acid on human T cells," *Blood* 109(9), 3812-3819.
37. Martinez-Outschoorn, U. E. et al. (2011) "Ketones and lactate increase cancer cell "stemness," driving recurrence, metastasis and poor clinical outcome in breast cancer: Achieving personalized medicine via Metabolo-Genomics," *Cell Cycle* 10(8), 1271-1286.
38. Samuvel, D. J. et al. (2009) "Lactate Boosts TLR4 Signaling and NF-κB Pathway-Mediated Gene Transcription in Macrophages via Monocarboxylate Transporters and MD-2 Up-Regulation," *J. Immunol.* 182(4), 2476-2484.

39. Brown, M. et al. (2008) "NF-κB in carcinoma therapy and prevention," *Expert Opin. Ther Targets* 12(9), 1109-1122.
40. Karin, M. (2009) "NF-κB as a Critical Link Between Inflammation and Cancer," *Cold Spring Harb. Perspect. Biol.* 1(5).
41. Kondoh, H. et al. (2005) "Glycolytic Enzymes Can Modulate Cellular Life Span," *Cancer Res.* 65(1), 177-185.
42. Lu, H. et al. (2002) "Hypoxia-inducible Factor 1 Activation by Aerobic Glycolysis Implicates the Warburg Effect in Carcinogenesis," *J. Biol. Chem.* 277(26), 23111-23115.
43. Lu, H. et al. (2005) "Reversible Inactivation of HIF-1 Prolyl Hydroxylases Allows Cell Metabolism to Control Basal HIF-1," *J. Biol. Chem.* 280(51), 41928-41939.
44. McFate, T. et al. (2008) "Pyruvate Dehydrogenase Complex Activity Controls Metabolic and Malignant Phenotype in Cancer Cells," *J. Biol. Chem.* 283(33), 22700-22708.
45. Hunt, T. et al. (2007) "Aerobically derived lactate stimulates revascularization and tissue repair via redox mechanisms," *Antioxid. Redox Signal.* 9(8), 1115-1124.
46. Milovanova, T. N. et al. (2008) "Lactate Stimulates Vasculogenic Stem Cells via the Thioredoxin System and Engages an Autocrine Activation Loop Involving Hypoxia-Inducible Factor 1," *Mol. Cell. Biol.* 28(20), 6248-6261.
47. D'Arcangelo, D. et al. (2000) "Acidosis Inhibits Endothelial Cell Apoptosis and Function and Induces Basic Fibroblast Growth Factor and Vascular Endothelial Growth Factor Expression," *Circ. Res.* 86(3), 312-318.
48. Goerges, A. L. and Nugent, M. A. (2004) "pH Regulates Vascular Endothelial Growth Factor Binding to Fibronectin: A Mechanism for Control of Extracellular Matrix Storage and Release," *J. Biol. Chem.* 279(3), 2307-2315.
49. Fukumura, D. et al. (2001) "Hypoxia and Acidosis Independently Up-Regulate Vascular Endothelial Growth Factor Transcription in Brain Tumors in Vivo," *Cancer Res.* 61(16), 6020-6024.
50. Xu, L. et al. (2002) "Acidic Extracellular pH Induces Vascular Endothelial Growth Factor (VEGF) in Human Glioblastoma Cells via ERK1/2 MAPK Signaling Pathway," *J. Biol. Chem.* 277(13), 11368-11374.
51. Shi, Q. et al. (2001) "Regulation of vascular endothelial growth factor expression by acidosis in human cancer cells," *Oncogene* 20(28), 3751-3756.
52. Kumar, V. B. S. et al. (2007) "Endothelial cell response to lactate: Implication of PAR modification of VEGF," *J. Cell Physiol.* 211(2), 477-485.
53. Zabel, D. D. et al. (1996) "Lactate stimulation of macrophage-derived angiogenic activity is associated with inhibition of Poly(ADP-ribose) synthesis," *Lab. Invest.* 74(3), 644-649.
54. Jensen, J. A. et al. (1986) "Effect of lactate, pyruvate, and pH on secretion of angiogenesis and mitogenesis factors by macrophages," *Lab. Invest.* 54(5), 574-578.
55. Végran, F. et al. (2011) "Lactate Influx through the Endothelial Cell Monocarboxylate Transporter MCT1 Supports an NF-κB/IL-8 Pathway that Drives Tumor Angiogenesis," *Cancer Res.* 71(7), 2550-2560.
56. Leite, T. C. et al. (2011) "Lactate downregulates the glycolytic enzymes hexokinase and phosphofructokinase in diverse tissues from mice," *FEBS Lett.* 585(1), 92-98.
57. Lao, M.-S. and Toth, D. (1997) "Effects of Ammonium and Lactate on Growth and Metabolism of a Recombinant Chinese Hamster Ovary Cell Culture," *Biotechnol. Prog.* 13(5), 688-691.
58. Marx, E. et al. (1988) "Lactate-induced inhibition of tumor cell proliferation," Int. *J. Radiat. Oncol. Biol. Phys.* 14(5), 947-955.
59. Cruz, H. et al. (2000) "Effects of ammonia and lactate on growth, metabolism, and productivity of BHK cells," *Enzyme Microb. Technol.* 27(1-2), 43-52.
60. Ozturk, S. S. et al. (1992) "Effects of ammonia and lactate on hybridoma growth, metabolism, and antibody production," *Biotechnol. Bioeng.* 39(4), 418-431.
61. Sattler, U. G. A. et al. (2010) "Glycolytic metabolism and tumour response to fractionated irradiation," *Radiother Oncol.* 94(1), 102-109.
62. Quennet, V. et al. (2006) "Tumor lactate content predicts for response to fractionated irradiation of human squamous cell carcinomas in nude mice," *Radiother. Oncol.* 81(2), 130-135.
63. Gullino, P. M. et al. (1964) "The Interstitial Fluid of Solid Tumors," *Cancer Res.* 24(5), 780-797.
64. Rutz, H. P. (1999) "A biophysical basis of enhanced interstitial fluid pressure in tumors," *Med. Hypotheses* 53(6), 526-529.
65. Tseng, D. et al. (2011) "Targeting SDF-1/CXCR4 to inhibit tumour vasculature for treatment of glioblastomas," *Br. J. Cancer* 104(12), 1805-1809.
66. Salven, P. et al. (2003) "VEGFR-3 and CD133 identify a population of CD34+ lymphatic/vascular endothelial precursor cells," *Blood* 101(1), 168-172.
67. Cao, Y. et al. (1998) "Vascular endothelial growth factor C induces angiogenesis in vivo," *P.N.A.S.* 95(24), 14389-14394.
68. Indraccolo, S. et al. (2006) "Interruption of tumor dormancy by a transient angiogenic burst within the tumor microenvironment," *Proc. Natl. Acad. Sci. U.S.A* 103(11), 4216-4221.
69. Yoshiji, H. et al. (1997) "Vascular Endothelial Growth Factor Is Essential for Initial but not Continued in Vivo Growth of Human Breast Carcinoma Cells," *Cancer Res.* 57(18), 3924-3928.
70. Giavazzi, R. et al. (2001) "Modulation of Tumor Angiogenesis by Conditional Expression of Fibroblast Growth Factor-2 Affects Early but not Established Tumors," *Cancer Res.* 61(1), 309-317.
71. Dvorak, H. F. (2003) "How Tumors Make Bad Blood Vessels and Stroma," *Am. J. Pathol.* 162(6), 1747-1757.
72. Dvorak, H. et al. (1988) "Identification and characterization of the blood vessels of solid tumors that are leaky to circulating macromolecules," *Am. J. Pathol.* 133, 95-109.
73. Kohn, S. et al. (1992) "Pathways of macromolecular tracer transport across venules and small veins. Structural basis for the hyperpermeability of tumor blood vessels," *Lab. Invest.* 67(5), 596-607.
74. Nagy, J. A. et al. (2002) "Vascular Permeability Factor/Vascular Endothelial Growth Factor Induces Lymphangiogenesis as well as Angiogenesis," *J. Exp. Med.* 196 (11), 1497-1506.
75. Nagy, J. A. et al. (2006) "Permeability properties of tumor surrogate blood vessels induced by VEGF-A," *Lab. Invest.* 86(8), 767-780.
76. Robert, J. et al. (2008) "Preoperative Embolization of Hypervascular Castleman's Disease of the Mediastinum," *Cardiovasc. Intervent. Radiol.* 31(1), 186-188.

77. Puma, F. et al. (2008) "Preoperative embolization in surgical management of giant thoracic sarcomas," *Eur. J Cardiothorac. Surg.* 33(1), 127-129.
78. Shi, H. B. et al. (1999) "Preoperative Transarterial Embolization of Spinal Tumor: Embolization Techniques and Results," *Am. J. Neuroradiol.* 20(10), 2009-2015.
79. Kwon, J. H. et al. (2010) "Preoperative transcatheter arterial embolization of hypervascular metastatic tumors of long bones," *Acta Radiol.* 51(4), 396-401.
80. Carli, D. F. M. et al. (2010) "Complications of Particle Embolization of Meningiomas: Frequency, Risk Factors, and Outcome," *Am. J. Neuroradiol.* 31(1), 152-154.
81. Sundaresan, N. et al. (1990) "Treatment of spinal metastases from kidney cancer by presurgical embolization and resection," *J. Neurosurg.* 73(4), 548-554.
82. Breslau, J. and Eskridge, J. M. (1995) "Preoperative Embolization of Spinal Tumors," *J. Vasc. Interv. Radiol.* 6(6), 871-875.
83. Schirmer, C. M. et al. (2006) "Preoperative Embolization of Hypervascular Spinal Metastases Using Percutaneous Direct Injection with n-Butyl Cyanoacrylate: Technical Case Report," *Neurosurgery* 59(2), E431-E432.
84. Finstein, J. L. et al. (2006) "Postembolization paralysis in a man with a thoracolumbar giant cell tumor," *Clin. Orthop. Relat. Res.* 453, 335-340.
85. Lanphere, J. et al. "Embolization," U.S. Pat. No. 7,964,123, application Ser. No. 12/652,552, filed Jan. 5, 2010. (issued Jun. 21, 2011).
86. Colen, C. B. et al. (2011) "Metabolic Targeting of Lactate Efflux by Malignant Glioma Inhibits Invasiveness and Induces Necrosis: An In Vivo Study," *Neoplasia* 13(7), 620-632.
87. Siemann, D. W. (2011) "The unique characteristics of tumor vasculature and preclinical evidence for its selective disruption by Tumor-Vascular Disrupting Agents," *Cancer Treat. Rev.* 37(1), 63-74.
88. Klenke, F. et al. (2007) "Tyrosine kinase inhibitor SU6668 represses chondrosarcoma growth via antiangiogenesis in vivo," *BMC Cancer* 7(1), 49.
89. Figg, W. D. et al. (2002) "Inhibition of Angiogenesis: Treatment Options for Patients with Metastatic Prostate Cancer," *Invest. New Drugs* 20(2), 183-194.
90. Gordon, M. S. et al. (2001) "Phase I Safety and Pharmacokinetic Study of Recombinant Human Anti-Vascular Endothelial Growth Factor in Patients With Advanced Cancer," *J. Clin. Oncol.* 19(3), 843-850.
91. Hurwitz, H. (2003) "Bevacizumab (Avastin, a monoclonal antibody to vascular endothelial growth factor) prolongs survival in first-line colorectal cancer (CRC): results of a phase III trial of bevacizumab in combination with bolus IFL (irinotecan, 5-fluorouracil, leucovorin)," in *Presented at the 39th Annual American Society of Clinical Oncology Meeting*, Chicago, Ill.
92. Cobleigh, M. A. et al. (2003) "A phase I/II dose-escalation trial of bevacizumab in previously treated metastatic breast cancer," *Semin. Oncol.* 30, 117-124.
93. Chen, H. X. et al. (2001) "Clinical trials referral resource: Current clinical trials of the anti-VEGF monoclonal antibody bevacizumab," *Oncology (Williston Park)* 15(8), 1017, 1020, 1023-1016.
94. O'Connor, J. P. et al. (2012) "Dynamic contrast-enhanced MRI in clinical trials of antivascular therapies," *Nature Reviews Clinical Oncology* 9(3), 167-177.
95. Padhani, A. R. and Husband, J. E. (2001) "Dynamic contrast-enhanced MRI studies in oncology with an emphasis on quantification, validation and human studies," *Clin. Radiol.* 56(8), 607-620.
96. Koh, T. S. et al. (2011) "Fundamentals of tracer kinetics for dynamic contrast-enhanced MRI," *J. Magn. Reson. Imaging* 34(6), 1262-1276.
97. Sourbron, S. (2010) "Technical aspects of MR perfusion," *Eur. J. Radiol.* 76(3), 304-313.
98. Barrett, T. et al. (2006) "Macromolecular MRI contrast agents for imaging tumor angiogenesis," *Eur J. Radiol.* 60(3), 353-366.
99. Brasch, R. et al. (1997) "Assessing tumor angiogenesis using macromolecular MR imaging contrast media," *J. Magn. Reson. Imaging* 7(1), 68-74.
100. Feng, Y. et al. (2008) "Characterization of tumor angiogenesis with dynamic contrast-enhanced MRI and biodegradable macromolecular contrast agents in mice," *Magn. Reson. Med.* 60(6), 1347-1352.
101. Haas, B. R. and Sontheimer, H. (2010) "Inhibition of the Sodium-Potassium-Chloride Cotransporter Isoform-1 reduces glioma invasion," *Cancer research* 70(13), 5597-5606.
102. Algharabil, J. et al. (2012) "Inhibition of Na(+)-K(+)-2Cl(−) cotransporter isoform 1 accelerates temozolomide-mediated apoptosis in glioblastoma cancer cells," *Cell. Physiol. Biochem* 30(1), 33-48.
103. Iwamoto, L. M. et al. (2004) "Na—K-2Cl cotransporter inhibition impairs human lung cellular proliferation," *Am. J. Physiol. Lung. Cell Mol. Physiol.* 287(3), L510-514.
104. St Lawrence, K. S. and Lee, T. Y. (1998) "An adiabatic approximation to the tissue homogeneity model for water exchange in the brain: I. Theoretical derivation," *J. Cereb. Blood Flow Metab.* 18(12), 1365-1377.
105. Henderson, E. et al. (2000) "Simultaneous MRI measurement of blood flow, blood volume, and capillary permeability in mammary tumors using two different contrast agents," *J. Magn. Reson. Imaging* 12(6), 991-1003.
106. Barrett, T. et al. (2007) "MRI of tumor angiogenesis," *J. Magn. Reson. Imaging* 26(2), 235-249.
107. O'Connor, J. P. et al. (2007) "DCE-MRI biomarkers in the clinical evaluation of antiangiogenic and vascular disrupting agents," *Br J. Cancer* 96(2), 189-195.
108. Turkbey, B. et al. (2010) "The role of dynamic contrast-enhanced MRI in cancer diagnosis and treatment," *Diagn. Interv. Radiol.* 16(3), 186-192.
109. Padhani, A. R. and Leach, M. O. (2005) "Antivascular cancer treatments: functional assessments by dynamic contrast-enhanced magnetic resonance imaging," *Abdom. Imaging* 30(3), 324-341.
110. Tofts, P. S. (1997) "Modeling tracer kinetics in dynamic Gd-DTPA MR imaging," *J. Magn. Reson. Imaging* 7(1), 91-101.
111. Tofts, P. S. et al. (1995) "Quantitative analysis of dynamic Gd-DTPA enhancement in breast tumors using a permeability model," *Magn. Reson. Med.* 33(4), 564-568.
112. Sourbron, S. P. and Buckley, D. L. (2012) "Tracer kinetic modelling in MRI: estimating perfusion and capillary permeability," *Phys. Med. Biol.* 57(2), R1-33.
113. Wu, X. et al. (2009) "Tumor characterization with dynamic contrast enhanced magnetic resonance imaging and biodegradable macromolecular contrast agents in mice," *Pharm. Res.* 26(9), 2202-2208.

We claim:

1. A method for treating a patient with cancer, said method comprising:

a) administering an effective amount of a composition comprising a lactate transporter inhibitor to a patient comprising a cancerous lesion, wherein the cancerous lesion comprises a plurality of blood vessels, wherein said lactate transporter inhibitor is selected from the group consisting of ferrulic acid, caffeic acid, chlorogenic acid, resveratrol ferulate, and phloretin ferulate, and b) occluding at least one of said plurality of blood vessel.

2. The method according to claim 1 wherein said composition is delivered via liposomes.

3. The method according to claim 1 wherein the method further comprises administering to said patient an effective amount of an angiogenesis inhibitor.

4. The method according to claim 3 wherein said angiogenesis inhibitor is a humanized monoclonal antibody.

5. The method of claim 4, wherein said antibody is bevacizumab.

6. The method according to claim 3 wherein said treating comprises repeated administration of a composition comprising at least one of the following: lactate transporter inhibitor and angiogenesis inhibitor.

7. The method according to claim 1 wherein said cancer is hypoxic cancer.

8. The method according to claim 1 wherein said occluding further comprises an embolism.

9. The method according to claim 8 wherein said embolism is produced by the introduction of an embolic composition.

10. The method according to claim 9 wherein said embolic composition comprises a plurality of polymers embedded with lactate transporter inhibitors.

11. The method according to claim 9 wherein said embolic composition comprises a plurality of glass beads coated with at least one lactate transporter inhibitor.

12. The method according to claim 1 wherein said occluding of blood vessels providing blood to said cancer comprises thermal ablation.

13. The method according to claim 12 wherein said treating of said cancer with thermal ablation is preceded with lactate transporter inhibitor treatment.

14. A method for shrinking a cancerous lesion in a patient with cancer, said method comprising:
    a) administering an effective amount of a composition comprising a lactate transporter inhibitor to a patient comprising a cancerous lesion, wherein the cancerous lesion comprises a plurality of blood vessels, wherein said lactate transporter inhibitor is selected from the group consisting of ferrulic acid, caffeic acid, chlorogenic acid, resveratrol ferulate, and phloretin ferulate, and
    b) occluding at least one of said plurality of blood vessel.

15. A method of treating cancer comprising administering to a patient a composition comprising an effective amount of a lactate transporter inhibitor, a NKCC inhibitor, and an angiogenesis inhibitor, wherein said lactate transporter inhibitor is selected from the group consisting of ferrulic acid, caffeic acid, chlorogenic acid, resveratrol ferulate, and phloretin ferulate and wherein said NKCC inhibitor comprises bumetanide.

16. The method according to claim 15 wherein said composition is delivered via liposomes.

17. The method according to claim 15 wherein said angiogenesis inhibitor is a humanized monoclonal antibody.

18. The method of claim 17, wherein said antibody is bevacizumab.

19. The method according to claim 15 wherein said composition comprising at least one lactate transporter inhibitor, NKCC inhibitor, and an angiogenesis inhibitor is administered as a pharmaceutical cocktail.

20. The method according to claim 15 wherein said treating comprises repeated administration of at least one of the lactate transporter inhibitor, NKCC inhibitor, and an angiogenesis inhibitor.

21. The method according to claim 15 wherein said cancer is hypoxic cancer.

* * * * *